(12) United States Patent
Chen et al.

(10) Patent No.: US 7,923,562 B2
(45) Date of Patent: Apr. 12, 2011

(54) PHOTOCLEAVABLE LINKER METHODS AND COMPOSITIONS

(75) Inventors: James K. Chen, Mountain View, CA (US); Surajit Sinha, Madurdaha (IN); Ilya Shestopalov, Mountain View, CA (US); Xiaohu Ouyang, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 5 days.

(21) Appl. No.: 12/485,774

(22) Filed: Jun. 16, 2009

(65) Prior Publication Data

US 2010/0022761 A1    Jan. 28, 2010

Related U.S. Application Data

(60) Provisional application No. 61/061,940, filed on Jun. 16, 2008.

(51) Int. Cl.
| | |
|---|---|
| C07D 311/16 | (2006.01) |
| C07D 307/91 | (2006.01) |
| C07D 215/14 | (2006.01) |
| C07D 207/273 | (2006.01) |
| C07D 207/46 | (2006.01) |
| C07D 405/12 | (2006.01) |
| C07C 229/22 | (2006.01) |
| C07C 205/06 | (2006.01) |

(52) U.S. Cl. ........ 546/175; 548/519; 548/525; 548/546; 549/289; 549/461; 580/155; 580/156

(58) Field of Classification Search ................ None
See application file for complete search history.

(56) References Cited

FOREIGN PATENT DOCUMENTS
WO        WO 03/006506    *    1/2003

OTHER PUBLICATIONS

Ando, et al., "Photo-mediated gene activation using caged RNA/DNA in zebrafish embryos", Nature Genetics (2001), 28:317-325.
Fedoryak, et al., "Brominated Hydroxyquinoline as a Photolabile Protecting Group with Sensitivity to Multiphoton Excitation", Organic Letters (2002), 4(20);3419-3422.
Shestopalov, et al., "Light-controlled gene silencing in zebrafish embryos", Nature Chemical Biology (2007), 3(10):650-651.

* cited by examiner

*Primary Examiner* — Yong Chu
*Assistant Examiner* — Alicia L Otton
(74) *Attorney, Agent, or Firm* — Bozicevic, Field & Francis LLP; Pamela J. Sherwood

(57) ABSTRACT

Bifunctional linkers are provided that comprise a photocleavable moiety flanked by two different amine reactive moieties. In some embodiments the photocleavable moiety is a dimethoxynitrobenzyl moiety. In other embodiments the photocleavable moiety is 8-bromo-7-hydroxyquinoline. In other embodiments the photocleavable moiety is nitrodibenzofuran. In other embodiments the photocleavable moiety is 6-bromo-7-hydroxycoumarin-4-ylmethyl. The linkers find use in synthetic methods, including the generation of photocleavable oligonucleotides, e.g. caged morpholinos.

5 Claims, 10 Drawing Sheets

PHOTOCLEAVABLE LINKER METHODS AND COMPOSITIONS

FEDERALLY SPONSORED RESEARCH AND DEVELOPMENT

This invention was made with Government support under contract GM072600 awarded by the National Institutes of Health. The Government has certain rights in this invention.

BACKGROUND OF THE INVENTION

The physical and chemical factors that allow polynucleotides to perform their functions in the cell have been studied for several decades. Recent advances in the synthesis and manipulation of polynucleotides have allowed this field to move ahead especially rapidly during the past fifteen years. One of the most common chemical approaches to the study of interactions involving biomolecules has been the use of nucleoside base analogs in which functional groups are added, deleted, blocked, or rearranged.

Such nucleoside analogs may be useful as in providing specific alterations to reaction kinetics; properties to oligonucleotide probes for diagnostic applications; to alter the properties of antisense RNA and RNAi; and in the synthesis and purification of oligonucleotides. Among the uses of oligonucleotides are methods of inhibiting gene expression with antisense oligonucleotides complementary to a specific target messenger RNA (mRNA) sequences. Oligonucleotides also have found use in diagnostic tests performed using biological fluids, tissues, intact cells or isolated cellular components. For diagnostics, oligonucleotides and oligonucleotide analogs can be used in cell free systems, in vitro, ex vivo or in vivo.

Oligonucleotides and nucleosides are also widely used as research reagents. They are useful for understanding the function of many other biological molecules as well as in the preparation of such other biological molecules. For example, oligonucleotides serve as primers in the reactions associated with polymerase chain reaction (PCR), which reactions are now widely used in forensics, paleontology, evolutionary studies and genetic counseling, to name just a few.

The use of antisense oligonucleotides to knock down gene expression is of great interest. In many cases, gene knockdowns with oligonucleotides have been achieved primarily through the injection of antisense molecules, after which the targeted RNAs are silenced for a period of up to several days. However, this does not permit conditional gene silencing. One approach for overcoming temporal and/or spatial limitations on knockdowns utilizes "caged" molecules that are photoactivatable, thereby providing for temporal or tissue specificity. Improved methods and compositions for conjugated linkers to oligonucleotides are of interest for a variety of applications.

Among widely used antisense molecules are morpholino oligonucleotides, which contain a six-membered morpholine ring in place of a ribose sugar, and a phosphorodiamidate backbone. Morpholinos are often used as a research tool for reverse genetics by knocking down gene function, and are also in development as pharmaceutical therapeutics targeted against pathogenic organisms and for amelioration of genetic diseases. Because of their synthetic backbone, morpholinos are not recognized by cellular proteins, and so are not degraded by nucleases in cells or in serum. Activities of morpholinos against a variety of targets, including miRNA, mRNA, and ribozymes suggest that they can be used as a general-purpose tool for blocking interactions of proteins or nucleic acids with mRNA.

Linker compounds that allow photoactivation of molecules are of great interest for a number of purposes, including photoactivation of drugs, antisense oligonucleotides, and the like. The present invention provides linkers and compositions derived therefrom for such purposes.

SUMMARY OF THE INVENTION

Compositions of bifunctional photocleavable linkers are provided. Also provided are methods for the synthesis of the bifunctional linkers, and methods of using the bifunctional linkers in the synthesis of light activated macromolecules, including, without limitation, caged antisense molecules; polypeptides; and the like. The bifunctional linkers allow modification of readily available molecules, including oligonucleotides modified to have a reactive amine moiety.

The bifunctional linkers of the invention comprise a photocleavable moiety flanked by two different amine reactive moieties. In some embodiments the photocleavable moiety is a dimethoxynitrobenzyl moiety. In other embodiments the photocleavable moiety is 8-bromo-7-hydroxyquinoline. In other embodiments the photocleavable moiety is nitrodibenzofuran. In other embodiments the photocleavable moiety is 6-bromo-7-hydroxycoumarin-4-ylmethyl.

In certain embodiments of the invention, the bifunctional linkers are used to link two oligonucleotides, which oligonucleotides may be DNA, RNA, or an analog thereof, including oligonucleotides having a phosphoroamidite backbone, peptide nucleic acids, morpholinos, etc., as are known in the art. The linked oligonucleotides may be complementary, for example so as to form a caged structure.

DETAILED DESCRIPTION OF THE EMBODIMENTS

Figure 1:
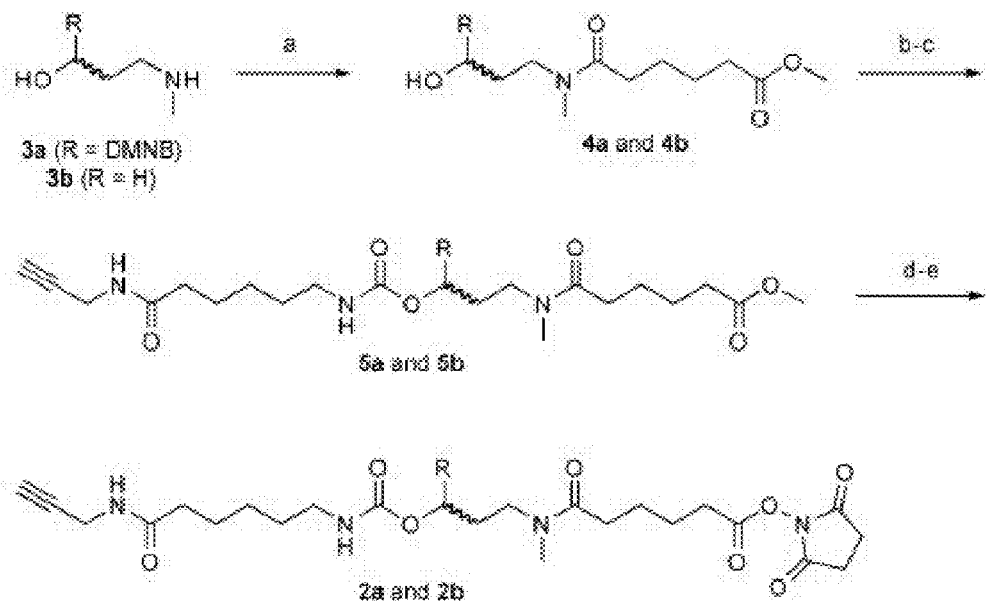
FIG. 1 illustrates the synthesis of a bifunctional photocleavable linker.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury CN), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)- isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Where the methods of the invention are utilized to produce a photocleavable oligonucleotide, the molecule can be introduced into the target cell(s) using any convenient protocol, where the protocol will vary depending on whether the target cells are in vitro or in vivo. A number of options can be utilized to deliver the oligomer into a cell or population of cells such as in a cell culture, tissue, organ or embryo. For instance, oligomers can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the oligomers, liposome-mediated transfection, or transfection using chemicals such as calcium phosphate.

For example, the oligonucleotide can be fed directly to, injected into, the host organism containing the target gene. The agent may be directly introduced into the cell (i.e., intracellularly); or introduced extracellularly into a cavity, interstitial space, into the circulation of an organism, introduced orally, etc. Physical methods of introducing nucleic acids include injection directly into the cell or extracellular injection into the organism of an oligonucleotide solution. The agent may be introduced in an amount which allows delivery of at least one copy per cell. Higher doses (e.g., at least 5, 10, 100, 500 or 1000 copies per cell) of the agent may yield more effective inhibition; lower doses may also be useful for specific applications. In some embodiments the morpholinos are conjugated to a moiety to enhance cellular uptake, e.g. conjugates of cholesterol, conjugated to a transport moiety, etc. Transport moieties of interest include tat peptides, poly-arginine peptides, poly-guanidinium, etc., as known in the art.

When liposomes are utilized, substrates that bind to a cell-surface membrane protein associated with endocytosis can be attached to the liposome to target the liposome to T cells and to facilitate uptake. Examples of proteins that can be attached include capsid proteins or fragments thereof that bind to T cells, antibodies that specifically bind to cell-surface proteins on T cells that undergo internalization in cycling and proteins that target intracellular localizations within T cells. Gene marking and gene therapy protocols are reviewed by Anderson et al. (1992) Science 256:808-813.

In certain embodiments, a hydrodynamic nucleic acid administration protocol is employed. Where the agent is a ribonucleic acid, the hydrodynamic ribonucleic acid administration protocol described in detail below is of particular interest. Where the agent is a deoxyribonucleic acid, the hydrodynamic deoxyribonucleic acid administration protocols described in Chang et al., J. Virol. (2001) 75:3469-3473; Liu et al., Gene Ther. (1999) 6:1258-1266; Wolff et al., Science (1990) 247: 1465-1468; Zhang et al., Hum. Gene Ther. (1999) 10:1735-1737: and Zhang et al., Gene Ther. (1999) 7:1344-1349; are of interest.

Additional nucleic acid delivery protocols of interest include, but are not limited to: those described in U.S. Patents of interest include U.S. Pat. Nos. 5,985,847 and 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc.

Depending on the nature of the agent, a photocleavable oligonucleotide may be administered to the host using any convenient means capable of resulting in the desired result. Thus, the agent can be incorporated into a variety of formulations for administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific compound, the nature of the delivery vehicle, and the like. Preferred dosages for a given compound are readily determinable by those of skill in the art by a variety of means.

Compositions

Compositions of bifunctional photocleavable linkers are provided, which allow modification of readily available molecules, including oligonucleotides modified to have a reactive amine moiety. In an alternative embodiment the linker comprises two different reactive amines, for use in the modification of oligonucleotides modified to have reactive X groups as defined below. In another alternative embodiment polyethylene glycol polymers are substituted for the illustrated alkyl linkers. The bifunctional linkers of the invention have the structure:

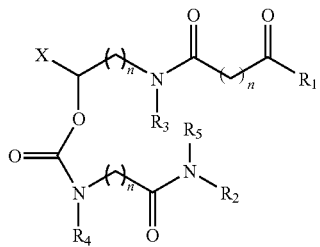

I where X is a photocleavable moiety. X may be photolysed in UV light, e.g. where X is selected from a 1,2-dimethoxy-4-nitrobenzyl moiety;

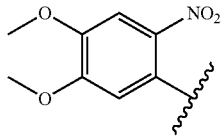

a 1,2-dimethoxy-2-nitrobenzyl moiety; or a nitrodibenzofuran moiety

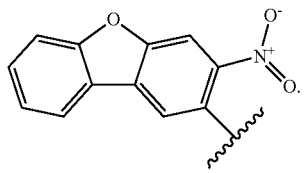

X may alternatively be photolysed by infrared and multiphoton excitation, e.g. where X is selected from 6-bromo-7-hydroxycoumarin-4-ylmethyl:

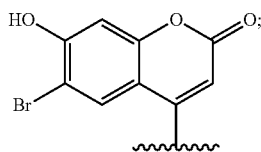

and 8-bromo-7-hydroxyquinolinyl:

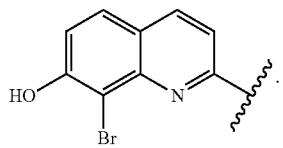

The nitrodibenzofuran, bromohydroxyquinoline, and bromohydroxycoumarin groups are also compatible with single-photon UV light.

$R_1$ and $R_2$ contain different reactive moieties used for conjugation. This includes, without limitation: amine reactive moieties such as succinimide moieties and isothiocyanate moieties, thiol reactive moieties such as iodoacetamide moieties and maleimide moieties, and moieties used in cycloaddition such as propargyl moieties, azide moieties, and terminal alkene moieties.

In some embodiments $R_1$ and $R_2$ are independently selected from succinimide (NHS ester):

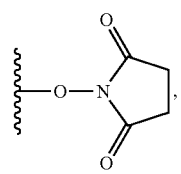

isothiocyanate

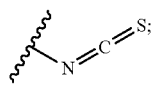

propargyl

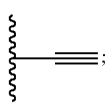

iodoacetamide

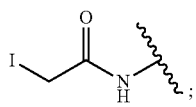

maleimide

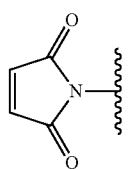

azide

and terminal alkene

$R_3$, $R_4$ and $R_5$ are independently selected from H and C1-C6 lower alkyls, e.g. CH, $CH_2CH_3$, etc.;

and each n is an independently selected integer from 0 to 10, usually from 0 to 5, and may be from 0-3.

The linkers of the invention are useful in any joining of molecules where a photocleavable linkage is desired. In some embodiments, the bifunctional linkers are used in the joining of oligonucleotides, to generate the structure:

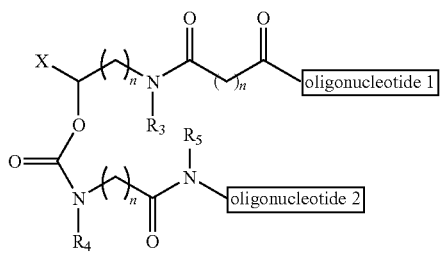

II where X, n, and $R_3$, $R_4$ and $R_5$ are as defined above. Oligonucleotide 1 and oligonucleotide 2 may be any RNA, DNA or analog thereof, including locked nucleic acids (LNA), etc., methylations, morpholino derivatives; phosphoroamidate derivatives; unusual base-pairing combinations such as the isobases isocytidine and isoguanidine and the like morpholino, peptide nucleic acid, etc. The oligonucleotides may be of any size. In some embodiments the oligonucleotides are at least about 10 nt in length and not more than about 50 nt in length, and may be not more than about 49 nt, not more than about 30 nt., not more than about 25 nt. In some embodiments oligonucleotide 1 and oligonucleotide 2 are complementary and are not equal in size, e.g. where one oligonucleotide is about 25 to about 30 nt in length and the other oligonucleotide is from about 10 to about 15 nt in length, e.g. about 10 to about 12 nt in length.

One or both of the oligonucleotides may comprise a label, which may be fluorescent, luminescent, radioactive, enzymatically active, etc. Suitable labels include fluorochromes, e.g. fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label.

The oligonucleotide can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes. Modifications to introduce a nonpolar base analog of the invention may be used as a primer in a synthetic reaction, e.g. PCR; may be introduced at any position during in vitro or in vivo synthesis; and the like.

Purines and pyrimidines other than those normally found in nature may also be included in oligonucleotides. For example, deaza or aza purines and pyrimidines may be used in place of naturally purine or pyrimidine bases and pyrimidine bases having substituent groups at the 5- or 6-positions; purine bases may have altered or replacement substituent groups at the 2-, 6- or 8-positions.

Modified oligonucleotides of the invention may be provided in solution, or bound to a substrate. One, a pair or a plurality of modified probes may be provided in any configuration. By "solid substrate" or "solid support" is meant any surface to which the probes of the invention are attached. A variety of solid supports or substrates are suitable for the purposes of the invention, including both flexible and rigid substrates. By flexible is meant that the support is capable of being bent, folded or similarly manipulated without breakage. Examples of flexible solid supports include nylon, nitrocellulose, polypropylene, polyester films, such as polyethylene terephthalate, etc. Rigid supports do not readily bend, and include glass, fused silica, quartz, acrylamide; plastics, e.g. polytetrafluoroethylene, polypropylene, polystyrene, polystyrene and sulfonated polystyrene-divinyl benzene, quaternized product of chloromethylated polystyrene-divinyl benzene, PEG-polystyrene, PEG, polycarbonate, and blends thereof, and the like; metals, e.g. gold, platinum, silver, and the like; etc. The substrates can take a variety of configurations, including planar surfaces, filters, fibers, membranes, beads, particles, dipsticks, sheets, rods, etc. The substrates can be prepared using any convenient means. One means of preparing the supports is to synthesize the probes, and then deposit them on the support surface. The probes can be deposited on the support using any convenient methodology, including manual techniques, e.g. by micropipette, ink jet, pins, etc., and automated protocols. The probes may also be covalently attached to the substrate, using methods known in the art. Alternatively, the probes can be synthesized on the substrate using standard techniques known in the art.

The bifunctional linkers of the invention may be used in synthetic reaction with amine modified oligonucleotides, e.g. an oligonucleotide having a 3' or 5' reactive amine, normally linked to the backbone, e.g. to a phosphate. Such reactive oligonucleotides are commercially available and are known in the art. Usually each oligonucleotide will have a different reactive amine, and the synthesis will proceed in a stepwise manner to add each oligonucleotide in a separate reaction. Reactive amines include, without limitation:

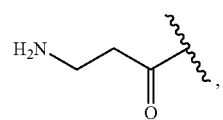

-continued

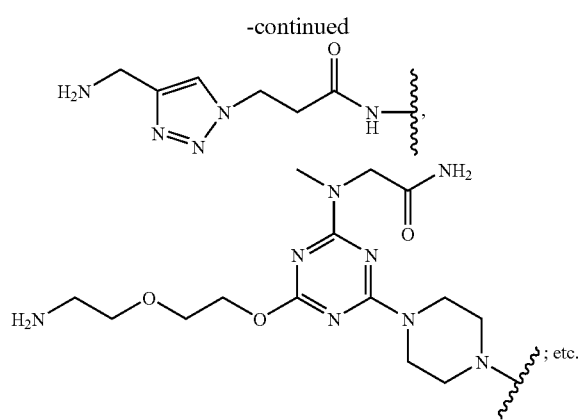

Following reaction with an amine modified nucleotide, a molecule having structure II is generated. Specific oligonucleotides of interest include the following structures:

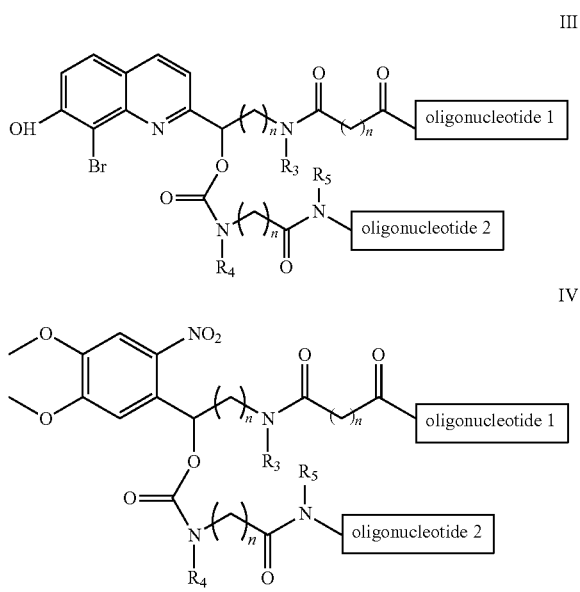

where oligo 1 and oligo 2 are optionally complementary and of different lengths. In some embodiments oligo 1 and oligo 2 are morpholino oligonucleotides.

Nucleotides, oligonucleotides and polynucleotides produced by the methods of the invention may be used in any of the techniques known in the art for such molecules.

Kits

Also provided are kits for practicing the subject methods. The kits according to the present invention may comprise: (a) a bifunctional linker of the invention, and may further comprise buffers, oligonucleotides, and the like for performing synthetic reactions; and (b) instructions for using the provided bifunctional linker. Such linkers may be provided lyophilized, in solution, etc.

The various reagent components of the kits may be present in separate containers, or may all be precombined into a reagent mixture for combination with samples. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Experimental

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

The constitutive, global effects of genetic mutations and conventional morpholinos limit their use in functional genomic studies, and reagents that convey conditional control of endogenous genes allows new directions in developmental biology research. The optical transparency of zebrafish embryos provides a opportunity for light-directed technologies. Here we describe the synthesis of a caged morpholino targeting ntl, spatiotemporal analyses of ntl function, steps toward the isolation of embryonic cells for tissue-specific microarrays, and a synthetic strategy that facilitates the preparation of caged reagents against other genes. These studies demonstrate the ability to temporally and spatially regulate zebrafish gene expression and support roles for ntl in gastrulation movements, cell fate commitment within the chordamesoderm, and notochord maturation.

Design and Synthesis of a Caged ntl Morpholino. Morpholino activity can be regulated by tethering a complementary oligomer through a photocleavable linker, resulting in a stem-loop structure. Intramolecular self-complementation abrogates annealing of the morpholino to its RNA target, whereas linker photolysis releases the inhibitor oligomer from the active morpholino.

Methods were devised for coupling an inhibitory oligomer to a conventional 25-base ntl morpholino (ntl MO; 5'-GACT-TGAGGCAGACATATTTCCGAT-3') (SEQ ID NO:1) through a photocleavable linker. Based on morpholino/RNA melting temperatures, we estimated that the inhibitor oligomer should contain at least ten nucleotides, and a decamer (5'-TATGTCTGCC-3') (SEQ ID NO:2) was synthesized on solid phase using morpholino phosphoramidate monomers. The 5' end of the inhibitory oligomer was functionalized with propargylglycine and a dimethoxynitrobenzyl (DMNB)-based linker, and fluorescein was attached to the 3' amine to allow visualization by fluorescence microscopy. The ntl MO was then derivatized with an acyl azide, and the two oligomers were conjugated by Cu(I)-catalyzed Huisgen 1,3-dipolar cycloaddition. The resulting caged ntl morpholino (ntl cMO) was purified by ion exchange HPLC and its structure was confirmed by electrospray mass spectrometry. Quantification of the ntl cMO for in vivo studies was determined by its absorbance of 260-nm and 498-nm light.

Evaluation of the ntl cMO in Zebrafish Embryos. Wild-type embryos were injected at the one cell stage with the ntl cMO (115 fmol/embryo; this is twice the dose required to obtain a ntl mutant phenotype with the conventional morpholino) and were either globally irradiated with 360-nm light (13 mW/cm$^2$) for 10 seconds at the sphere stage (4 hpf)

or cultured in the dark. Injected embryos that were not exposed to 360-nm light developed normally, whereas the majority of irradiated embryos lost posterior structures, lacked notochord cells, and exhibited U-shaped somites. This mutant phenotype is identical to that observed in ntl mutants and morphants and is due to ntl cMO photoactivation, since uninjected wild-type embryos and embryos injected with the propargylglycine- and DMNB-functionalized decamer were not affected by 360-nm light irradiation. Further confirmation that Ntl protein expression is silenced in the ntl cMO-injected embryos upon photocleavage was obtained by Western blot analysis.

Figure 3:
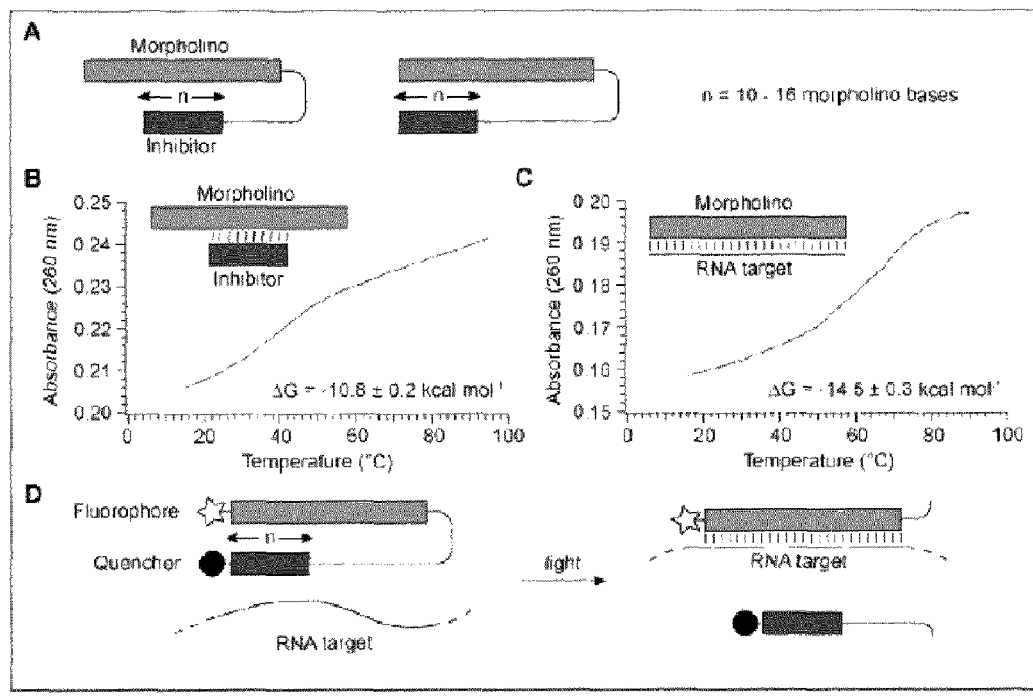
FIG. 3 illustrates biophysical studies of caged morpholinos.

Ntl loss-of-function phenotypes can be categorized into four classes according to their severity: class I=a fully penetrant ntl mutant phenotype characterized by no notochord, U-shaped somites, and a lack of posterior structures; class II=no notochord, U-shaped somites, and some posterior somites; class III=incompletely vacuolated notochord, V-shaped somites, and a shortened anterior-posterior axis; and class IV=wildtype phenotype (FIG. 3A).[7] These phenotypes can be recapitulated by injecting early-stage embryos with varying doses of the conventional ntl MO, and classes I to IV correspond respectively to doses of 115 fmol/embryo or greater, 57 fmol/embryo, 28 fmol/embryo, and 14 fmol/embryo or less (FIG. 3B). Since the class I phenotype can be achieved with ntl MO levels equal to or exceeding 115 fmol/embryo, we utilized 8a at this minimum dose in this experiment. 8a induced class II and class III phenotypes in the absence of irradiation (FIG. 3C), while our original ntl cMO exhibited little activity prior to uncaging. A difference in caging efficiency may reflect changes in the linker structure.

Spatiotemporal Control of ntl Expression Using the Caged Morpholino. Having established the efficacy of the ntl cMO, we evaluated its ability to convey temporal control of ntl function. We globally irradiated ntl cMO-injected embryos at the 16-cell (1.5 hpf), sphere, shield, and 6-somite (12 hpf) stages and observed the resulting phenotypes at 1 day post fertilization (dpf). Four major phenotypes were observed: class I=ntl mutant phenotype; class II=no notochord, U-shaped somites, and some posterior somites; class III=incompletely vacuolated notochord, chevron-shaped somites, and a shortened anterior-posterior axis; and class IV=wild-type phenotype.

Photoactivation of the ntl cMO at the 16-cell and sphere stages resulted primarily in a ntl mutant phenotype, consistent with the onset of ntl expression at 4 hpf. In contrast, ntl cMO activation at the shield and 6-somite stages produced partial patterning defects. Although nearly all embryos irradiated at the shield stage lacked notochord and exhibited U-shaped somites, a significant percentage of embryos had some limited posterior development. Accordingly, immunostaining of these embryos demonstrated that Ntl protein persists temporarily in the tailbud after ntl cMO activation. These protein expression analyses also reveal that ntl silencing at the shield stage results in the dramatic accumulation of cells with reduced Ntl levels in the ventrolateral margin, as well as the movement of cells that do not express Ntl into the shield and chordamesoderm. Due to the kinetics of Ntl protein degradation and the localization of ntl-expressing cells in wild-type embryos, it is likely the shield and chordamesoderm cells in irradiated ntl cMO-injected embryos are derived from populations that did not express ntl prior to morpholino uncaging. Similar results are obtained when visualizing ntl transcripts in ntl MO-injected embryos.

Uncaging the ntl cMO at the 6-somite stage yielded embryos with incompletely vacuolated notochord cells, chevron-shaped somites, and a shortened anterior-posterior axis. Ntl therefore continues to be required after notochord specification for its maturation.

Light-mediated morpholino activation should enable spatial control with cellular resolution. We therefore investigated our ability to inhibit ntl expression in a spatially restricted manner by targeting a region of the chordamesoderm after gastrulation. Wild-type embryos were co-injected at the one-cell stage with the ntl cMO and mRNA encoding the Kaede protein, which undergoes a green to-red fluorescence photoconversion upon exposure to 360-nm light. The embryos were cultured until the bud stage (10 hpf), at which point gastrulation is complete and the ntl-expressing notochord progenitor cells have entered the chordamesoderm. A circular, 100-μm wide region of axial cells anterior to the tailbud was then irradiated, activating the ntl cMO in the axial ectoderm and underlying chordamesoderm. The irradiated cells exhibited red fluorescence and remained clustered in an axial domain spanning four to five somites at 1 dpf. Red fluorescence was excluded from the differentiated notochord cells, and the majority of the irradiated cells were located within or closely associated with the floor plate. Notochord abnormalities and U-shaped somites were also observed in this region, while adjacent non-irradiated tissues had differentiated notochord cells and chevron-shaped somites. Embryos injected with Kaede mRNA alone and irradiated in a similar manner exhibited fluorescently labeled floor plate and notochord cells without patterning defects.

Interestingly, the relative positions of labeled floor plate cells and cells normally fated to become notochord appear to be different in the two experimental conditions. In the developing chordamesoderm, notochord progenitors and overlying floor plate progenitors normally shear relative to one another such that the resulting notochord cells are located more anteriorly than floor plate cells originating from the same region. Notochord progenitors in which the ntl cMO is activated appear to ultimately occupy more posterior positions relative to co-irradiated floor plate cells, suggesting that ntl is also required for morphogenetic movements within the chordamesoderm.

Figure 4:
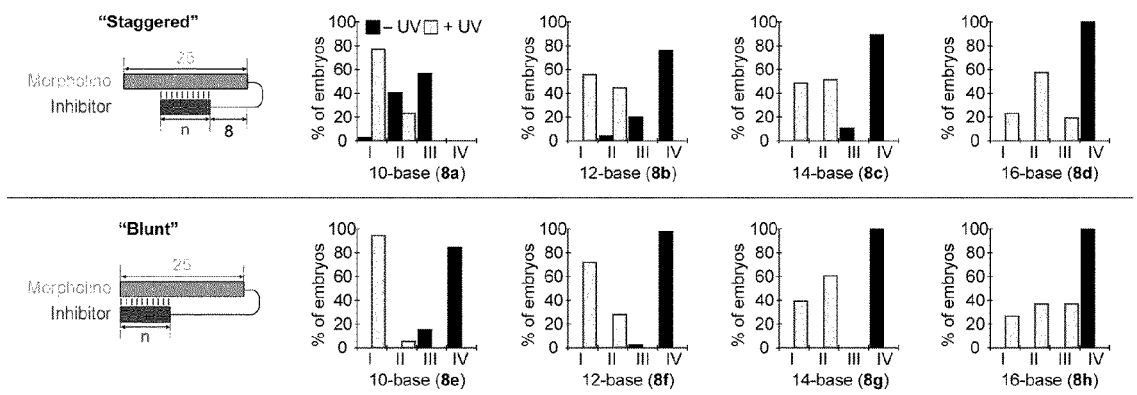
FIG. 4 illustrates activity profiles of ntl cMOs of different structures. Schematic representation of "staggered" and "blunt" cMO configurations (n=number of bases) and the distribution of phenotypes for each cMO configuration are shown.

Gene-Silencing Activities and Biophysical Properties of Hairpin ntl cMOs. Reasoning that hairpin cMO efficacy depends on the interplay between inhibitor length, stem-loop configuration, and linker formats, we used crosslinker 2a to prepare ntl cMOs with differing structures (8a-h; FIG. 4 and Table 1). In particular, we varied the length of the inhibitory MO (10, 12, 14, and 16 bases) and evaluated both "blunt" and "staggered" stem-loops. Each ntl cMO was synthesized, purified by ion-exchange HPLC, injected into one-cell stage zebrafish embryos, and photoactivated as before, except a dose of 230 fmol/embryo was evaluated for each case. This higher cMO concentration was used for these studies to maximize our ability to identify caged configurations with minimum basal activity. FIG. 4 illustrates activity profiles of ntl cMOs of different structures. Schematic representation of "staggered" and "blunt" cMO configurations (n=number of bases) and the distribution of phenotypes for each cMO configuration 8a-h (see Table 1) at a dose of 230 fmol/embryo are shown.

The resulting phenotypes confirm that hairpin cMO activity varies significantly with inhibitor length and stem-loop structure. Within a stem-loop configuration, increasing the number of bases in the inhibitory oligomer decreased cMO activity in both basal and photoactivated conditions. The "blunt" and "staggered" stem-loop configuration also exhibited distinct activity profiles. The "staggered" system failed to achieve an adequate activity differential between caged and uncaged forms under any of the conditions we tested. As described above, cMO 8a still exhibited gene-silencing activity in its caged form, even though it successfully induced class I phenotypes upon photoactivation. The other "staggered" cMOs had lower basal activities (8b-d), but their uncaged forms failed to yield strong ntl mutant phenotypes. In contrast, the "blunt" stem-loop design provided greater caging efficiency, and two cMOs, 8e and 8f, exhibited dynamic ranges appropriate for conditional gene silencing; the two reagents did not induce mutant phenotypes in their caged forms, and photoactivation of the cMOs yielded fully penetrant phenotypes in most embryos. Since our linker 1-based ntl cMO utilizes the same inhibitory oligomer as the "staggered" reagent 8a,[7] these results underscore the importance of matching linker and stem-loop structures for optimum cMO activity.

Figure 5:
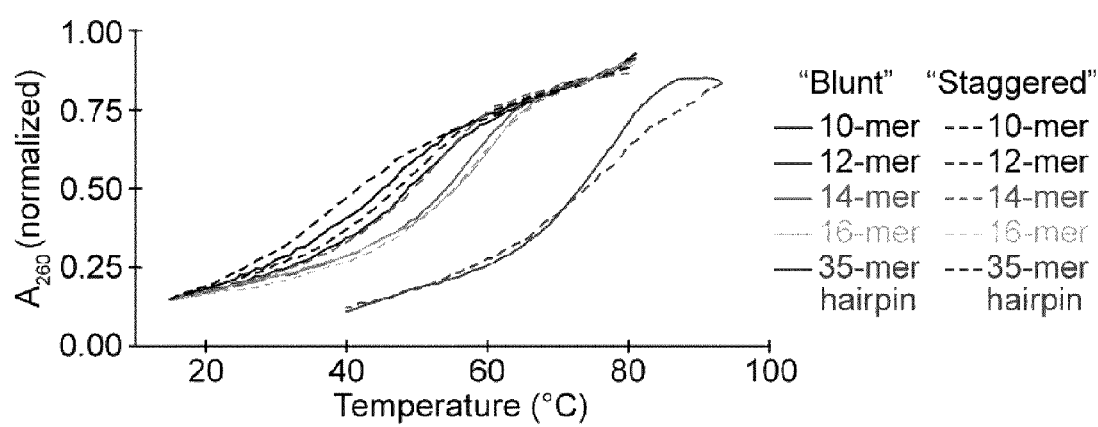
FIG. 5 illustrates representative thermal denaturation curves for MO duplexes.

To better understand how cMO structure dictates in vivo activity, we characterized the biophysical properties of each reagent. We first determined the binding energies for the ntl MO/RNA duplex, each ntl MO/inhibitor heterodimer, and various stem-loop structures. Thermal denaturation curves for the ntl MO/RNA duplex and ntl MO/inhibitor heterodimers were acquired by mixing the ntl-targeting MO with the complementary oligomers in a 1:1 ratio and measuring their temperature-dependent changes in hypochromicity at 260 nm (FIG. 5 and Tables 1-3). For these studies, we used the commercially available amine-functionalized ntl-targeting and inhibitory MO oligomers prior to their modification for cMO synthesis. The thermal denaturation curves were fit to a two-state oligomer binding model[31] to provide the corresponding $\Delta G$ values at 28° C., the standard temperature for culturing zebrafish embryos. These analyses indicated that the binding free energy for ntl MO and its complementary 25-base RNA is −28.1 kcal/mol, while binding energies for the various ntl MO/inhibitor duplexes range from −10.7 to −16.2 kcal/mol. $\Delta G$ values for intermolecular ntl MO/inhibitor complexes correlated with the length and sequence content of the inhibitory MOs, independent of the region of complementarity (corresponding to "blunt" versus "staggered" hairpins). To assess binding energies for ntl MO/inhibitor interactions within an intramolecular stem-loop, we next conducted hypochromicity measurements of "blunt" and "staggered" ntl MO hairpins. Since the 260-nm absorbance measurements would photolyze the ntl cMOs (8a-h), we synthesized two ntl MO/inhibitor hairpins (8a' and 8e') (Scheme 3) using the non-photolabile bifunctional crosslinker 2b, which was prepared from 3-(methylamino)propan-1-ol (3b) in analogy to the DMNB-based reagent 2a (Scheme 2). Derivation of the $\Delta G$ values from these thermal denaturation curves using a hairpin binding model[31] revealed that the intramolecular binding free energies of 8a' and 8e' were −5.0 and −6.9 kcal/mol, respectively (Table 4). FIG. 5 illustrates representative thermal denaturation curves for MO duplexes corresponding to ntl cMOs 8a-h (ntl-targeting and inhibitory MOs, 0.5 μM each) and non-cleavable hairpins 8a' and 8e'.

Taken together, these in vitro binding energies provide qualitative insights into how cMOs perform in vivo. Intermolecular ntl MO/inhibitor interactions with $\Delta G$ values lower than −12 kcal/mol are required for low basal activities, and "blunt" hairpins exhibit higher caging efficiencies than their "staggered" counterparts, due to their greater stabilization of the intramolecular MO/inhibitor duplex (Table 2 and FIG. 4). Surprisingly, $\Delta G$ values for the "blunt" and "staggered" ntl MO/inhibitor duplexes correlate with inhibitor length and sequence in a similar manner, yet the activities of their corresponding ntl cMOs upon photoactivation diverge. For example, the intermolecular ntl MO/inhibitor duplexes derived from "blunt" ntl cMOs 8e and 8f have $\Delta G$ values of −12.3 and −13.5 kcal/mol, respectively, and activated forms of these cMOs produce strong ntl mutant phenotypes. The other two "blunt" ntl cMOs (8g and 8h) have $\Delta G$ values of −15.5 and −16.2 kcal/mol, respectively, and both induce only partial loss-of-function phenotypes upon linker photolysis. An in vitro ntl MO/inhibitor $\Delta G$ value between −12 and −14 kcal/mol therefore represents the optimal balance of basal and induced activities for the "blunt" ntl cMOs. Yet the "staggered" ntl MOs (8a and 8b) fail to induce full ntl mutant phenotypes after uncaging, even though their corresponding ntl MO/inhibitor duplexes have $\Delta G$ values of −10.7 and −13.3 kcal/mol.

TABLE 1

Oligomer sequences

| Oligomer | Sequence | cMO |
|---|---|---|
| ntl MO[a] | GACTTGAGGCAGACATATTTCCGAT (SEQ ID NO: 1) | 8a-h, 8a', 8e', 22a-b |
| flh MO[a] | GGGAATCTGCATGGCGTCTGTTTAG (SEQ ID NO: 3) | 9 |
| heg MO[a] | GTAATCGTACTTGCAGCAGGTGACA (SEQ ID NO: 4) | 10 |
| etsrp MO[a] | CACTGAGTCCTTATTTCACTATATC (SEQ ID NO: 5) | 11 |
| spt MO[a] | GCTTGAGGTCTCTGATAGCCTGCAT (SEQ ID NO: 6) | 12 |
| ntl 10-mer "Staggered"[b] | TATGTCTGCC (SEQ ID NO: 2) | 8a, 8a' |
| ntl 12-mer "Staggered"[b] | TATGTCTGCCTC (SEQ ID NO: 7) | 8b |
| ntl 14-mer "Staggered"[b] | TATGTCTGCCTCAA (SEQ ID NO: 8) | 8c |
| ntl 16-mer "Staggered"[b] | TATGTCTGCCTCAAGT (SEQ ID NO: 9) | 8d |
| ntl 10-mer "Blunt"[b] | GCCTCAAGTC (SEQ ID NO: 10) | 8e, 8e' |

TABLE 1-continued

Oligomer sequences

| Oligomer | Sequence | cMO |
|---|---|---|
| ntl 12-mer "Blunt"[b] | CTGCCTCAAGTC (SEQ ID NO: 11) | 8f |
| ntl 14-mer "Blunt"[b] | GTCTGCCTCAAGTC (SEQ ID NO: 12) | 8g |
| ntl 16-mer "Blunt"[b] | ATGTCTGCCTCAAGTC (SEQ ID NO: 13) | 8h |
| flh 10-mer "Blunt"[b] | GCAGATTCCC (SEQ ID NO: 14) | 9 |
| heg 13-mer "Blunt"[b] | CAAGTACGATTAC (SEQ ID NO: 15) | 10 |
| Etsrp 10-mer "Blunt"[b] | GGACTCAGTG (SEQ ID NO: 16) | 11 |
| spt 10-mer "Blunt"[b] | GACCTCAAGC (SEQ ID NO: 17) | 12 |
| ntl RNA[c] | ATCGGAAATATGTCTGCCTCAAGTC (SEQ ID NO: 18) | — |
| flh RNA[c] | CTAAACAGACGCCATGCAGATTCCC (SEQ ID NO: 19) | — |
| heg RNA[c] | TGTCACCTGCTGCAAGTACGATTAC (SEQ ID NO: 20) | — |
| etsrp RNA[c] | GATATAGTGAAATAAGGACTCAGTG (SEQ ID NO: 21) | — |
| spt RNA[c] | ATGCAGGCTATCAGAGACCTCAAGC (SEQ ID NO: 22) | — |

[a]MO oligomers for translational inhibition of targeted mRNA.
[b]Inhibitory MO oligomers for modulating cMO activity.
[c]RNA oligomers for thermal denaturation studies.

TABLE 2

Thermodynamic parameters of MO/inhibitor dimers.

| Oligomer[a] | Obs. $T_m$[b] (° C.) | Pred. $T_m$[c] (° C.) | $\Delta G$[d] (kcal/mol) |
|---|---|---|---|
| 8a | 36.3 ± 0.4 | 38 | −10.7 ± 0.2 |
| 8b | 49.2 ± 1.3 | 46 | −13.3 ± 0.3 |
| 8c | 52.5 ± 1.5 | 49 | −14.1 ± 0.2 |
| 8d | 54.5 ± 0.9 | 57 | −14.7 ± 0.1 |
| 8e | 45.7 ± 0.6 | 42 | −12.3 ± 0.3 |
| 8f | 49.0 ± 0.8 | 49 | −13.5 ± 0.3 |
| 8g | 56.1 ± 0.6 | 57 | −15.5 ± 0.2 |
| 8h | 59.0 ± 0.7 | 61 | −16.2 ± 0.4 |
| 9 | 43.7 ± 1.1 | 42 | −12.5 ± 0.5 |
| 10 | 41.4 ± 1.6 | 44 | −11.4 ± 0.2 |
| 11 | 40.5 ± 1.1 | 42 | −11.7 ± 0.3 |
| 12 | 42.9 ± 1.2 | 42 | −11.9 ± 0.2 |

[a]Dimers of MO and inhibitory MO oligomers with 3' and 5' amine modifications, respectively.
[b]Melting temperature of the MO/inhibitor dimer.
[c]Predicted melting temperature from Equation 10, which is based upon the $T_m$ and $\Delta G$ values of 8a-h.
[d]Binding free energy of the dimer at 28° C. $T_m$ and $\Delta G$ values were determined from the sigmoidal fits of the thermal denaturation curves using non-self complementary algorithm in MeltWin 3.0b software.

TABLE 3

Thermodynamic parameters of MO/RNA dimers.

| Oligomer[a] | $T_m$ (° C.) | $\Delta G$[b] (kcal/mol) |
|---|---|---|
| ntl | 77.7 ± 0.8 | −28.1 ± 2.4 |
| flh | 83.4 ± 0.8 | −27.5 ± 2.1 |
| heg | 83.4 ± 0.9 | −28.4 ± 2.2 |
| etsrp | 73.9 ± 1.0 | −25.1 ± 2.8 |
| spt | 85.2 ± 1.2 | −30.0 ± 3.2 |

[a]Dimers of 25-mer MO and RNA oligomers.
[b]Binding free energy of the MO/RNA dimer at 28° C.

TABLE 4

Thermodynamic parameters of non-cleavable ntl MO hairpins.

| Oligomer | $T_m$[a] (° C.) | $\Delta G_{hairpin}$[b] (kcal/mol) |
|---|---|---|
| 8a' | 72.6 ± 2.0 | −4.9 ± 0.6 |
| 8e' | 77.8 ± 0.9 | −6.9 ± 0.5 |

[a]Melting temperature of the non-cleavable MO hairpins.
[b]Binding free energy of the hairpin at 28° C. $T_m$ and $\Delta G_{hairpin}$ values were determined from the sigmoidal fits of the thermal denaturation curves using the hairpin algorithm in MeltWin 3.0b software.

Our original solid-phase chemistry-derived ntl MO and the "staggered" cMO 8a have identical targeting and inhibitory MO sequences, suggesting that linker elements may contribute to cMO activity after uncaging. In addition, the photolysis products of ntl cMOs 8a and 8e are functionalized with linker substituents that are not present in the oligomers used in our binding energy measurements; the targeting MO liberated upon cMO activation is 3'-functionalized with a 1,2,3-triazole and an aliphatic amine, while the inhibitory oligomer is 5'-functionalized with an aliphatic chain and the DMNB-derived chromophore.

We therefore irradiated 8a and 8e with 360-nm light and then obtained thermal denaturation curves for the resulting ntl MO/inhibitor heterodimers. Analysis of the photolysis products by HPLC confirmed that the two hairpin oligonucleotides are uncaged with comparable efficacies (approximately 75% conversion), and the ΔG values for the resulting linker-functionalized ntl MO/inhibitor complexes are similar to those observed for their amine-functionalized counterparts. Unable to discern any thermodynamic differences between the intermolecular MO/inhibitor duplexes corresponding to 8a and 8e, we next interrogated whether RNA strand exchange rates might account for their divergent activities in vivo. We incubated each ntl MO/inhibitor duplex with complementary 25-base RNA for different lengths of time and resolved the resulting MO/RNA duplex by polyacrylamide gel electrophoresis. The RNA exchange rates for "staggered" and "blunt" MO/inhibitor duplexes were indistinguishable in this assay. Indeed, MO/RNA hybridization was complete in both cases within the time frame of RNA addition. Thus, the activity differences between 8a and 8e cannot be explained by in vitro MO/inhibitor thermodynamics or kinetics alone, and the two cMOs might exhibit divergent photolysis, inhibitor dissociation, or RNA exchange rates in vivo.

Figure 6:
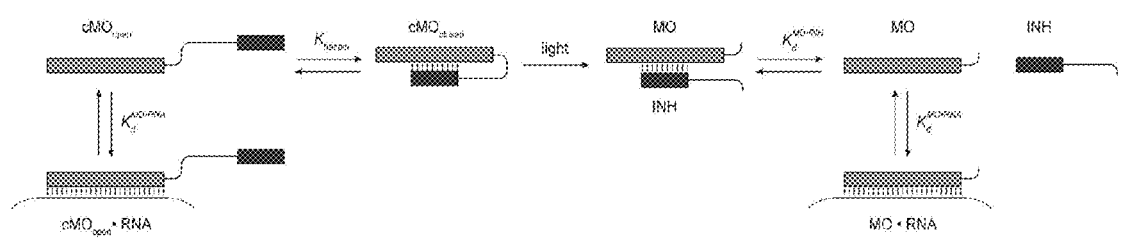
FIG. 6 is a schematic representation of cMO/RNA, MO/inhibitor (INH), and MO/RNA equilibria.

Modeling of cMO Activity in vivo A more quantitative analysis of cMO thermodynamics provides further insights into how these reagents perform in vitro and in vivo (FIG. 6 is a schematic representation of cMO/RNA, MO/inhibitor (INH), and MO/RNA equilibria). Prior to photolysis, cMOs adopt "open" and "closed" states according to the equilibrium constant $K_{hairpin}$ (Equation 1). By assuming that the total concentration of cMO prior to uncaging ($[cMO]_t$) significantly exceeds that of its RNA target ($[RNA]_t$), the basal levels of RNA bound by the non-photolyzed cMO ($[cMO_{open} \cdot RNA]/[RNA]_t$) can be described as a function of $[cMO]_t$, $K_{hairpin}$ and the dissociation constant for the MO/RNA duplex ($K_d^{MO \cdot RNA}$) (Equation 2). Upon photoactivation, the fraction of RNA now complexed with the released targeting MO is a function of $[cMO]_t$, $K_d^{MO \cdot RNA}$, and the dissociation constant for the MO/inhibitor complex ($K_d^{MO \cdot INH}$) (Equations 3 and 4). Setting $[cMO]_t$ to a value of 4.6 μM, which approximates the embryonic concentration of the ntl cMO (230 fmol/embryo, 50-nL embryonic volume at 5 hpf), and using our ntl cMO 8e data to establish ΔG values of −28.1, −12.3, and −6.9 kcal/mol for the MO/RNA duplex, intermolecular MO/inhibitor duplex, and intramolecular MO/inhibitor hairpin, respectively, predicts that essentially all ntl RNA is MO-complexed before and after cMO photolysis. These conclusions clearly deviate from the phenotypes we observed with ntl cMO 8e-injected embryos.

$$K_{hairpin} = \frac{[cMO_{open}]}{[cMO_{closed}]} \quad (Eq.\ 1)$$

$$\frac{[cMO_{open} \cdot RNA]}{[RNA]_t} = \frac{[cMO]_t K_{hairpin}}{[cMO]_t K_{hairpin} + K_{hairpin} K_d^{MO \cdot RNA} + K_d^{MO \cdot RNA}} \quad (Eq.\ 2)$$

$$[MO] = \frac{-K_d^{MO \cdot INH} + \sqrt{(K_d^{MO \cdot INH})^2 + 4 K_d^{MO \cdot INH} [cMO]_t}}{2} \quad (Eq.\ 3)$$

$$\frac{[MO \cdot RNA]}{[RNA]_t} = \frac{[MO]}{K_d^{MO \cdot RNA} + [MO]} \quad (Eq.\ 4)$$

Since these predictions do not take into account the complexity of MO and RNA interactions in live organisms, we sought to empirically derive the activity profiles of MOs in vivo. We first investigated whether the relationship between ntl RNA activity and total ntl MO concentration can still be described as a two-state equilibrium, even though the apparent equilibrium constant for in vivo MO/RNA interactions ($K_{app}^{MO \cdot RNA}$; analogous to $K_d^{MO \cdot RNA}$ in FIG. 6) would include contributions from oligonucleotide-binding proteins, RNA secondary structure, and other embryonic factors. We injected the targeting MO into one-cell stage zebrafish at doses of 0, 14, 28, 57, and 115 fmol/embryo (approximate final concentrations of 0, 0.28, 0.56, 1.1, and 2.3 μM, respectively), lysed the embryos at 10 hpf, and then detected the Ntl protein by quantitative immunoblotting (FIG. 7A). The ntl MO reduced Ntl protein levels in a dose-dependent manner that can be modeled as two-state thermodynamic interaction, with the fraction of wildtype RNA activity remaining in MO-injected embryos ($RNA_{MO}^{Act}/RNA_{WT}^{Act}$) described as a function of total MO concentration ($[MO]_t$) and $K_{app}^{MO \cdot RNA}$ (FIG. 7B and Equation 5). Through this analysis, an apparent free energy value ($\Delta G_{app}^{MO \cdot RNA}$) of −8.7 kcal/mol for embryonic ntl MO/RNA interactions was obtained.

It is important to note that this $\Delta G_{app}^{MO \cdot RNA}$ value does not reflect the actual binding constant for the ntl MO/RNA duplex in zebrafish embryos, but is instead an aggregate descriptor of MO/RNA affinity, RNA accessibility, MO/protein interactions, and the influence of other embryonic factors on MO efficacy. Indeed, the 19.4 kcal/mol difference between $\Delta G_{app}^{MO \cdot RNA}$ and the corresponding in vitro ΔG value underscores how significant these other variables can be. Our empirical data, however, suggest that this thermodynamic description can have predictive value, even though it does not explicitly consider MO and RNA interactions with other cellular components or possible kinetic contributions to in vivo function. Thus, MO-induced gene silencing can be modeled in these simplified thermodynamic terms.

To determine whether cMO activity can also be modeled in simple thermodynamic terms, we next analyzed MO/inhibitor interactions in vivo. We injected zebrafish embryos with the ntl MO (115 fmol/embryo;~2.3 μM) and various doses of the 14-base inhibitor corresponding to ntl cMO 8g (0, 150, 450, and 1350 fmol/embryo;~0, 3, 9, and 27 µM, respectively). The resulting Ntl protein levels at 10 hpf were then quantified as before (FIG. 7C). The inhibitory oligomer repressed ntl MO activity in a concentration-dependent manner that can be modeled as a three-state, competitive equilibrium involving MO, inhibitor, and RNA interactions (FIG. 7D). The fraction of wildtype RNA activity associated with each MO and inhibitor dose, $RNA_{INH, MO}^{Act}/RNA_{WT}^{Act}$, can be described as a function of the apparent equilibrium constant for MO/inhibitor interactions ($K_{app}^{MO \cdot INH}$; analogous to $K_d^{MO \cdot INH}$ in FIG. 6), the total concentration of the inhibitory oligomer ($[INH]_t$), and $[MO]_t$ (Equations 6 and 7). Through this analysis, we derived an apparent $\Delta G_{app}^{MO \cdot INH}$ value of −7.3 kcal/mol for 8g MO/inhibitor interactions. As with the $\Delta G_{app}^{MO \cdot RNA}$ value we determined for MO-dependent ntl silencing, this apparent free energy value does not reflect the actual binding constant for the ntl MO/inhibitor duplex in vivo but instead integrates other interactions between these synthetic oligonucleotides and cellular components. Since the 8.2 kcal/mol difference between $\Delta G_{app}^{MO \cdot INH}$ and the corresponding in vitro $\Delta G$ value is significantly smaller than the 19.4 kcal/mol difference we observed for MO/RNA interactions (see Table 3 and FIG. 7B), cellular factors appear to impact RNA activity to a greater extent than MO function.

$$\frac{RNA_{MO}^{Act}}{RNA_{WT}^{Act}} = \frac{K_{app}^{MO \cdot RNA}}{K_{app}^{MO \cdot RNA} + [MO]_t} \quad \text{(Eq. 5)}$$

$$\frac{RNA_{MO,INH}^{Act}}{RNA_{WT}^{Act}} = \frac{K_{app}^{MO \cdot RNA}}{K_{app}^{MO \cdot RNA} + [MO]} \quad \text{(Eq. 6)}$$

$$[MO] = \frac{-(K_{app}^{MO \cdot INH} - [MO]_t + [INH]_t) + \sqrt{(K_{app}^{MO \cdot INH} - [MO]_t + [INH]_t)^2 + 4K_{app}^{MO \cdot INH}[MO]_t}}{2} \quad \text{(Eq. 7)}$$

Figure 7:
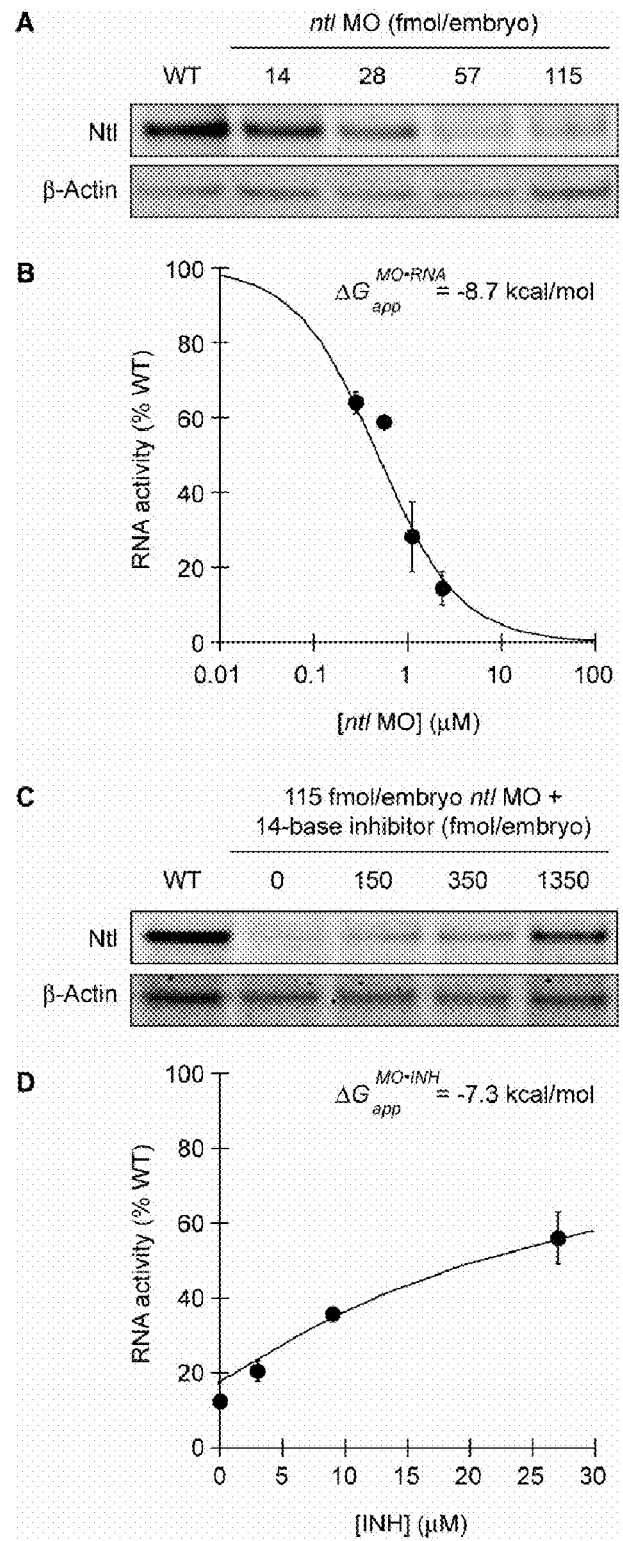
FIG. 7 illustrates ntl MO/RNA and ntl MO/inhibitor interactions in vivo. (A) Ntl protein knockdown in zebrafish embryos injected at the one-cell stage with various ntl MO doses. (B) Modeling as a two-state equilibrium (solid line), describing MO/RNA interactions in live embryos. (C) Ntl protein knockdown in embryos injected at the one-cell stage with ntl MO and various doses of the 14-base inhibitory oligomer corresponding to ntl cMO. (D) Modeling as a three-state equilibrium (solid line), describing MO, RNA, and inhibitor interactions in live embryos.

FIG. 7 illustrates ntl MO/RNA and ntl MO/inhibitor interactions in vivo. (A) Ntl protein knockdown in zebrafish embryos injected at the one-cell stage with various ntl MO doses. Ntl and β-actin levels at 10 hpf were detected by immunoblotting and quantified. (B) These data can be modeled as a two-state equilibrium (solid line), yielding an apparent free energy value ($\Delta G_{app}^{MO \cdot RNA}$=−8.7 kcal/mol) that describes MO/RNA interactions in live embryos. (C) Ntl protein knockdown in embryos injected at the one-cell stage with ntl MO (115 fmol/embryo) and various doses of the 14-base inhibitory oligomer corresponding to ntl cMO 8g. Ntl and β-actin levels at 10 hpf were detected by immunoblotting and quantified as above. (D) By modeling the 8g data in panel C as a three-state, competitive equilibrium (solid line), an aapparent free energy value ($\Delta G_{app}^{MO \cdot INH}$=−7.3 kcal/mol) that describes 8g MO/inhibitor interactions in vivo can be derived. Graphical data are the mean of triplicate samples with error bars representing the standard deviation.

To assess the validity of modeling in vivo MO, RNA, and inhibitor interactions in these simplified terms, we investigated whether the apparent $\Delta G_{app}^{MO \cdot RNA}$ and $\Delta G_{app}^{MO \cdot INH}$ values can be used to predict how cMO gene-silencing activity will be influenced by changes in inhibitor structure. As discussed above, the fraction of total RNA activity inhibited by a complementary MO and the mitigating influence of an inhibitory oligomer can be described by Equations 5-7. In the case of a cMO, $[MO]_t$ and $[INH]_t$ will be equivalent after photoactivation, and the fraction of wildtype RNA activity remaining in the presence of photoactivated cMO ($RNA_{cMO}^{Act}/RNA_{WT}^{Act}$) is therefore a function of $K_{app}^{MO \cdot RNA}$, $K_{app}^{MO \cdot INH}$, and $[cMO]_t$ (Equations 8 and 9).

$$\frac{RNA_{cMO}^{Act}}{RNA_{WT}^{Act}} = \frac{K_{app}^{MO \cdot RNA}}{K_{app}^{MO \cdot RNA} + [MO]} \quad \text{(Eq. 8)}$$

$$[MO] = \frac{-K_{app}^{MO \cdot INH} + \sqrt{(K_{app}^{MO \cdot INH})^2 + 4K_{app}^{MO \cdot INH}[cMO]_t}}{2} \quad \text{(Eq. 9)}$$

Figure 8:
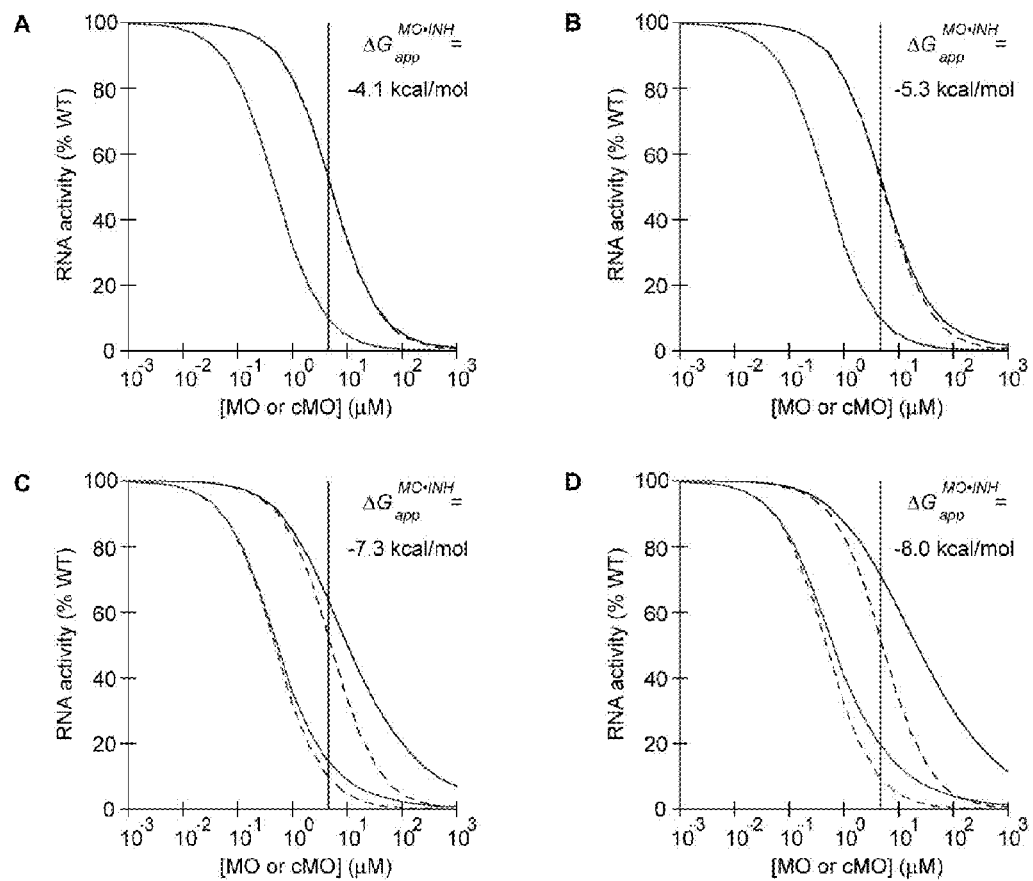
FIG. 8A-D illustrates modeling of in vivo cMO activity. Photoactivated cMOs and MOs inhibit their RNA targets with different efficacies, which diverge as MO/RNA interaction strength decreases. This divergent activity profile is exacerbated when MO/inhibitor interaction strength increases.

FIG. 8 illustrates modeling of in vivo cMO activity. Photoactivated cMOs and MOs inhibit their RNA targets with different efficacies, which diverge as MO/RNA interaction strength decreases. This divergent activity profile is exacerbated when MO/inhibitor interaction strength increases. RNA activity curves for MOs and photoactivated cMOs associated with in vivo MO/RNA interaction energies of −8.7 (red) and −7.3 (blue) kcal/mol are shown for intermolecular MO/inhibitor interaction energies estimated for the "blunt" ntl cMOs 8e (A), 8f (B), 8g (C), and 8h (D), assuming complete uncaging upon irradiation. Actual photoactivations yields in vivo are likely 50-75% (see text). Photoactivated cMO and conventional MO activity profiles are drawn as solid and dashed colored lines, respectively. The embryonic ntl cMO concentration used in our structure-activity studies (see FIG. 4) is indicated in each panel by the vertical black line.

In the case of our ntl cMO experiments shown in FIG. 4, $K_{app}^{MO \cdot RNA}$ and $[cMO]_t$ can be approximated to be 0.48 µM ($\Delta G_{app}^{MO \cdot RNA}$=−8.7 kcal/mol) and 4.6 µM, respectively. If it is assumed that "blunt" MO/inhibitor interactions generally exhibit a 8.2 kcal/mol difference between $\Delta G_{app}^{MO \cdot INH}$ and the corresponding in vitro $\Delta G$, the $K_{app}^{MO \cdot INH}$ values for MO/inhibitor interactions associated with ntl cMOs 8e, 8f, 8g, and 8h can be estimated to be 1100, 140, 50, and 1.6 µM, respectively. Using these parameters, the model described by Equations 8 and 9 predicts that ntl cMOs 8e and 8f will be similar in efficacy to the conventional ntl MO, achieving at least a 90% knockdown of Ntl protein expression levels (FIG. 8A-B; red lines). In contrast, ntl cMOs 8g and 8h are predicted to exhibit weaker efficacies at the same embryonic dose, since the inhibitory oligomer interacts more strongly with the targeting MO (FIG. 8C-D; red lines).

Our Observations in vivo Match these Predictions. Photoactivated 8e and 8f yielded the strongest mutant phenotypes of the ntl cMO configurations we tested. Moreover, the predicted efficacies of 8g and 8h are consistent with their photoinduced phenotypes and the relationship between ntl RNA activity and phenotypic class (compare FIGS. 3B, 4, 7A-B, and 8C-D), especially considering that ultraviolet light penetrance and therefore cMO uncaging efficiencies in vivo will be attenuated to some degree. Based on our in vitro uncaging results (see FIG. S1) and observed phenotypes for irradiated ntl cMO-injected embryos, we estimate that our whole-organism irradiation procedure achieves cMO photoactivation yields of 50-75%. Our model also predicts that cMO efficacy will be increasingly compromised as $\Delta G_{app}^{MO\text{-}RNA}$ increases (compare the blue and red lines in FIG. 8, which represent a ten-fold change in MO/RNA interaction strength), since the concentration of photoactivated cMO required to achieve a given level of RNA silencing increases in a manner disproportionate to that of a conventional MO. This latter issue is of particular importance since MO doses required to induce mutant phenotypes vary significantly between genes, reflecting different RNA activity thresholds for wildtype physiology and variable RNA sequence accessibilities. In addition, MO doses greater than 1000 fmol/embryo (~20 µM) are generally avoided to minimize cytotoxicity.

Taken together, these results demonstrate that cMO activity can be modeled as a competitive, three-state equilibrium, even though this approach does not explicitly consider how MO activity and RNA accessibility are influenced by cellular proteins, RNA structure, and other embryonic factors. Nor does this empirical, predictive algorithm require an accurate assessment of the actual MO/RNA or MO/inhibitor binding affinities in whole embryos. In spite of these oversimplifications, our model can still serve as a useful guide for cMO design. In particular, our findings suggest that hairpin cMOs should have apparent $\Delta G_{app}^{MO\text{-}INH}$ values of approximately −5 kcal/mol or greater, as this level of MO/inhibitor interaction in vivo will enable efficient gene-silencing upon cMO photoactivation for a broad range of targeting MO potencies. Maximizing cMO activity in this manner, however, is counterbalanced by the need to maintain the "closed" cMO hairpin state prior to photoactivation. In fact, the $\Delta G_{app}^{MO\text{-}INH}$ value of −4.1 kcal/mol predicted for ntl cMO 8e may represent the optimum thermodynamic parameter for cMO efficacy. Further attenuation of the MO/inhibitor interaction will likely yield undesirable levels of basal activity, since a small fraction of embryos injected with the ntl cMO 8e exhibited weak mutant phenotypes without irradiation (see FIG. 4).

Guidelines for Hairpin cMO Design. Having characterized the biophysical and in vivo properties of ntl cMOs prepared with our bifunctional crosslinker, we sought to establish simple guidelines for the preparation of cMOs targeting other genes and to empirically test their validity. Such design criteria would significantly advance the use of cMOs in chemical and developmental biology research, especially considering the financial and time investments associated with these studies. The disparate efficacies of the two stem-loop structures indicated that "blunt" cMO hairpins are preferable to "staggered" configurations, and within our series of "blunt" ntl cMOs 8e-h, in vitro MO/inhibitor ΔG values between −12 and −14 kcal/mol yielded an optimum balance between caged and uncaged activities. Our modeling of cMO activity in vivo further suggests that the higher MO/inhibitor ΔG value associated with ntl cMO 8e should be preferred since it will maximize inducible gene-silencing activity over a broader range of targeting MO efficacies. This binding energy corresponds to a duplex melting temperature of approximately 43° C. (see FIG. 5 and Table 2).

$$T_m^{MO} = 1.9(A \text{ or } T) + 5.7(G \text{ or } C) \qquad \text{(Eq. 10)}$$

$$\Delta G = -0.25\, T_m^{MO} - 1.4 \qquad \text{(Eq. 11)}$$

To facilitate the design of thermodynamically equivalent cMOs against other genes, we first determined the relationship between MO duplex sequence and thermal stability. By multiple regression analysis of the ntl MO/inhibitor pairs listed in Table 2, we determined that the thermal stability of MO duplexes ($T_m^{MO}$) correlates with sequence content according to Equation 10, which can be empirically related to its in vitro ΔG value (kcal/mol; 28° C.) by Equation 11. Using this equation, one can then identify an appropriate inhibitor for a given targeting MO, which ideally would generate a "blunt" hairpin and have a predicted duplex melting temperature approaching 43° C. This empirically derived algorithm will be most accurate with MO duplexes similar in length to those in this study, since it does not take into account the contribution of nearest neighbor effects.

Figure 9:
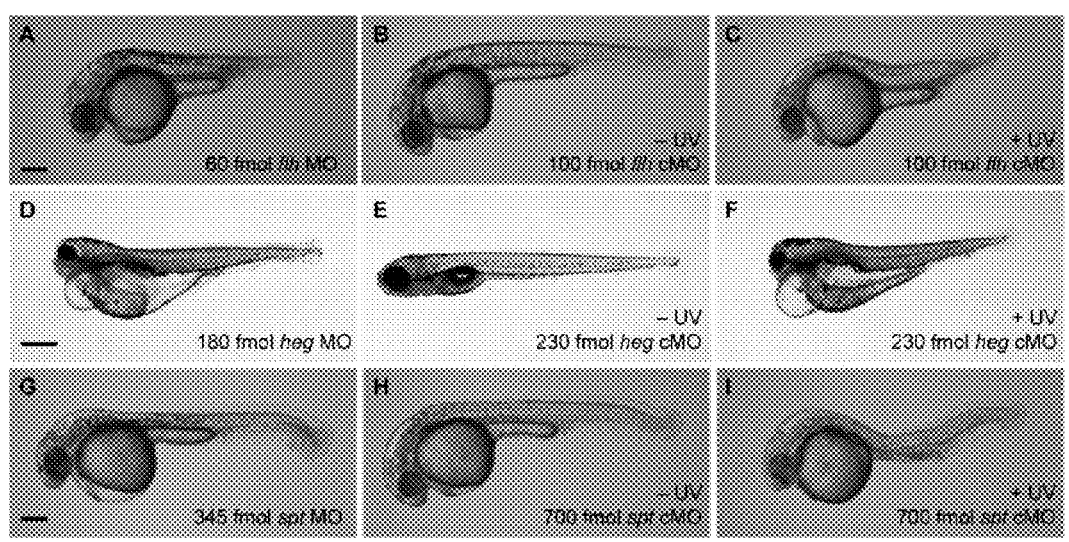
FIG. 9A-I illustrates an evaluation of flh, heg, and spt cMO activities in vivo.

We next tested the validity of our design criteria by targeting four other zebrafish genes: flh, heg, etsrp, and spadetail (spt). The flh homeobox transcription factor is co-expressed with ntl in the zebrafish mesoderm, and loss of flh expression also causes ablation of the notochord. However, mesodermal progenitors normally fated to become the notochord do not transform into medial floor plate cells in flh mutants; rather, these populations differentiate into ectopic muscle to created fused somites. Since no flh-targeting MO had yet been described, we first identified a flh-blocking oligonucleotide (5'-GGGAATCTGCATGGCGTCTGTTTAG-3') (SEQ ID NO:3) and demonstrated its efficacy in zebrafish embryos (FIG. 9A). This antisense reagent is a potent inhibitor of flh function, and a dose of 60 fmol/embryo (~1.2 µM) is sufficient to cause replacement of the notochord with axial muscle cells in 1-dpf zebrafish (89%, n=19). Based on our cMO design criteria, we synthesized a hairpin flh cMO (9) using crosslinker 2a and a 5'-GCAGATTCCC-3' (SEQ ID NO:14) oligomer as the MO inhibitor (Tables 1-3). Wildtype zebrafish were injected at the one-cell stage with 9 at a dose of 100 fmol/embryo (~2 µM) and either globally irradiated with 360-nm light for 10 seconds at the 2 hpf or cultured in the dark. As expected, the majority of non-irradiated flh cMO-injected embryos developed normally (89%, n=28), while the irradiated embryos lacked a notochord and had fused somites (100%, n=11), matching the mutant phenotype (FIG. 9, B-C).

FIG. 9 illustrates an evaluation of flh, heg, and spt cMO activities in vivo. (A) Embryos injected with a conventional flh MO recapitulate flh mutant phenotypes, including notochord ablation and somite fusion through the trunk midline. (B-C) Embryos injected with flh cMO 9 exhibit flh mutant phenotypes upon photoactivation. (D) Embryos injected with a conventional heg MO recapitulate heg mutant phenotypes, including enlarged heart chambers, no blood circulation, and cardiac edema. (E-F) Embryos injected with heg cMO 10 exhibit heg mutant phenotypes upon photoactivation. (G) Embryos injected with a conventional spt MO recapitulated spt mutant phenotypes, including a loss of trunk somitic tissue and mislocalized mesodermal progenitors in the posterior ("spadetail" morphology). (H-I) Embryos injected with spt cMO 12 exhibit partial spt mutant phenotypes upon photoactivation. Non-specific toxicity is also observed (data not shown). Developmental stages: A-C and G-I, 1-dpf; D-F, 4-dpf. Scale bars: A-C and G-I, 200 μm; D-F, 400 μm.

The transmembrane protein heg is expressed in the endocardium during embryogenesis, mediating a signal that is required for concentric growth of the heart. Embryos lacking heg function exhibit abnormally large heart chambers with walls that are only one-cell thick and therefore incapable of sustaining blood circulation. These defects are apparent by 2 dpf and can be recapitulated with the heg-targeting MO (5'-GTAATCGTACTTGCAGCAGGTGACA-3') (SEQ ID NO:4) at doses of 180 fmol/embryo (~3.6 μM) or higher. By 4 dpf, heg mutants and morphants exhibit severe cardiac edema (FIG. 9D). To generate a heg cMO (10), we conjugated the targeting MO to an inhibitory oligomer 5'-CAAGTAC-GATTAC-3' (SEQ ID NO:15) using crosslinker 2a (Tables 1-3). We then injected wildtype zebrafish embryos with 10 at the one-cell stage (230 fmol/embryo; ~4.6 μM) and either irradiated the embryos with 360-nm light at 2 hpf or cultured them in the dark. By 4 dpf the irradiated embryos exhibited no blood circulation and cardiac edema (89%, n=9), while the non-irradiated zebrafish had normal cardiac patterning and function (93%, n=27) (FIG. 9, E-F).

The etsrp transcription factor is expressed in the lateral mesoderm during early somitogenesis and then in vascular endothelial cells of the axial, head, and intersomitic vessels.[26] It is believed that these early etsrp-expressing cells are endothelial precursors, and etsrp mutants or embryos injected with an etsrp-blocking MO (5'-CACTGAGTCCTTATTTCAC-TATATC-3') (SEQ ID NO:5) exhibit disrupted blood vessel formation and lack circulation.[26] MO doses of 115 fmol/embryo (~2.3 μM) or higher are sufficient to induce a fully penetrant mutant phenotype (data not shown). We therefore synthesized a hairpin etsrp cMO (11) containing a 5'-GGACTCAGTG-3' (SEQ ID NO:16) inhibitory oligomer and injected it into wildtype zebrafish at the one-cell stage (230 fmol/embryo; ~4.6 μM) (Tables 1-3). Embryos then irradiated with 360-nm light for 10 seconds at 3 hpf had limited or no blood circulation by 2.5 dpf (100%, n=12), but most etsrp cMO-injected embryos cultured in the dark exhibited normal blood flow (87%, n=15).

A cMO targeting spt, was designed and synthesized which is another mesodermal T-box transcription factor. The ntl and spt genes are expressed in overlapping domains during early embryogenesis, and then become restricted to the axial and paraxial mesoderm, respectively. Cells with ntl function become the notochord, while the spt-expressing cells contribute to the skeletal muscle in the flanking somites. A loss of spt function therefore causes a severe deficit in trunk somitic mesoderm, as well as a gross mislocalization of the corresponding progenitor cells to posterior regions (hence the "spadetail" name). These phenotypes can be recapitulated with a spt-targeting MO 12 (5'-GCTTGAGGTCTCTGAT-AGCCTGCAT-3') (SEQ ID NO:6) at doses of 345 fmol/embryo (~6.9 μM) or higher (61%, n=23) (FIG. 9G). As with the other cMOs described above, we prepared the corresponding spt cMO hairpin using crosslinker 2a and the inhibitory oligomer 5'-GACCTCMGC-3' (SEQ ID NO:17) (Tables 1-3). Wildtype embryos were injected at the one-cell stage with 12, and a subset was globally irradiated with 360-nm light for 10 seconds at 2 hpf. The majority of embryos cultured in the dark developed normally (87%, n=24). Zebrafish injected with a dose of 700 fmol/embryo (~14 μM) exhibited a loss of trunk mesoderm upon cMO photoactivation but not posteriorly mislocalized progenitor cells (31%, n=16), as well as non-specific developmental defects due to general MO toxicity (62%, n=16) (FIG. 9, H-I). These phenotypes indicate that the photoactivated spt cMO 12 is not able to fully recapitulate the activity of the conventional MO and that this reagent also exhibits greater non-specific toxicity. Thus, although our design criteria were successful for cMOs targeting ntl, flh, heg, and etsrp, in some situations there will be unforeseen MO or inhibitor interactions with embryonic factors that reduce the cMO efficacy. In the case of the spt cMO, one possibility is that a 700 fmol/embryo dose of the 35-base reagent approaches the toxicity level of a 1000 fmol/embryo dose of the conventional 25-base MO.

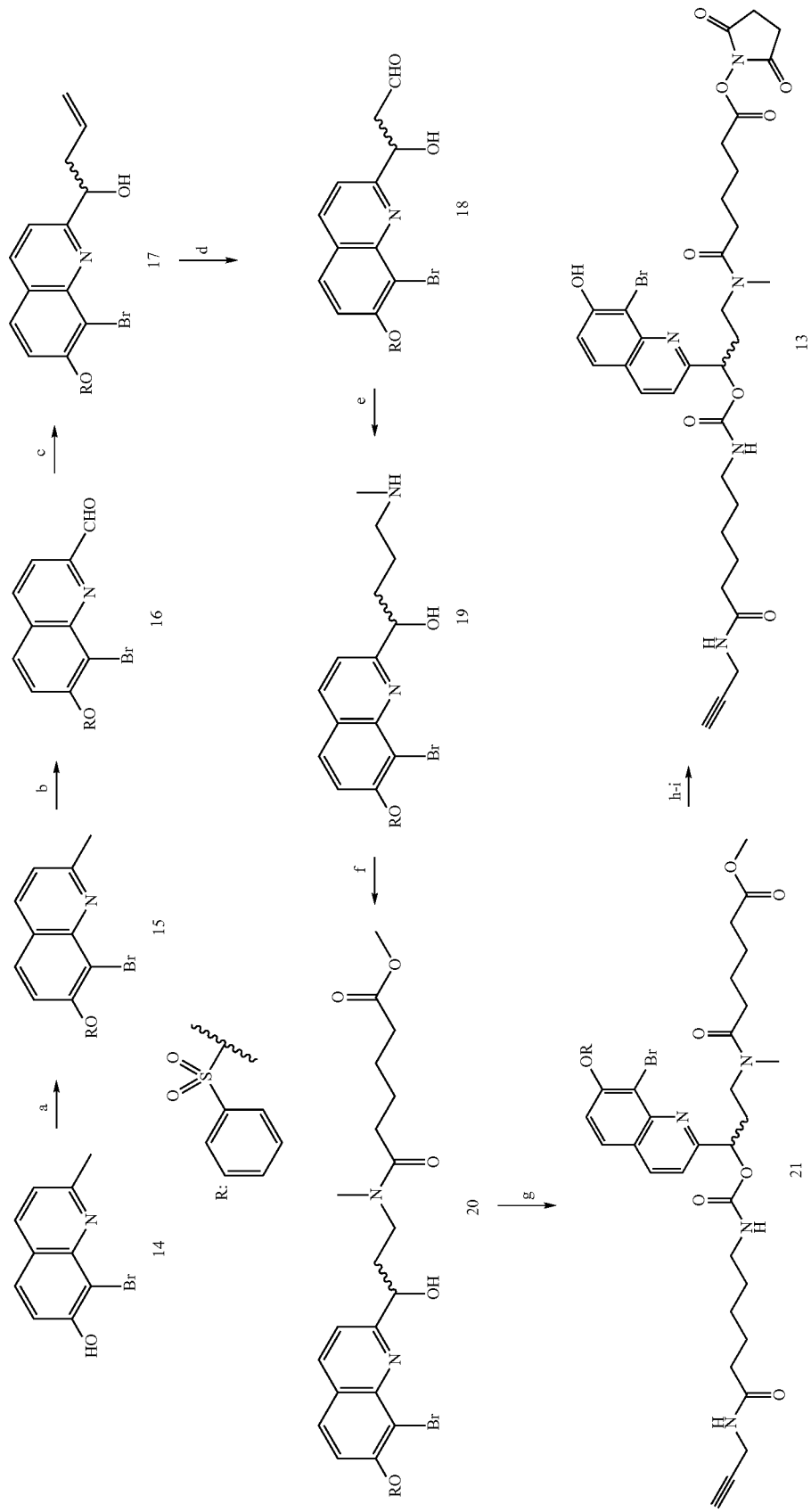

Scheme 4. Synthesis of bifunctional BHQ linker 13.

Reagents and conditions: (a) benzenesulfonyl chloride, DIPEA, CH$_2$Cl$_2$, 97%; (b) SeO$_2$, dioxane, 80° C., 91%; (c) In powder, allyl bromide, NH$_4$Cl (aq.), THF, 96%; (d) K$_2$OsO$_4$•2H$_2$O, lutidine, dioxane, H$_2$O; then NaIO$_4$, 75%; (e) methyl amine (aq.), NaBH(OAc)$_3$, MeOH, H$_2$O, 81%; (f) methyl adipoyl chloride, DIPEA, CH$_2$Cl$_2$, 59%; (g) carbonyl diimidazole, DMF; then 6-amino-N-(prop-2-ynyl)hexanamide, DIPEA, DMF, 81%; (h)0.2 N NaOH (aq.), THF, MeOH, 82%; (I) N-hydroxysuccinimide, EDCI, DMF, 48%.

Development of a BHQ-Based cMO for Two-Photon Activation. We investigated the ability of our hairpin cMO design to incorporate other photocleavable groups. While nitrobenzyl-based chromophores such as the DMNB group in our ntl, flh, heg, etsrp, and spt cMOs have been widely used in biological applications, the ultraviolet light required for their photolysis is potentially damaging and is difficult to restrict in three-dimensional space. Two-photon excitation typically uses wavelengths greater than 700 nm and affords greater spatial resolution, but the DMNB group and most other caging moieties have small two-photon cross sections and are therefore inefficiently cleaved under these conditions. Two notable exceptions are the bromohydroxycoumarin (BHC) and bromohydroxyquinoline (BHQ) groups. Since the low fluorescence of BHQ chromophores makes them particularly useful for biological applications, we designed a BHQ-based bifunctional crosslinker (13, Scheme 4) for the preparation of cMOs. As with our DMNB-based linker 2a, this two-photon-sensitive linker incorporates an N-hydroxysuccinimide ester and a terminal alkyne to enable orthogonal coupling to appropriately modified MO oligomers.

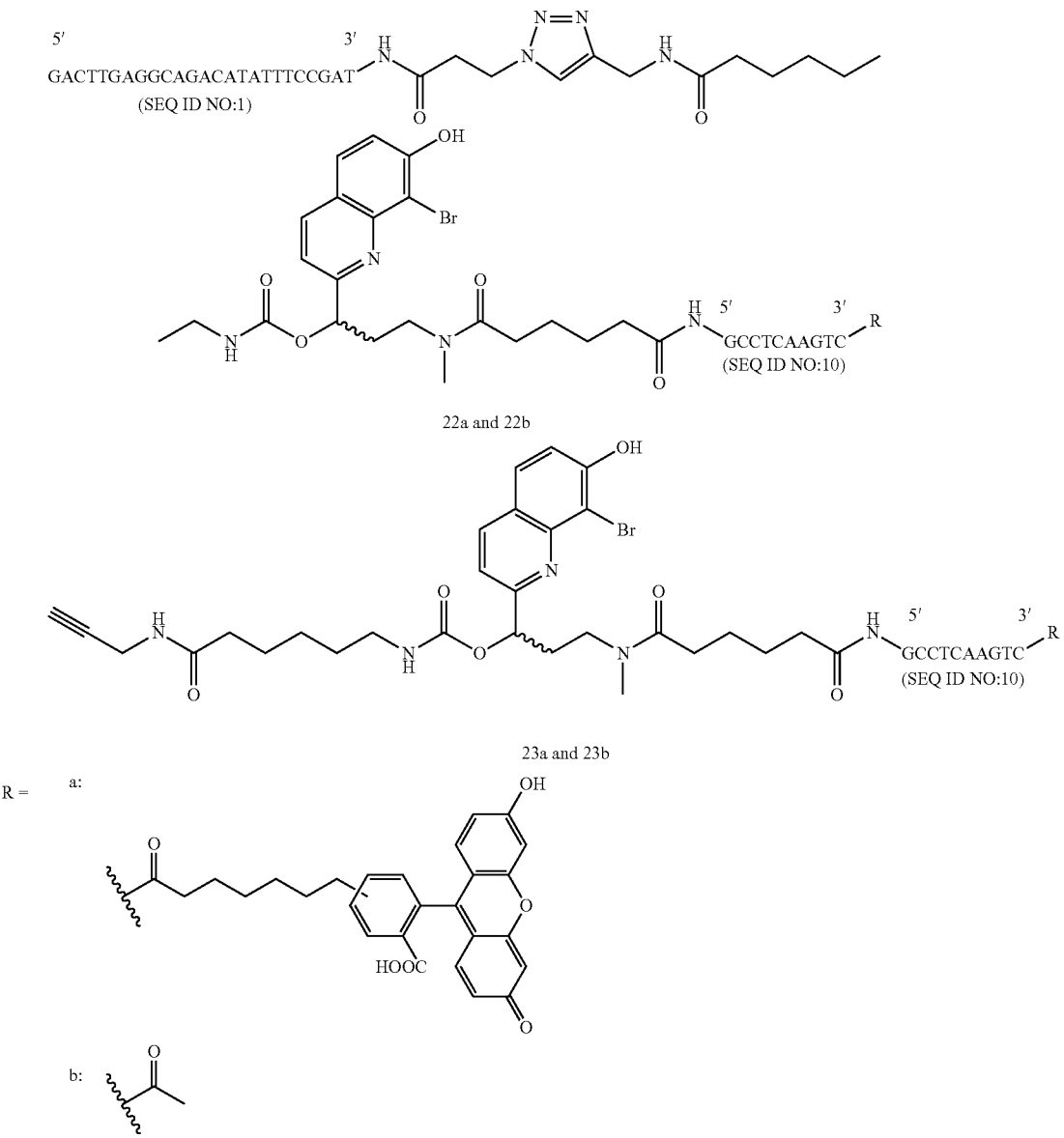

Schematic representation of BHQ-based ntl cMOs 22a and 22b and their corresponding precursors 23a and 23b.

To synthesize crosslinker 13, we first prepared BHQ derivative 14 as previously described[27] and protected its phenolic hydroxyl with a benzenesulfonyl moiety to give 15. The 2-methyl group of 15 was then oxidized with selenium dioxide, and the resulting aldehyde 16 was allylated to give alcohol 17. Oxidative cleavage of 17 yielded aldehyde 18,[35] which was reductively aminated with aqueous methylamine in the presence of $NaBH(OAc)_3$ to give the amino alcohol intermediate 19. In analogy to Scheme 2, compound 19 was acylated to form the amide 20, and 1,1'-carbonyl diimidazole-mediated coupling of this product with 6-amino-N-(prop-2-ynyl)hexanamide afforded the carbamate 21. Phenol deprotection and ester saponification of 21 were simultaneously accomplished with 0.2 N NaOH to give an acid intermediate, which was re-esterified with N-hydroxysuccinimide in the presence of 1-ethyl-3-(3'-dimethylaminopropyl)carbodiimide to give the BHQ crosslinker 13. The bifunctional linker was then used to assemble fluorescein-conjugated and nonfluorescent ntl cMOs (22a and 22b, respectively; Chart 3) using the corresponding inhibitory oligomers (23a and 23b), which are analogous to that in the optimum DMNB-containing ntl cMO 8e (FIG. 4 and Table 1). Since the BHQ group has not been used previously with carbamates and other BHQ-caged compounds have not been tested in cultured cells or live organisms, we first determined whether the BHQ carbamate is stable in vivo and can be efficiently photolyzed. We injected ntl cMO 22a into wildtype zebrafish embryos at the one-cell stage (230 fmol/embryo) and irradiated a subset of them with 360-nm light for 10 seconds at 3 hpf. The embryos were then cultured for another day and scored according to the four phenotypic classes described above. As we hoped, the BHQ-based ntl cMO exhibited activities essentially identical to that of the DMNB-based reagent 8e; embryos injected with this reagent developed normally when cultured in the dark but displayed a ntl phenotype upon irradiation.

Figure 10:
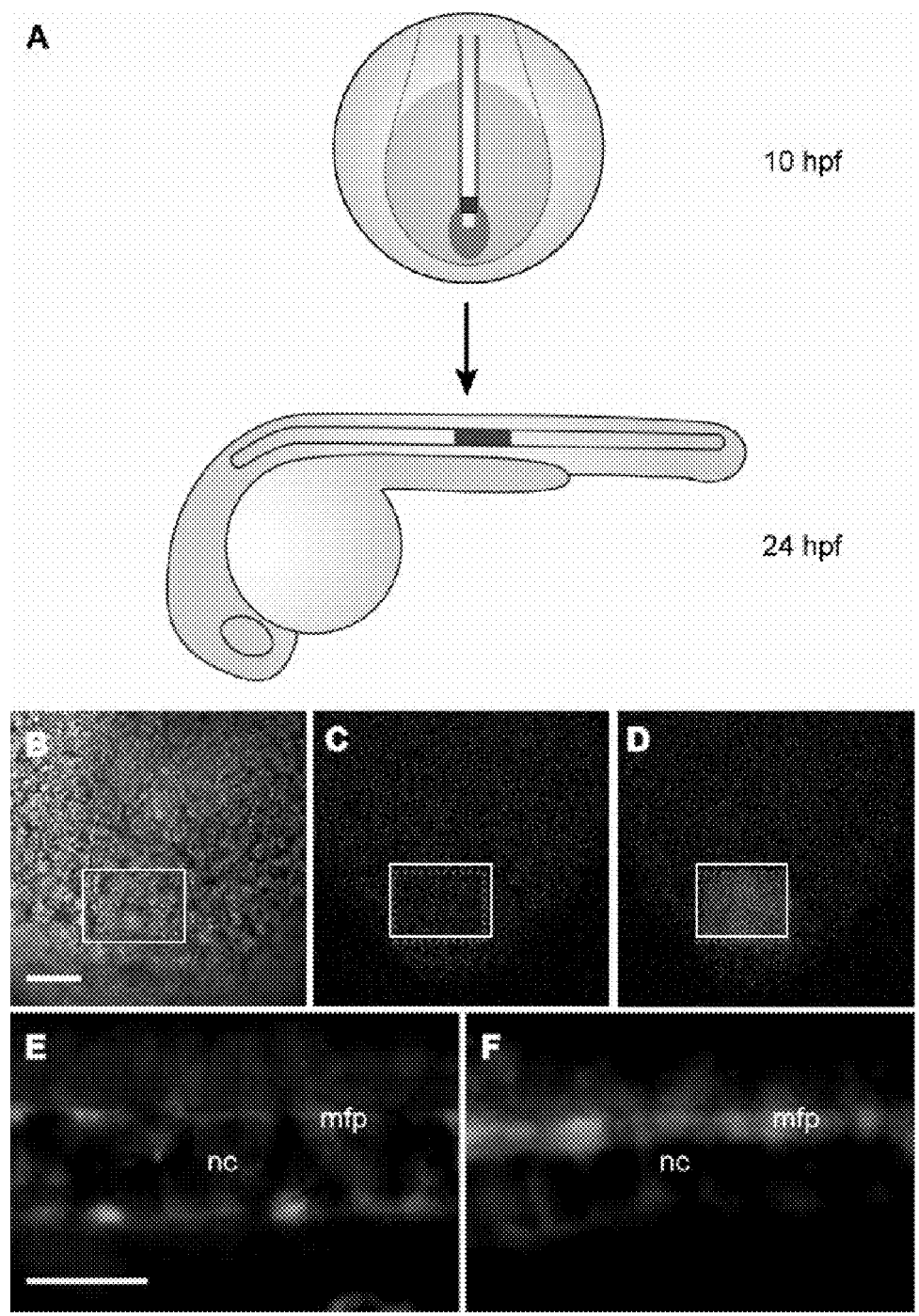
FIG. 10A-F illustrates two-photon uncaging of the BHQ-based ntl cMO in vivo.

We then examined whether the BHQ-based ntl cMO 22b could be activated in targeted regions of the zebrafish embryo using two-photon excitation. These experiments followed studies conducted previously by our laboratory, in which we uncaged a DMNB-based ntl cMO in a subset of mesodermal progenitor cells, selectively inducing them to differentiate into medial floor plate cells rather than the notochord.[7] To identify the irradiated cells in this earlier investigation, we co-injected the zebrafish embryos with mRNA encoding Kaede fluorescent protein, which undergoes a green-to-red photoconversion with one-photon excitation. Because Kaede is inefficiently converted by two-photon excitation, we utilized a caged coumarin fluorophore conjugated to dextran (dextran-HCC-NPE) as a cell-autonomous photoactivatable tracer. This new class of caged coumarins is highly sensitive to two-photon irradiation, and dextran-HCC-NPE has demonstrated efficacy in vivo. We injected dextran-HCC-NPE into one-cell stage embryos with either the BHQ-based ntl cMO 22b or the BHQ-conjugated inhibitory oligomer 23b. A 80 μm×60 μm×50 μm region of the posterior, axial mesoderm at the end of gastrulation was then subjected to two-photon irradiation for 2 minutes (FIG. 10A-D). Normally these cells will differentiate into vacuolated notochord cells by 1 dpf, and the embryos injected with the coumarin tracer and BHQ-functionalized ntl MO inhibitor 23b contained a cluster of blue fluorescent notochord cells toward the end of the yolk extension (FIGS. 10, A and E). In contrast, embryos injected with both the photoactivatable tracer and ntl cMO 22b exhibited medial floor plate cells with blue fluorescence and few, if any, fluorescently labeled notochord cells (FIG. 10F). These observations confirm the sensitivity of the BHQ-based reagent to two-photon photolysis, and illustrate the versatility of the hairpin cMO architecture.

FIG. 10 illustrates two-photon uncaging of the BHQ-based ntl cMO in vivo. (A) Schematic representation of embryos injected with the dextran-HCC-NPE photoactivatable tracer and then two-photon irradiated within the posterior axial mesoderm at the 10-hpf stage (red square, dorsal view). By 1 dpf, these irradiated cells normally differentiate into vacuolated notochord cells (red rectangle, lateral view) toward the end of the yolk extension. (B) Infrared gradient contrast image of the posterior axial mesoderm with the targeted irradiation area indicated by the dashed red box (dorsal view). (C) Fluorescent image of the same region prior to irradiation (excitation: 820 nm; emission: 525/70 nm). (D) Fluorescent image post irradiation (same conditions as in C). (E) Embryos injected with the dextran-HCC-NPE and oligomer 23b contained a cluster of blue fluorescent notochord (nc) cells by 1 dpf (lateral view; excitation: 436/20 nm; emission: 480/40 nm). (F) Embryos injected with dextran-HCC-NPE and ntl cMO 22b exhibited medial floor plate (mfp) cells with blue fluorescence and few fluorescently labeled notochord cells (same conditions as in E). Scale bars: 50 μm.

Example 2

A Simplified Synthetic Strategy for Caged Morpholinos. The results described above validate the photoactivation strategy and chemical procedures. The caged morpholino synthesis was then further optimized. In the original synthetic methods, the 5'- and 3'-modified inhibitory morpholino decamer was prepared by solid-phase synthesis, requiring the generation of each morpholino base as an activated monomer. This time-consuming and labor-intensive approach was necessary because 5'-modifiable morpholino oligomers were not commercially available at the time of these studies. In addition, the final purification of the caged morpholino involved ion-exchange HPLC, which requires equipment and columns that are not standard in many biological laboratories.

Figure 2:
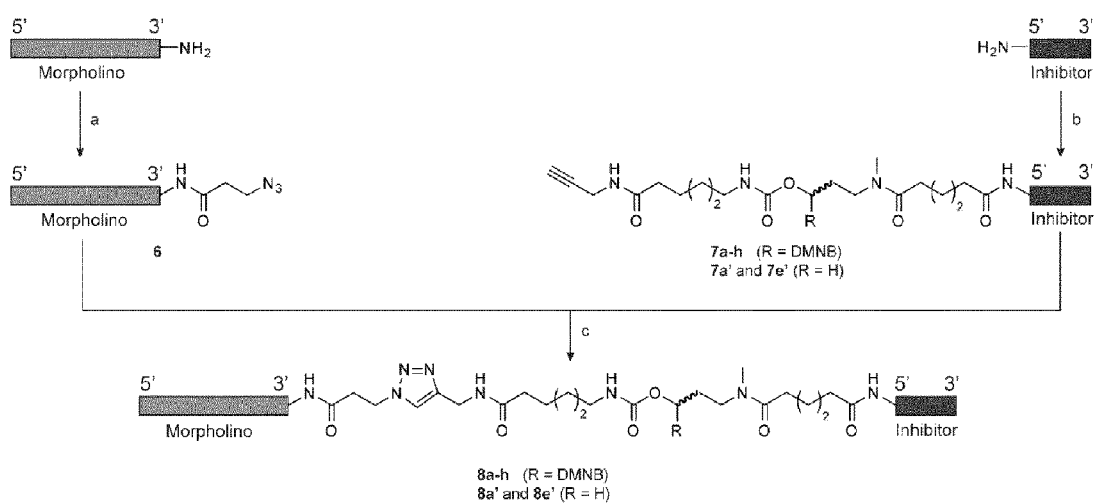
FIG. 2 illustrates a simplified procedure for caged morpholino synthesis from commercially available oligomers.

Thus, a new synthetic strategy was developed that takes advantage of the recent commercial availability of 5'-amine morpholinos. Rather than incorporating the photocleavable linker as a building block in solid-phase synthesis, this moiety was conjugated onto the complete inhibitory oligomer in a single step (FIGS. 1 and 2). Coupling of the linker-modified inhibitor to the conventional 25-base morpholino derivatized with an azide is then achieved in a second reaction to yield the caged reagent.

These changes in our synthetic procedure enabled us to rapidly prepare caged reagents that target other genes, such as spt, tbx6, and flh. These modified protocols will also significantly simplify the preparation of caged morpholinos by other laboratories.

General Synthetic Procedures.

All reactions were carried out in flame-dried glassware under an argon atmosphere using commercial reagents without further purification, unless otherwise indicated. Reactions were magnetically stirred and monitored by thin layer chromatography (TLC), using glass-backed silica gel $60_{F254}$ (Merck, 250 μm thickness). Yields refer to chromatographically and spectroscopically pure compounds unless otherwise stated. $SiO_2$ chromatography was carried out with EM Science silica gel (60 U, 70-230 mesh) as a stationary phase. $^1$H NMR and $^{13}$C NMR spectra were acquired on Varian 300, 400, and 500 MHz spectrometers and standardized to the NMR solvent peak. Electrospray (ESI) mass spectra were obtained using a Micromass ZQ single quadrupole liquid chromatography-mass spectrometer (LC-MS) and a Micromass Q-TOF hybrid quadrupole LCMS. Detailed synthetic procedures and structural characterization data are included as Supporting Information.

Representative Procedure for MO Inhibitor Synthesis (7e). A MO oligomer (5'-GCCTCAAGTC-3') (SEQ ID NO:10) with 5' amine and 3' fluorescein modifications was purchased from Gene-Tools, LLC and used without further purification. This oligomer (100 nmol) was dissolved in borate buffer (0.1 M $Na_2B_4O_7$, pH 8.5, 100 μL) and combined with linker 2a (0.76 mg, 1.5 μmol) in DMSO (15 μL). The reaction was shaken overnight in the dark and then lyophilized to dryness. The resulting yellow gum was dissolved in water (0.5 mL), washed three times with $CHCl_3$ (0.5 mL) and diluted to 1.5 mL with water. The yellow solution was loaded onto Toyopearl Super-Q resin (400 μL), washed three times with wash solution (aq. 2.5 mM $Na_2B_4O_7$, pH 8.5, 50% ACN) and two times with water. Fluoresceinated oligomers were eluted from the resin with 600 μL of aq. 5% HOAc/50% ACN, washed three times with $CHCl_3$ (0.6 mL) and neutralized with aq. 10% $NH_4OH$ (0.3 mL). Solvent was removed in vacuo and the remaining $NH_4OAc$ was removed by repeated aqueous solubilization and lyophilization, affording 7e as a yellow solid (70 nmol, 70%). MS-ESI (m/z): [M+H]+ calculated for 7e $C_{184}H_{264}N_{69}O_{61}P_{10}$, 4728; found, 4728.

Representative procedure for cMO synthesis (8e). The inhibitory oligomer 7e (50 nmol) and azide-functionalized ntl MO[7] 6 (50 nmol) were dissolved in phosphate buffer ($KH_2PO_4$, pH 8.0, 230 μL). To this mixture was added sodium ascorbate (99.0 βg, 500 nmol) in 25 μL of water, followed by TBTA (265 μg, 500 nmol), and CuI (95.2 μg, 500 nmol) in 50 μL of DMSO. The reaction mixture was briefly sonicated and stirred overnight at room temperature in the dark. Precipitate was removed from reaction mixture by centrifugation, and the supernatant was split and desalted over two Zeba Desalt size-exclusion columns (Pierce) according to the manufacturer's instructions. The desired product was purified from the reaction mixture by adjusting the solution pH to 11.5 with aq. 1 M NaOH and loading it onto a DNAPac PA-100 ion-exchange HPLC column (Dionex, 9 mm×250 mm). Aqueous running buffers were A: 0.02 M NaOH, 1% ACN; B: 0.375 M $NaClO_4$ in 0.02 M NaOH and 1% ACN. A step-wise gradient was used to separate the product and starting materials, with specific conditions determined by column capacity. A representative purification gradient is: 7 to 19% B in 5 min, 19 to 22% B in 10 min, 22 to 50% B in 1 min, and 50% B for 9 min (flow rate of 4 mL/min). Elution fractions were collected with the UV-VIS flow-cell lamp turned off to prevent photolysis. Fractions (1 mL) were collected every 15 sec, and buffered with aq. 1 M $NH_4OAc$, pH 5.0 (40 μL). The fractions containing fluoresceinated product were combined, and desalted over a Zeba size-exclusion column. Eluent volume was reduced in vacuo to 50 μL and the MOs were precipitated with acetone (400 μL). After centrifugation, the supernatant was discarded and the MO pellet was washed with ACN (100 μL) and briefly lyophilized, affording 8e as a yellow solid (7 nmol, 14%). [M+H]+ calculated for 8e $C_{488}H_{737}N_{219}O_{164}P_{35}$, 13379; found, 13380.

Synthesis of bi-Functional Photocleavable Cross-Linker.

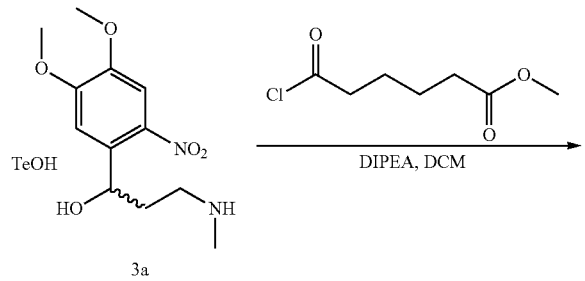

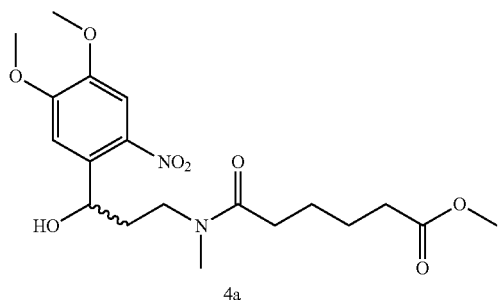

Methyl 6-((3-(4,5-dimethoxy-2-nitrophenyl)-3-hydroxypropyl)(methyl)amino)-6-oxohexan-oate (4a). 1-(4,5-Dimethoxy-2-nitro-phenyl)-3-methylamino-propan-1-ol tosylate salt 3a[1] (600 mg, 1.35 mmol) and N,N-diisopropylethylamine (476 μL, 2.7 mmol) were dissolved in anhydrous DCM (5 mL), and the solution was cooled to 0° C. Methyl adipoyl chloride (241 mg, 1.35 mmol) was added over 10 min, and the reaction mixture was stirred for 6 h at room temperature under nitrogen. After the reaction solvent was removed in vacuo, the resulting residue was dissolved in EtOAc, washed twice with saturated aq. $NaHCO_3$ and then dried over anhydrous $Na_2SO_4$. Solvent was removed in vacuo, and the residue was purified by $SiO_2$ column chromatography (EtOAc) to yield 4a as a yellow oil (480 mg, 86%). $^1H$ NMR (500 MHz, $CDCl_3$) δ 7.62 (s, 1H), 7.42 (s, 1H), 5.21 (d, 1H, J=3.5 Hz), 5.15, (d, 1H, J=7.0 Hz), 4.51 (m, 1H), 4.02 (s, 3H), 3.94 (s, 3H), 3.66 (s, 3H), 3.15 (s, 3H), 2.84 (m, 1H), 2.46 (m, 2H), 2.36 (m, 2H), 2.19 (m, 2H), 1.72 (m, 4H), 1.49 (m, 1H). $^{13}C$ NMR (125 MHz, $CDCl_3$) δ174.93, 173.94, 154.09, 147.47, 138.70, 136.20, 108.96, 107.58, 65.28, 56.57, 56.37, 51.65, 44.66, 36.09, 35.58, 33.86, 33.06, 24.70, 24.64. MS-ESI (m/z): [M+H]+ calculated for $C_{19}H_{29}N_2O_8$, 413.2; found, 413.2. [M+Na]+ calculated for $C_{19}H_{28}N_2NaO_8$, 435.2; found, 435.2.

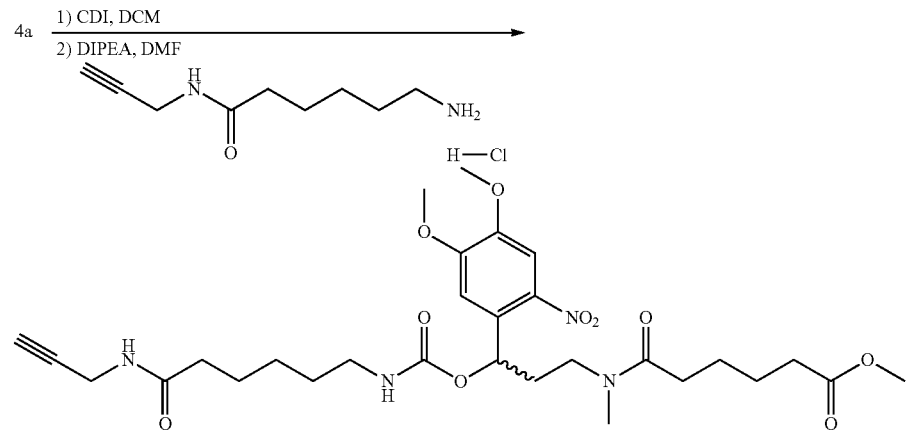

Methyl 14-(4,5-dimethoxy-2-nitrophenyl)-17-methyl-5, 12, 18-trioxo-13-oxa-4, 11,1 7-triaza-tricos-1-yn-23-oate (5a). Compound 4a (150 mg, 0.364 mmol) was dissolved in anhydrous DCM (1 mL) and added to 1,1'-carbonyl diimidazole (145 mg, 0.894 mmol) in anhydrous DCM (1.5 mL). The reaction mixture was stirred for 4 h at room temperature under nitrogen, diluted with DCM, washed two times with water, and dried over anhydrous MgSO$_4$. Solvent was removed in vacuo to yield crude imidazole carbamate as a yellow gum (164 mg, 66%). MS-ESI (m/z): [M+H]$^+$ calculated for $C_{23}H_{31}N_4O_9$, 507.2; found, 507.0. Without further purification, the imidazole carbamate (121 mg, 0.239 mmol) was dissolved in anhydrous DCM (1.5 mL) and N,N-diisopropylethylamine (330 μL, 1.91 mmol). To this mixture was added 6-oxo-6-(prop-2-ynylamino)hexan-1-aminium hydrochloride salt[2] (145 mg, 0.708 mmol) in anhydrous DMF (1.4 mL). The reaction mixture was stirred overnight at room temperature under nitrogen. Solvent was then removed in vacuo, and the crude material was re-dissolved in toluene and evaporated to dryness again. The resulting yellow gum was then dissolved in CHCl$_3$, washed once with 1 N HCl, washed once with 5% saturated aq. NaHCO$_3$, washed once with brine, and dried over anhydrous MgSO$_4$. Solvent was removed in vacuo, and the residue was purified by SiO$_2$ column chromatography (CHCl$_3$/acetone, stepwise gradient from 4/1 to 1/1) to yield 5a as a thick yellow gum (126 mg, 57% from 4a). $^1$H NMR (500 MHz, CDCl$_3$) δ 7.63 (m, 1H), 6.98 (m, 1H), 6.24–5.88 (m, 2H), 5.24–5.00 (m, 1H), 4.03 (m, 1H), 3.98–3.93 (m, 6H), 3.67 (m, 3H), 3.56 (m, 1H), 3.16 (m, 1H), 3.06–2.95 (m, 3H), 2.34 (m, 3H), 2.17 (m, 4H), 1.95 (m, 1H), 1.67 (m, 6H), 1.50 (m, 2H), 1.34 (m, 2H). $^{13}$C NMR (75 MHz, DMSO-d$^6$) δ 172.53, 171.01, 154.59, 153.18, 147.60, 139.35, 131.53, 124.28, 109.01, 108.09, 80.88, 78.57, 78.30, 71.59, 68.34, 66.48, 55.93, 50.35, 34.57, 34.50, 32.76, 29.99, 28.57, 27.33, 25.38, 24.57, 24.16, 23.73, 23.68.

MS-ESI (m/z): [M+H]$^+$ calculated for $C_{29}H_{43}N_4O_{10}$, 607.3; found, 607.3. [M+Na]$^+$ calculated for $C_{29}H_{42}N_4NaO_{10}$, 629.3; found, 629.3.

2,5-Dioxopyrrolidin-1-yl 14-(4,5-dimethoxy-2-nitrophenyl)-17-methyl-5, 12, 18-trioxo-13-oxa 4, 11, 17-triazatricos-1-yn-23-oate (2a). Compound 5a (121 mg, 0.2 mmol) was dissolved in a mixture of MeOH (2 mL), THF (2 mL) and 6 N aq. NaOH (2 mL). The reaction mixture was stirred for 3 h at room temperature. After the reaction solvent was removed in vacuo, the resulting residue was dissolved in EtOAc, washed once with 1 N HCl, and dried over anhydrous Na$_2$SO$_4$. Solvent was removed in vacuo, and the residue was purified by SiO$_2$ column chromatography (MeOH/EtOAc=1/9) to yield the carboxylic acid as a light yellow oil (110 mg, 93%). $^1$H NMR (500 MHz, CDCl$_3$) δ 7.63 (m, 1H), 7.03 (br, s, 1H), 6.50 (br, s, 1H), 6.23–6.15 (m, 2H), 4.04–3.93 (m, 7H), 3.20–2.97 (m, 4H), 2.39 (m, 3H), 2.24 (m, 4H), 1.72 (m, 6H), 1.51 (br, s, 2H), 1.36 (br, s, 2H), 1.27–1.22 (m, 6H). $^{13}$C NMR (75 MHz, DMSO-d$^6$) δ 173.42, 171.10, 154.61, 153.19, 147.60, 139.35, 135.59, 131.53, 109.01, 108.10, 80.89, 78.57, 71.60, 68.36, 55.92, 34.57, 34.37, 33.34, 33.12, 31.57, 28.58, 27.35, 25.38, 24.17, 23.84, 23.78, 23.74. MS-ESI (m/z): [M+H]$^+$ calculated for $C_{28}H_{41}N_4O_{10}$, 593.3; found, 593.4. [M+Na]$^+$ calculated for $C_{28}H_{40}N_4NaO_{10}$, 615.3; found, 615.4. [M−H]$^-$ calculated for $C_{28}H_{39}N_4O_{10}$, 591.3; found, 591.7.

The carboxylic acid precursor (80 mg, 0.135 mmol), DSC (173 mg, 0.675 mmol) and pyridine (53 mg, 0.675 mmol) were dissolved in CH$_3$CN (2 mL) and reacted at room temperature for 16 h. Solvent was then removed in vacuo, and the crude material was re-dissolved in toluene and evaporated to dryness again. The remaining residue was dissolved in EtOAc, washed once with 0.1 N aq. HCl, washed once with saturated aq. NaHCO$_3$ and dried over anhydrous Na$_2$SO$_4$. Solvent was removed in vacuo, and the residue was purified by SiO$_2$ column chromatography (CHCl3/acetone=1/1) to yield 2a as a light yellow oil (70 mg, 75%). $^1$H NMR (500 MHz, CDCl$_3$) δ 7.61 (m, 1H), 6.98 (m, 1H), 6.17 (m, 2H), 5.12 (m, 1H), 4.01 (m, 2H), 3.95 (m, 6H), 3.69 (m, 1H), 3.54 (m, 1H), 3.15 (m, 1H), 3.07 (s, 3H), 2.94 (s, 1H), 2.84 (m, 4H), 2.64 (m, 2H), 2.37 (m, 2H), 2.17 (m, 4H), 1.95 (m, 2H), 1.79 (m, 3H), 1.62 (m, 2H), 1.47 (m, 2H), 1.29 (m, 2H). HRMS (TOF MS ES+) (m/z): [M+Na]$^+$ calculated for $C_{32}H_{43}N_5NaO_{12}$, 712.2806; found, 712.2802.

$$5a \xrightarrow[\text{2) DSC, Pyridine, CH}_3\text{CN}]{\text{1) 2N NaOH, MeOH, THF}}$$

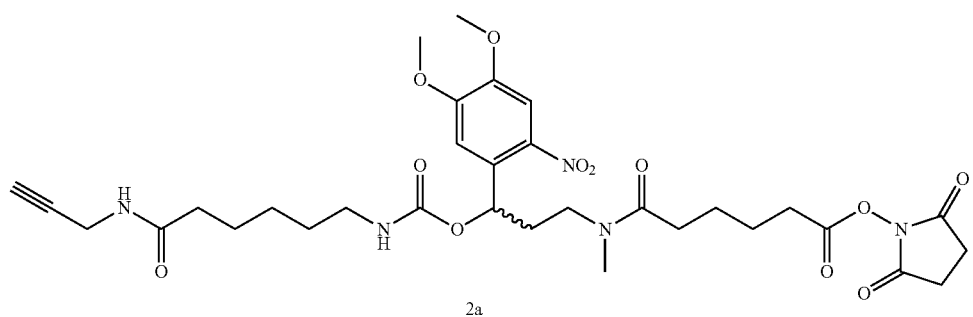

2a

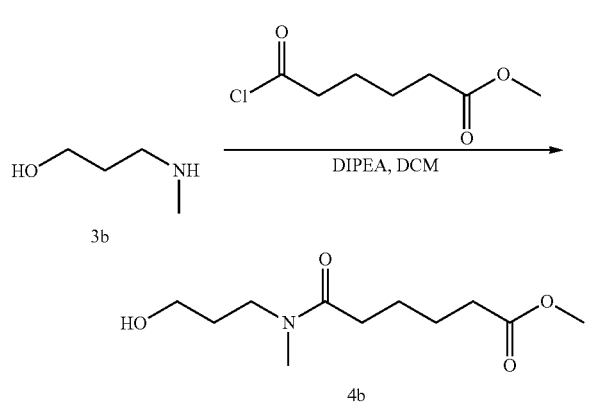

Methyl 6-((3-hydroxypropyl)(methyl)amino)-6-oxohexanoate (4b). 3-(methylamino)propan-1-ol (3b, 660 µL, 6.96 mmol) was dissolved in anhydrous DCM, and the solution was cooled to −78° C. Methyl adipoyl chloride (490 µL, 3.15 mmol) was added, and the reaction mixture was stirred for 2 h at 0° C. under nitrogen. Solvent was removed in vacuo and the residue was purified by SiO$_2$ column chromatography (EtOAc/CHCl$_3$, stepwise gradient from 1/1 to 1/0) to yield 4b as a colorless oil (303 mg, 42%). $^1$H NMR (400 MHz, CDCl$_3$) δ 4.00 (t, 1H, J=7.0 Hz), 3.67 (d, 3H, J=3.2 Hz), 3.53 (t, 2H, J=3 Hz), 3.47 (dt, 2H, J=7.2 Hz, 5.4 Hz), 2.99 (s, 3H), 2.36 (m, 4H), 1.69 (m, 4H). $^{13}$C NMR (100 MHz, CDCl$_3$) δ 174.08, 173.94, 57.85, 51.60, 43.90, 35.42, 33.81, 32.99, 29.41, 24.63, 24.55. MS-ESI (m/z): [M+H]$^+$ calculated for C$_{11}$H$_{22}$NO$_4$, 232.1; found, 232.1. [M+Na]$^+$ calculated for C$_{11}$H$_{21}$NNaO$_4$, 254.1; found, 254.1.

added to 1,1'-carbonyl diimidazole (88.7 mg, 0.547 mmol) in anhydrous DCM (1 mL). The reaction mixture was stirred for 1.5 h at room temperature under nitrogen, diluted with CHCl$_3$, washed two times with water, and dried over anhydrous MgSO$_4$. Solvent was removed in vacuo to yield crude imidazole carbamate as a yellow gum (62.5 mg, 88%). Without further purification, the imidazole carbamate (60.2 mg, 0.092 mmol) was dissolved in CHCl$_3$ (0.4 mL), and to this mixture was added 6-oxo-6-(prop-2-ynylamino)hexan-1-aminium trifluoroacetate salt (62.7 mg, 0.222 mmol), N,N-diisopropylethylamine (155 µL, 0.888 mmol), and N-hydroxybenzotriazole (19.0 mg, 0.141 mmol) in anhydrous DCM (0.5 mL). The reaction was stirred overnight at room temperature under nitrogen, diluted with CHCl$_3$, washed once with 1 N HCl, washed once with 0.5 M aqueous bicarbonate, washed once with brine, and dried over anhydrous MgSO$_4$. Solvent was removed in vacuo, and the residue was purified by SiO$_2$ column chromatography (CHCl$_3$/acetone, stepwise gradient from 1/0 to 5/1, then CHCl$_3$/MeOH=9/1) to yield 5b as a thick white gum (19.9 mg, 45% from 4b). $^1$H NMR (400 MHz, CDCl$_3$) δ 6.16 (d, 1H, J=29.6 Hz), 4.98 (d, 1H, J=72.8 Hz), 4.06 (m, 4H), 3.67 (s, 3H), 3.409 (dt, 2H, J=22.8 Hz, 7.2 Hz), 3.17 (q, 2H, J=6.3 Hz), 2.95 (d, 3H, J=32.8 Hz), 2.34 (m, 4H), 2.22 (m, 3H), 1.85 (m, 2H), 1.66 (m, 6H), 1.51 (q, 2H, J=7.1 Hz), 1.35 (q, 2H, J=7.2 Hz). MS-ESI (m/z): [M+H]$^+$ calculated for C$_{21}$H$_{36}$N$_3$O$_6$, 426.3; found, 426.1. [M+Na]$^+$ calculated for C$_{21}$H$_{35}$N$_3$NaO$_4$, 448.2; found, 448.2.

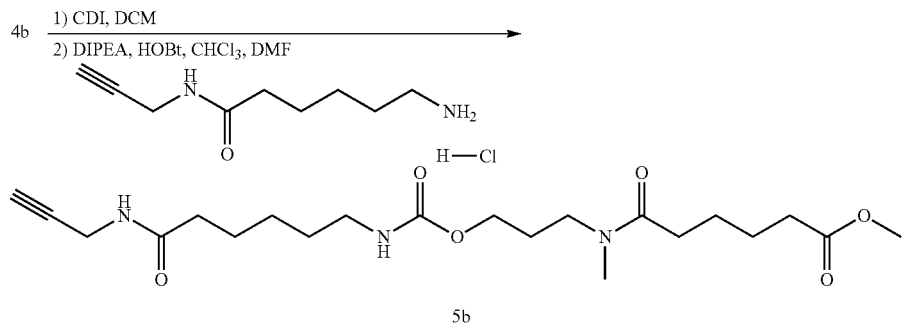

Methyl 17-methyl-5, 12, 18-trioxo-13-oxa-4, 11, 17-triazatricos-1-yn-23-oate (5b). Compound 4b (50.4 mg, 0.218 mmol) was dissolved in anhydrous DCM (0.75 mL) and

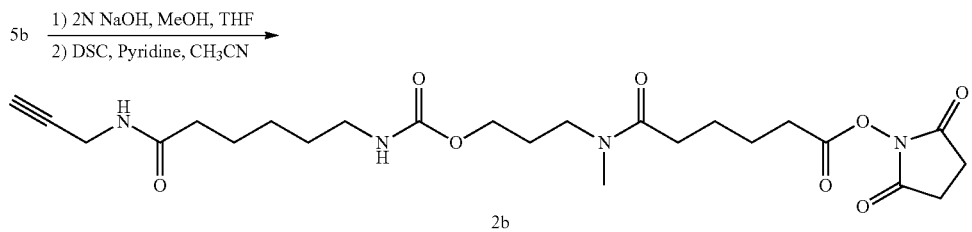

2,5-dioxopyrrolidin-1-yl-17-methyl-5, 12, 18-trioxo-13-oxa-4, 11, 17-triazatricos-1-yn-23-oate (2b). Compound 5b (18.3 mg, 43.1 μmol) was dissolved in a mixture of MeOH (1.5 mL), THF (1.5 mL) and 6 N aq. NaOH (1.5 ml). The reaction mixture was stirred for 3 h at room temperature and organic solvent was removed in vacuo. The remaining aqueous solution was acidified with 1 N HCl and extracted with EtOAc. The organic layer was dried over anhydrous $MgSO_4$ and solvent was removed in vacuo to yield the carboxylic acid as a colorless oil (16.0 mg, 90%). $^1$H NMR (400 MHz, $CDCl_3$) δ 6.32 (d, 1H, J=14 Hz), 5.21 (d, 1H, J=112 Hz), 4.08 (m, 4H), 3.44 (d, 2H, J=22.8 Hz), 3.17 (s, 2H), 2.96 (d, 3H, J=36.4 Hz), 2.38 (m, 4H), 2.24 (m, 4H), 1.89 (m, 2H), 1.69 (m, 6H), 1.52 (m, 2H), 1.36 (m, 2H). MS-ESI (m/z): [M+H]$^+$ calculated for $C_{20}H_{34}N_3O_6$, 412.2; found, 412.2. [M+Na]$^+$ calculated for $C_{20}H_{33}N_3NaO_6$, 434.2; found, 434.2. [M-H]$^-$ calculated for $C_{20}H_{32}N_3O_6$, 410.2; found, 410.3.

The carboxylic acid (18.5 mg, 44.9 pmol), DSC (28.5 mg, 111 μmol) and pyridine (39.2 mg, 0.496 mmol) were dissolved in $CH_3CN$ (0.5 mL) and reacted at room temperature for 16 h. Solvent was then removed in vacuo, and the crude material was re-dissolved in toluene and evaporated to dryness again. The remaining residue was dissolved in EtOAc, washed once with 0.1 N aq. HCl, washed once with saturated aq. $NaHCO_3$ and dried over anhydrous $MgSO_4$. Solvent was removed in vacuo to yield 2b as a pale yellow gum (14.7 mg, 64%). $^1$H NMR (400 MHz, $CDCl_3$) δ 6.03 (d, 1H, J=28.8 Hz), 4.90 (d, 1H, J=36.4 Hz), 4.06 (m, 4H), 3.41 (dt, 2H, J=23.6 Hz, 7.2 Hz), 3.14 (m, 3H), 2.95 (d, 3H, J=32.4 Hz), 2.85 (s, 4H), 2.65 (t, 2H, J=7.0 Hz), 2.35 (t, 2H, J=6.4 Hz), 2.21 (m, 3H), 1.81 (m, 6H), 1.67 (q, 2H, J=3.7 Hz), 1.52 (q, 2H, J=7.2 Hz), 1.35 (m, 2H). HRMS (TOF MS ES+) (m/z): [M+Na]$^+$ calculated for calculated for $C_{24}H_{36}N_4NaO_8$, 531.2431; found, 531.2416.

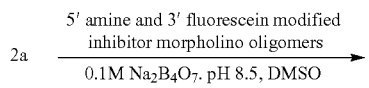

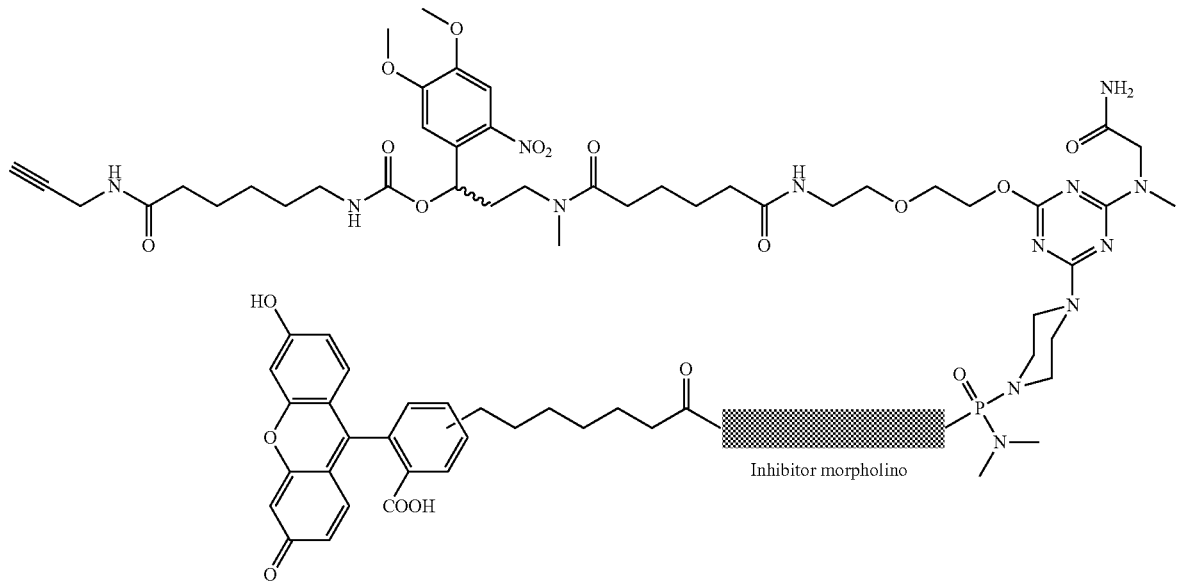

7a-h

DMNB-conjugated ntl MO inhibitory oligomers (7a-h). Synthetic procedures for the ntl MO inhibitors were analogous to those described for 7e. MO sequences were: 7a (5'-TATGTCTGCC-3') (SEQ ID NO:2), 7b (5'-TATGTCTGCCTC-3') (SEQ ID NO:7), 7c (5'-TATGTCTGCCTCAA-3') (SEQ ID NO:8), 7d (5'-TATGTCTGCCTCAAGT-3') (SEQ ID NO:9), 7e (5'-GCCTCAAGTC-3') (SEQ ID NO:10), 7f (5'-CTGCCTCAAGTC-3') (SEQ ID NO:11), 7g (5'-GTCTGCCTCAAGTC-3') (SEQ ID NO:12), 7h (5'-ATGTCTGCCTCAAGTC-3') (SEQ ID NO:13). Compounds 7a-h were recovered as yellow solids (70-90 nmol, 70-90%). MS-ESI (m/z): $[M+H]^+$ calculated for photolyzed 7a $C_{185}H_{266}N_{65}O_{64}P_{10}$, 4734; found, 4736. $[M+H]^+$ calculated for 7b $C_{198}H_{287}N_{72}O_{70}P_{12}$, 5167; found, 5170. $[M+H]^+$ calculated for photolyzed 7c $C_{232}H_{339}N_{88}O_{79}P_{14}$, 6058; found, 6060. $[M+H]^+$ calculated for 7d $C_{246}H_{360}N_{97}O_{85}P_{16}$, 6532; found, 6534. $[M+H]^+$ calculated for 7e $C_{184}H_{264}N_{69}O_{61}P_{10}$, 4728; found, 4728. $[M+H]^+$ calculated for photolyzed 7f $C_{197}H_{285}N_{76}O_{67}P_{12}$, 5162; found, 5165. $[M+H]^+$ calculated for 7g $C_{231}H_{338}N_{89}O_{79}P_{14}$, 6059; found, 6064. $[M+H]^+$ calculated for 7h $C_{255}H_{375}N_{100}O_{87}P_{16}$, 6729; found, 6729.

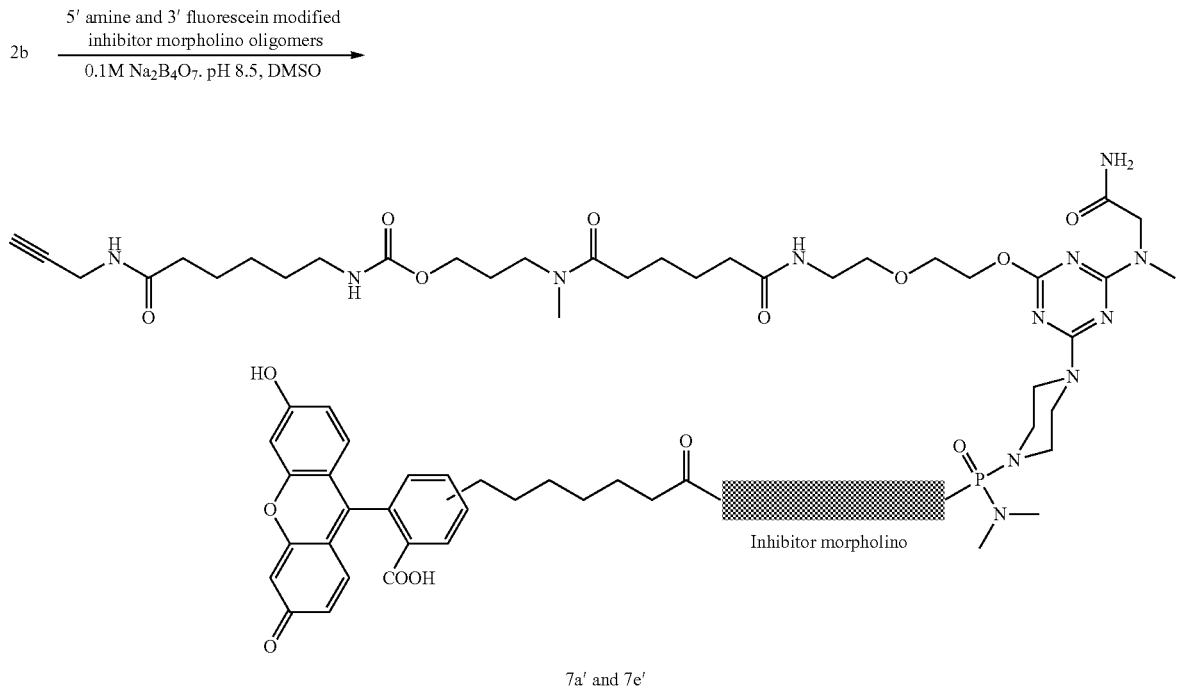

7a' and 7e'

Non-cleavable ntl MO inhibitors (7a' and 7e'). Synthetic procedures for non-photocleavable versions of the ntl cMOs were analogous to those described for 7e. Inhibitor MO sequences were identical to 7a and 7e. Each MO oligomer (100 nmol) was dissolved in 0.1 M $Na_2B_4O_7$, pH=8.5 (100 μL), and combined with 2b (0.76 mg, 1.5 μmol) in DMSO (15 μL). The remaining synthetic procedures were identical to those of 7a-h. Yield: 70-90 nmol, 70-90%. MS-ESI (m/z): $[M+H]^+$ calculated for 7a' $C_{177}H_{259}N_{64}O_{60}P_{10}$, 4553; found, 4552. $[M+H]^+$ calculated for 7e' $C_{176}H_{257}N_{68}O_{57}P_{10}$, 4547; found, 4547.

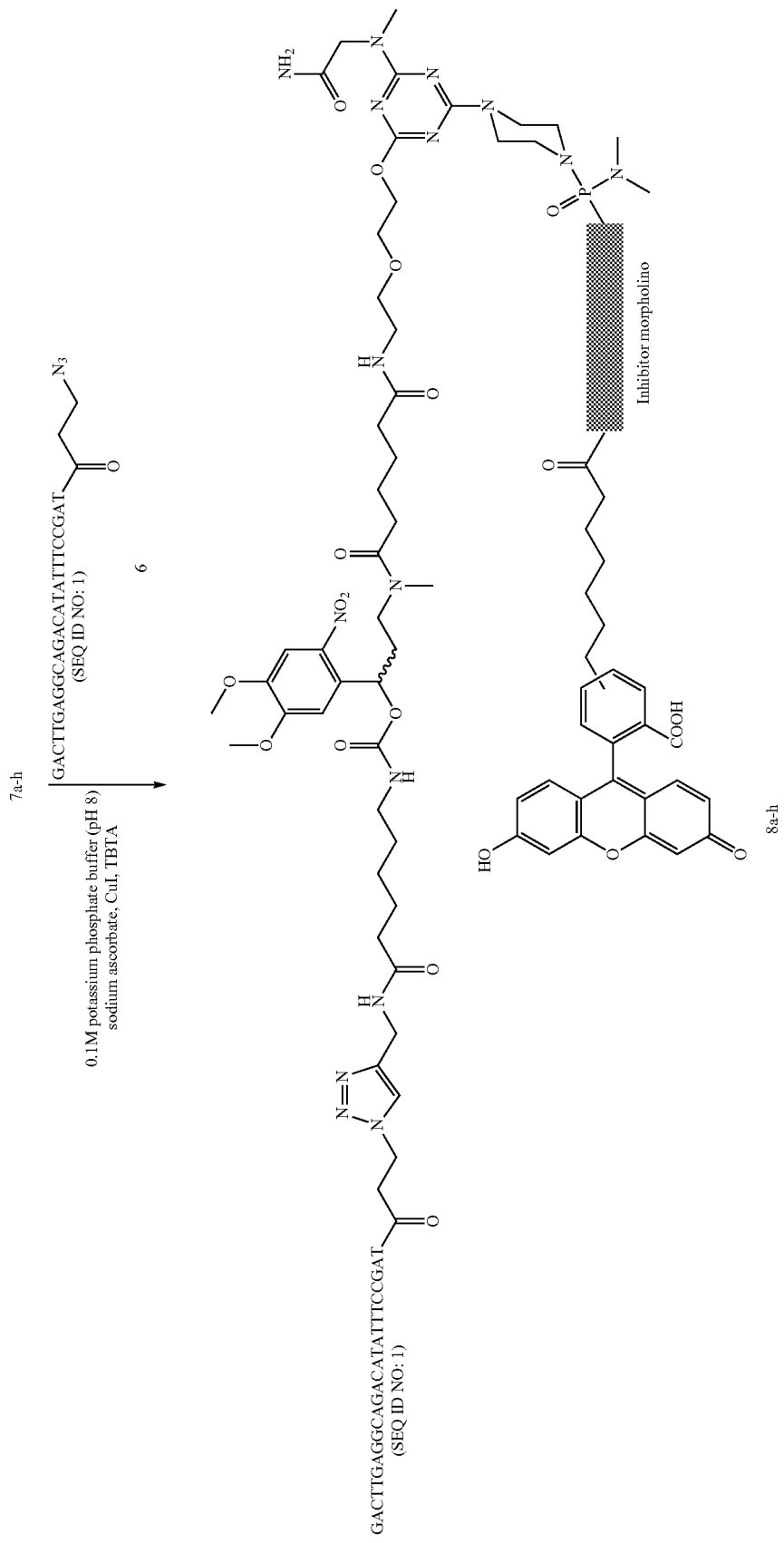

DMNB-based ntl cMOs (8a-h). Synthetic procedures for the ntl cMOs were analogous to those described for 8e. Compounds 8a-h were recovered as yellow solids (5.6-10.5 nmol, 6-10% overall). MS-ESI (m/z): [M+H]$^+$ calculated for 8a $C_{489}H_{739}N_{215}O_{167}P_{35}$, 13385; found, 13384. [M+H]$^+$ calculated for 8b $C_{512}H_{776}N_{224}O_{176}P_{37}$, 14031; found, 14032. [M+H]$^+$ calculated for 8c $C_{536}H_{812}N_{238}O_{182}P_{39}$, 14709; found, 14705. [M+H]$^+$ calculated for 8d $C_{560}H_{849}N_{249}O_{191}P_{41}$, 15395; found, 15391. [M+H]$^+$ calculated for 8e $C_{488}H_{737}N_{219}O_{164}P_{35}$, 13379; found, 13380. [M+H]$^+$ calculated for 8f $C_{511}H_{774}N_{228}O_{173}P_{37}$, 14025; found, 14025. [M+H]$^+$ calculated for 8g $C_{535}H_{811}N_{239}O_{182}P_{39}$, 14711; found, 14713. [M+H]$^+$ calculated for 8 h $C_{559}H_{848}N_{250}O_{190}P_{41}$, 15380; found, 15379.

a white solid (16 nmol, 16% overall). MS-ESI (m/z): [M+H]$^+$ calculated for 10 $C_{501}H_{776}N_{241}O_{165}P_{38}$, 13992; found, 13993.

etsrp cMO (11). Synthetic procedures identical to those for ntl cMOs 8a-h were utilized. Final product was recovered as a yellow solid (8.7 nmol, 9% overall). MS-ESI (m/z): [M+H]$^+$ calculated for 11 $C_{488}H_{740}N_{210}O_{168}P_{35}$, 13320; found, 13322.

spt cMO (12). Synthetic procedures identical to those for ntl cMOs 8a-h were utilized. Final product was recovered as a yellow solid (10.5 nmol, 10% overall). MS-ESI (m/z): [M+H]$^+$ calculated for 12 $C_{487}H_{736}N_{217}O_{166}P_{35}$, 13370; found, 13369.

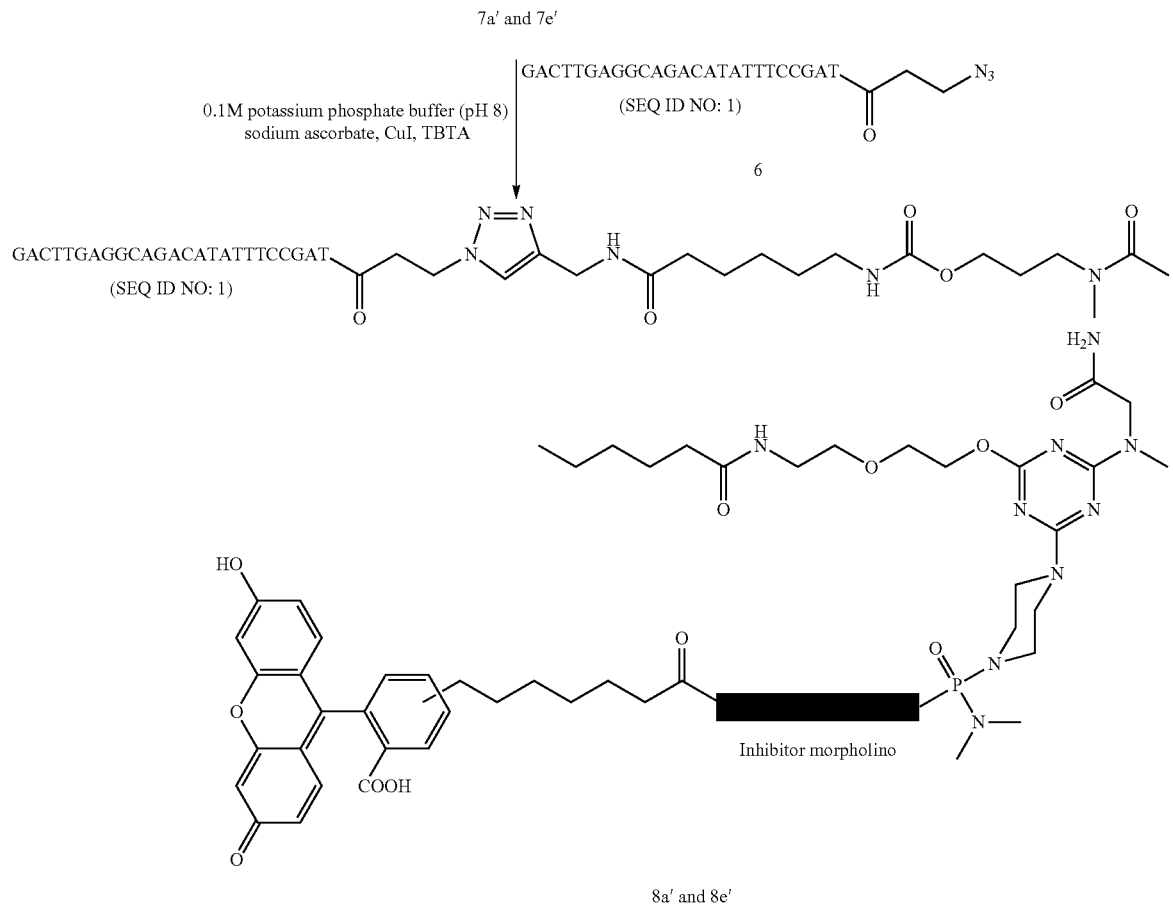

8a' and 8e'

Non-cleavable ntl MO hairpins (8a' and 8e'). The functionalized oligomers 7a' and 7e' (50 nmol) were conjugated with azide-functionalized ntl MO 6 (50 nmol). The synthetic procedures and yields were identical to those of 8a-h. MS-ESI (m/z): [M+H]$^+$ calculated for 8a' $C_{481}H_{732}N_{214}O_{163}P_{35}$, 13204; found, 13204. [M+H]$^+$ calculated for 8e' $C_{480}H_{730}N_{218}O_{160}P_{35}$, 13198; found, 13199.

flh cMO (9). Synthetic procedures identical to those for ntl cMOs 8a-h were utilized. Final product was recovered as a yellow solid (5.6 nmol, 6% overall). MS-ESI (m/z): [M+H]$^+$ calculated for 9 $C_{489}H_{737}N_{218}O_{168}P_{35}$, 13441; found, 13441.

heg cMO (10). Synthetic procedures identical to those for ntl cMOs 8a-h were utilized. Final product was recovered as Example 3

Photolabile protecting groups and linkers for a variety of functional groups have become important in combinatorial chemistry and cell biology, and a number of molecular structures have been utilized. Photoremovable groups for controlling and manipulating cell physiology are valuable because of their ability to inactivate or "cage" a physiologically active messenger and then release or "uncage" it with a flash of light. This is an excellent way to achieve temporal control over messenger release and examine the fast kinetics or spatial heterogeneity of biochemical responses in cell or tissue culture.

To be useful in biological experiments, a caging group must undergo photolysis rapidly, in high yield, and at wavelengths that are not detrimental to the biological system. It should not interfere with the methods used to measure the response of the system, and the post-photolysis remains of the caging group should not interact with the physiological processes under study. Ideally, the "caged" compound will exhibit satisfactory water solubility and hydrolytic stability in the dark.

Most caging groups, including DMNB, require ultraviolet (UV) light, which is damaging to cells. A less damaging approach utilizes infrared (IR) light and multiphoton excitation, which confines the messenger activation to the focus of the laser beam. In single-photon uncaging processes at UV wavelengths, any molecules of the caged compound exposed to the beam of light are uncaged, severely limiting the three-dimensional spatial resolution of release. In a multiphoton or two-photon process, the chromophores simultaneously absorbs two IR photons from a pulsed and tightly focused laser beam. At very high intensities, two IR photons exploit the metastable virtual state and have the same effect as one photon of half the wavelength. Uncaging occurs only at the focus of the laser beam, and because cells are relatively transparent to IR light, photodamage to the tissue, light absorption, and scattering are minimized, allowing much deeper and more accurate penetration into complex tissue samples than can be achieved with UV light. Thus, multiphoton uncaging provides an excellent method for controlling the temporal and spatial release of biological effectors in real time and on living tissue.

The following methods were used for synthesis of a bifunctional linker. The linker was then used to join two morpholino oligonucleotides to form a caged structure based on 8-bromo-7-hydroxyquinoline. While UV irradiation allows for activation of DMNB containing caged morpholinos, benefits could be obtained from a light-cleavable moiety that does not require UV irradiation.

Synthesis of Bifunctional Cross-Linker Compatible with 2-Photon Irradiation.

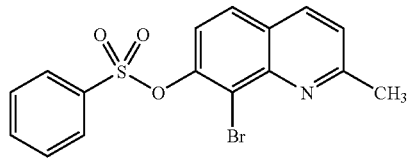

SO185

8-Bromo-2-methylquinolin-7-yl benzenesulfonate (SO185). A mixture of 8-bromo-2-methylquinolin-7-ol (1.10 g, 4.62 mmol) and N,N-diisopropylethylamine (1.19 g, 9.24 mmol) were dissolved in anhydrous DCM (10 mL), and the solution was cooled to 0° C. Benzenesulfonyl chloride (0.90 g, 5.10 mmol) in 5 mL DCM was added over 10 min, and the reaction mixture was stirred for 14 h at room temperature under argon. Solvent was removed in vacuo, and residue was dissolved in EtOAc and washed twice with saturated aq. NaHCO$_3$ and then dried over anhydrous Na2SO$_4$. Solvent was removed in vacuo, and the residue was purified by SiO$_2$ column chromatography (Hexanes/EtOAc=1/1) to yield SO185 as a white solid (1.70 g, 4.49 mmol, 97% yield). $^{13}$CNMR (ppm, 500 MHz, CDCl$_3$, 298 K) δ 161.588, 148.067, 145.802, 136.573, 135.924, 134.834, 129.444, 128.907, 128.029, 126.122, 123.236, 121.950, 118.038, 25.922. $^{1}$HNMR (ppm, 400 MHz, CDCl$_3$, 298 K) δ: 8.049 (d, 1H, J=8.4 Hz), 7.976 (m, 1H), 7.958 (m, 1H), 7.758 (d, 1H, J=8.8 Hz), 7.701-7.657 (m, 1H), 7.599 (d, 1H, J=8.8 Hz), 7.554-7.507 (m, 2H), 7.346 (d, 1H, J=8.0 Hz), 2.785 (s, 3H). MS-ESI (m/z): [M+H]$^+$ calculated for C$_{16}$H$_{13}$BrNO$_3$S, 378.0 ($^{79}$Br) and 380.0 ($^{81}$Br); found 378.0 ($^{79}$Br) and 379.9 ($^{81}$Br).

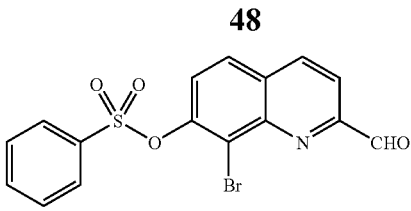

SO186

8-Bromo-2-formylquinolin-7-yl benzenesulfonate (SO186). A mixture of SeO$_2$ (500 mg, 4.51 mmol) and 1,4-dioxane (10 mL) was heated to over 80° C. 8-Bromo-2-methylquinolin-7-yl benzenesulfonate (1.70 g, 4.49 mmol) in 1,4-dioxane (5 mL) was added. After stirring at 80° C. for 24 h, the reaction was cooled and vacuum filtered. The filtrate was collected and concentrated, leaving a yellow solid. Purification by silica gel with CHCl$_3$ (100%) gave SO186 as a white solid (1.60 g, 4.08 mmol, 91% yield). $^{13}$CNMR (ppm, 500 MHz, CDCl$_3$, 298 K) δ: 193.330, 153.804, 149.083, 146.098, 138.351, 135.815, 135.165, 129.787, 129.663, 128.990, 128.365, 125.611, 119.933, 118.514. $^{1}$HNMR (ppm, 500 MHz, CDCl$_3$, 298 K) δ: 10.247 (s, 1H), 8.365 (d, 1H, J=7.5 Hz), 8.090 (d, 1H, J=8.5 Hz), 7.986 (d, 2H, J=7.0 Hz), 7.913 (d, 1H, J=9.0 Hz), 7.794 (d, 1H, J=9.0 Hz), 7.719 (t, 1H, J=7.5 Hz), 7.565 (t, 2H, J=8.0 Hz). MS-ESI (m/z): [M+H]$^+$ calculated for C$_{16}$H$_{11}$BrNO$_4$S, 392.0 ($^{79}$Br) and 394.0 ($^{81}$Br); found 391.8 ($^{79}$Br) and 393.8 ($^{81}$Br).

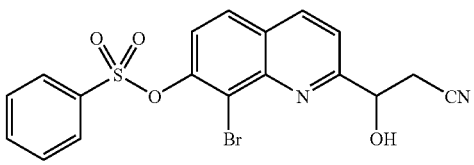

SO187

8-Bromo-2-(2-cyano-1-hydroxyethyl)quinolin-7-yl benzenesulfonate (SO187). To a stirred solution of AcOLi (27 mg, 0.41 mmol) in DMF (1 mL) were added successively a solution of 8-bromo-2-formylquinolin-7-yl benzenesulfonate (1.60 g, 4.08 mmol) in anhydrous DMF (10 mL) and TMSCH$_2$CN (465 mg, 4.11 mmol) at 0° C. And the reaction mixture was slowly warmed to room temperature. The mixture was stirred for 12 h at the same temperature and quenched with 15% citric acid (5.0 mL) and MeOH (5.0 mL). After the removal of MeOH in vacuo, the mixture was extracted with AcOEt and organic layer was washed with brine and dried over anhydrous Na$_2$SO$_4$, and evaporated. Purification by silica gel chromatography (Hexanes/EtOAc=2/1) gave S0187 as a yellow gum (0.89 g, 2.05 mmol, 50% yield). $^{13}$CNMR (ppm, 500 MHz, CDCl$_3$, 298 K) δ: 159.989, 148.716, 144.388, 138.493, 135.675, 135.042, 129.556, 128.819, 128.189, 127.380, 123.481, 119.173, 118.419, 117.117, 68.926, 26.812. $^{1}$HNMR (ppm, 500 MHz, CDCl$_3$, 298 K) δ: 8.262 (d, 1H, J=8.5 Hz), 7.968 (d, 2H, J=8.0 Hz), 7.836 (d, 1H, J=9.0 Hz), 7.716 (t, 1H, J=7.0 Hz), 7.633 (d, 1H, J=9.0 Hz), 7.588-7.545 (m, 3H), 5.224-5.188 (m, 1H), 5.126 (d, 1H, J=6.0 Hz), 3.031-2.929 (m, 2H). MS-ESI (m/z): [M+H]$^+$ calculated for C$_{18}$H$_{14}$BrN$_2$O$_4$S, 433.0 ($^{79}$Br) and 435.0 ($^{81}$Br); found 432.9 ($^{79}$Br) and 434.9 ($^{81}$Br).

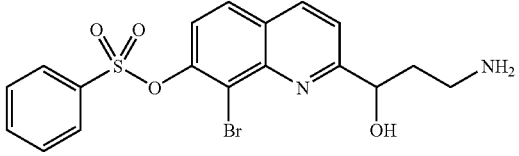

SO190

2-(3-Amino-1-hydroxypropyl)-8-bromoquinolin-7-yl benzenesulfonate (SO190). To a stirred solution of 8-Bromo-2-(2-cyano-1-hydroxyethyl)quinolin-7-yl benzenesulfonate (890 mg, 2.05 mmol) in THF (2 mL) were slowly added 1 M BH3-THF complex (4.1 mL, 4.10 mmol) at 0° C. And the reaction mixture was slowly warmed to room temperature. The mixture was then refluxed for 1 h, then cooled to 0° C. and quenched with MeOH. After the removal of solvents in vacuo, the mixture was stirred with 1.2N HCl in MeOH for 10 min. After the removal of solvents in vacuo again, the residue was dissolved in $CHCl_3$ extracted with and washed twice with saturated aq. $NaHCO_3$ and then dried over anhydrous $Na_2SO_4$. Solvent was removed in vacuo to yield 895 mg SO190 as a yellow oil and was used for next step without further purification.

MS-ESI (m/z): $[M+H]^+$ calculated for $C_{18}H_{14}BrN_2O_4S$, 437.0 ($^{79}Br$) and 439.0 ($^{81}Br$); found 437.1 ($^{79}Br$) and 439.1 ($^{81}Br$).

Methyl 14-(8-bromo-7-(phenylsulfonyloxy)quinolin-2-yl)-5,12,18-trioxo-13-oxa-4,11,17triazatricos-1-yn-23-oate (SO203). To a stirred solution of methyl 6-(3-(8-bromo-7-(phenylsulfonyloxy)quinolin-2-yl)-3-hydroxypropylamino)-6-oxohexanoate (400 mg, 0.69 mmol) and N,N-diisopropylethylamine (244 μL, 1.38 mmol) in anhydrous THF (5 mL), were added carbonyl diimidazole (168 mg, 1.04 mmol) over at 0° C., and the reaction mixture was stirred for 12 h at room temperature under argon. Solvent was removed in vacuo, and residue was dissolved in $CHCl_3$ and washed twice with brine and then dried over anhydrous $Na_2SO_4$. Solvent was removed in vacuo, and the residue was purified by $SiO_2$ column chromatography ($CHCl_3/(CH_3)_2CO=3/1$) to yield the imidzole intermediate as a colorless oil (220 mg, 0.33 mmol, 47%). MS-ESI (m/z): $[M+H]^+$ calculated for

SO201

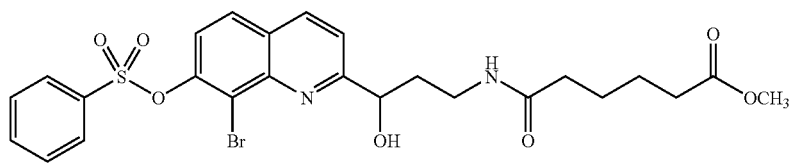

Methyl 6-(3-(8-bromo-7-(phenylsulfonyloxy)quinolin-2-yl)-3-hydroxypropylamino)-6-oxohexanoate (S0201). To a stirred solution of 2-(3-amino-1-hydroxypropyl)-8-bromoquinolin-7-yl benzenesulfonate (890 mg, 2.05 mmol) and N,N-diisopropylethylamine (723 μL, 4.1 mmol) in anhydrous DCM (5 mL), were added methyl adipoyl chloride (365 mg, 2.05 mmol) over 10 min at 0° C., and the reaction mixture was stirred for 6 h at room temperature under argon. Solvent was removed in vacuo, and residue was dissolved in EtOAc and washed twice with saturated aq. $NaHCO_3$ and then dried over anhydrous $Na_2SO_4$. Solvent was removed in vacuo, and the residue was purified by $SiO_2$ column chromatography ($CHCl_3/(CH_3)_2CO=3/1$) to yield SO191 as a colorless oil (505 mg, 43%). $^{13}CNMR$ (ppm, 500 MHz, $CDCl_3$, 298 K) δ: 174.151, 173.254, 163.668, 148.487, 144.276, 137.799, 135.880, 134.950, 129.532, 128.891, 128.133, 127.039, 122.863, 119.397, 118.307, 71.844, 51.790, 37.099, 36.906, 36.446, 33.857, 25.233, 24.591. $^1HNMR$ (ppm, 500 MHz, $CDCl_3$, 298 K) δ: 8.135 (d, 1H, J=9 Hz), 7.927 (d, 2H, J=9 Hz), 7.754 (d, 1H, J=9.0 Hz), 7.669 (t, 1H, J=8 Hz), 7.531–7.480 (m, 4H), 6.585–6.562 (m, 1H), 5.318 (s, 1H), 4.943–4.920 (m, 1H), 3.604 (s, 3H), 3.587–3.521 (m, 1H), 3.338–3.276 (m, 1H), 2.286–2.259 (m, 2H), 2.214–2.163 (m, 1H), 2.148–2.120 (m, 2H), 1.843–1.773 (m, 1H), 1.622–1.555 (m, 4H). MS-ESI (m/z): $[M+H]^+$ calculated for $C_{25}H_{28}BrN_2O_7S$, 579.1 ($^{79}Br$) and 581.1 ($^{81}Br$); found 579.2 ($^{79}Br$) and 581.2 ($^{81}Br$).

$C_{29}H_{30}BrN_4O_8S$, 673.1 ($^{79}Br$) and 675.1 ($^{81}Br$); found 673.2 ($^{79}Br$) and 675.3 ($^{81}Br$). To a stirred solution of imidazole intermediate (220 mg, 0.33 mmol) in anhydrous DMF (2 mL), were added N,N-diisopropylethylamine (117 μL, 0.66 mmol) and 6-amino-N-(prop-2-ynyl)hexanamide hydrochloride (135 mg, 0.66 mmol) in 1 mL DMF. After the reaction mixture was stirred for 12 h at room temperature under argon, the solvent was removed in vacuo. The residue was dissolved in $CHCl_3$ and washed twice with saturated aq. $NaHCO_3$ and then dried over anhydrous $Na_2SO_4$. Chloroform was removed in vacuo, and the residue was purified by $SiO_2$ column chromatography ($CHCl_3/(CH_3)_2CO=2/1$) to yield SO203 as a colorless oil (108 mg, 0.14 mmol, 20% over two steps). $^{13}CNMR$ (ppm, 500 MHz, $CDCl_3$, 298 K) δ: 174.151, 172.897, 172.861, 162.301, 156.110, 148.311, 145.069, 137.687, 135.772, 134.962, 129.528, 128.819, 128.141, 126.995, 122.755, 119.401, 118.640, 79.955, 74.817, 71.531, 51.754, 40.930, 36.450, 36.153, 35.672, 34.298, 33.849, 29.625, 29.172, 26.263, 25.261, 25.092, 24.579. $^1HNMR$ (ppm, 500 MHz, $CDCl_3$, 298 K) δ: 8.185 (d, 1H, J=8.5 Hz), 7.975 (d, 2H, J=8.0 Hz), 7.788 (d, 1H, J=9.0 Hz), 7.721 (t, 1H, J=7.0 Hz), 7.586–7.522 (m, 4H), 6.602 (br, s, 1H), 6.343 (br, s, 1H), 5.960 (t, 1H, J=6 Hz), 5.349 (t, 1H, J=6 Hz), 4.032–4.012 (m, 2H), 3.657 (s, 3H), 3.429–3.390 (m, 1H), 3.299–3.259 (m, 1H), 3.233–3.193 (m, 1H), 3.172–3.110 (m, 1H), 2.326–2.299 (m, 2H), 2.229–2.175 (m, 7H), 1.677–1.598 (m, 6H), 1.534–1.493 (m, 2H), 1.373–1.331 (m, 2H). MS-ESI (m/z): $[M+H]^+$ calculated for $C_{35}H_{42}BrN_4O_9S$, 773.2 ($^{79}Br$) and 775.2 ($^{81}Br$); found 773.3 ($^{79}Br$) and 775.3 ($^{81}Br$).

SO203

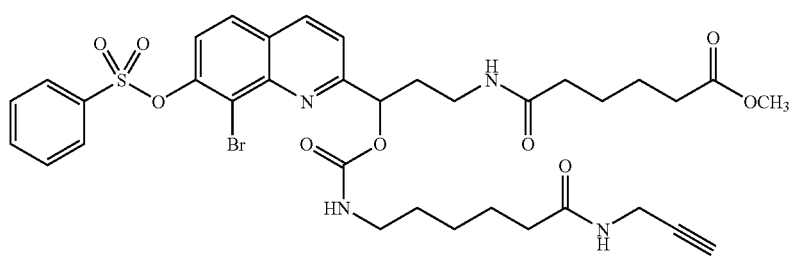

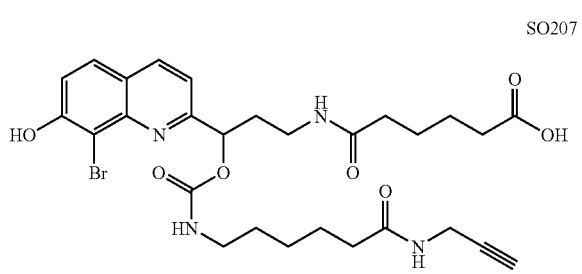

14-(8-Bromo-7-hydroxyquinolin-2-yl)-5,12,18-trioxo-13-oxa-4,11,17-triazatricos-1-yn-23-oic acid (SO207). To a stirred solution of methyl 14-(8-bromo-7-(phenylsulfonyloxy)quinolin-2-yl)-5,12,18-trioxo-13-oxa-4,11,17-triazatricos-1-yn-23-oate (20 mg, 0.026 mmol) in MeOH (500 uL), were added 0.4 N NaOH (500 uL), and the reaction mixture was stirred for 4 h at room temperature. Methanol was removed in vacuo, and remaining mixture was loaded onto a TOYOPEARL SuperQ-650M packed column pre-washed with 0.2 N NaOH. After washing the column with $CH_3CN$/$H_2O$ (1:1) twice, the loaded compound was eluted with AcOH/$CH_3CN$/$H_2O$ (5:50:45). After remove the $CH_3CN$ in vacuo, the remaining mixture was lyophilized overnight to dryness. The residue was dissolved in MeOH/$CH_3Cl$, transferred to a new vial and evaporated to give a yellow gum (15 mg, 0.024 mmol, 92%) and was used for next step without further purification. MS-ESI (m/z): $[M+H]^+$ calculated for $C_{28}H_{36}BrN_4O_7$, 619.2 ($^{79}Br$) and 621.2 ($^{81}Br$); found 619.3 ($^{79}Br$) and 621.3 ($^{81}Br$).

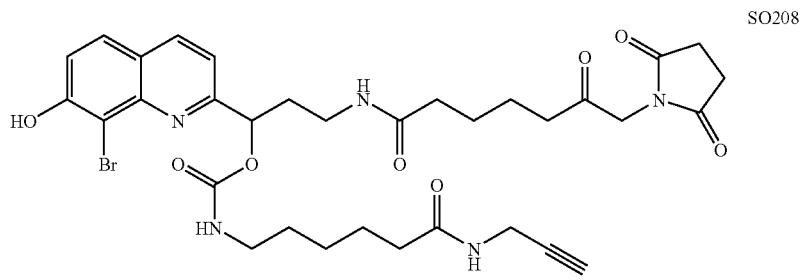

2,5-Dioxopyrrolidin-1-yl 14-(8-bromo-7-hydroxyquinolin-2-yl)-5,12,18-trioxo-13-oxa-4,11,17-triazatricos-1-yn-23-oate (SO208). To a stirred solution of 14-(8-Bromo-7-hydroxyquinolin-2-yl)-5,12,18-trioxo-13-oxa-4,11,17-triazatricos-1-yn-23-oic acid (15 mg, 0.024 mmol) in DMF (200 uL), were added N-(3-dimethylaminopropyl)-N'-ethylcarbodiimide hydrochloride (5.1 mg, 0.027 mmol). After 10 min, N-hydroxysuccinimide (3.1 mg, 0.027 mmol) were also add and the reaction mixture was stirred for 24 h at room temperature. The reaction mixture was mixed with $CHCl_3$ (500 uL) and washed with 5% citric acid (2×500 uL) and $H_2O$ (3×500 uL). The organic layer was dried by blowing a stream of Argon to yield an oily colorless product (15.3 mg, 0.021 mmol, 88%). This product was used for conjugation without further purification. MS-ESI (m/z): $[M+H]^+$ calculated for $C_{32}H_{39}BrN_5O_9$, 716.2 ($^{79}Br$) and 718.2 ($^{81}Br$); found 716.3 ($^{79}Br$) and 718.3 ($^{81}Br$).

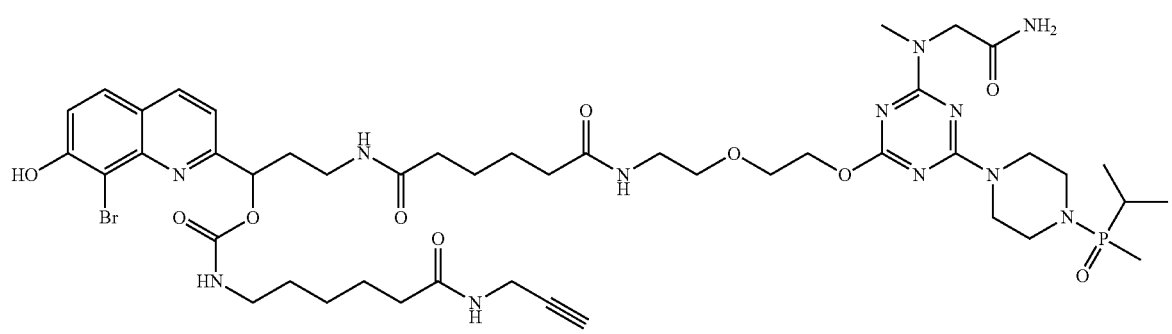

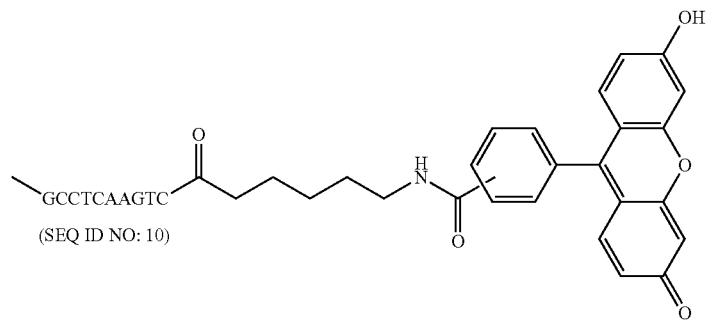

Photocaged inhibitor morpholino oligomer (SO214). Morpholino 10 mer 5'-GCCTCAAGTC-3' with 5' amine and 3' fluorescein modification was purchased from Gene-Tools, LLC and used without further purification. 100 nmol of the modified 10 mer was dissolved in aq. 0.1 M $Na_2B_4O_7$ solution, pH=8.5 (100 μL), and combined with 2,5-dioxopyrrolidin-1-yl 14-(8-bromo-7-hydroxyquinolin-2-yl)-5,12,18-trioxo-13-oxa-4,11,17-triazatricos-1-yn-23-oate (100 mM) in DMF (15 μL). The reaction was lyophilized to a volume of 50 uL and precipitated with 400 uL of acetone. After the formation of a pellet by centrifugation and removal of all liquids, the pellet was wash with 100 uL acetonitrile and lyophilized for 5 min to remove residual solvents. The pellet was dissolved in 100 uL water and dialyzed for 5 h to remove all salts. An orange powder was recovered (80 nmol, 80%) after dialysis and lyophilization. MS-ESI (m/z): $[M+H]^+$ calculated for $C_{184}H_{258}N_{69}O_{58}P_{10}Br$, 4755; found, 4758.

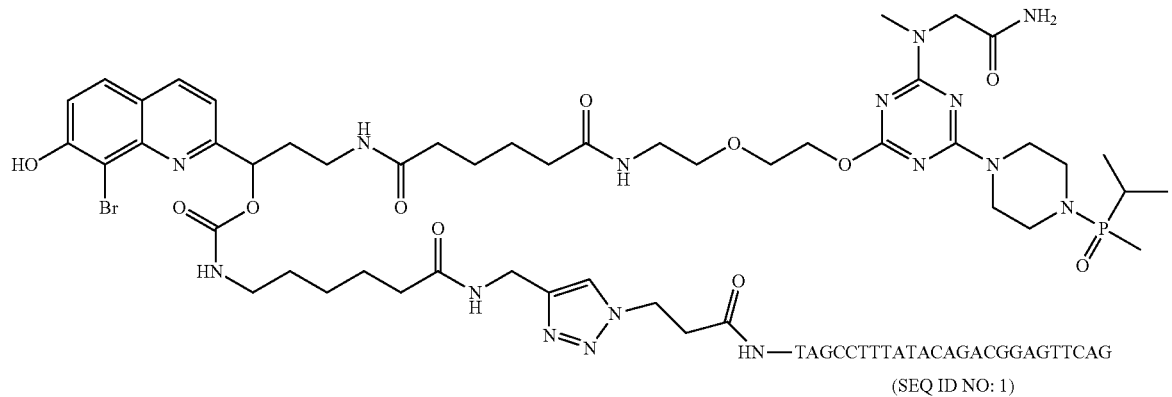

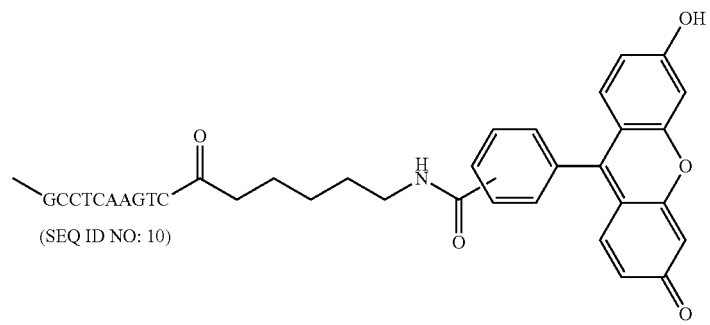

Caged ntl morpholino (SO216). The photocaged 10 mer (80 nmol) and azide-functionalized ntl morpholino 11 (80 nmol) were dissolved in aq. 100 mM $KH_2PO_4$, pH 8.0 (230 μL). To this mixture was added sodium ascorbate (99.0 μg, 500 nmol) in 25 μL of water, followed by TBTA (265 μg, 500 nmol), and CuI (95.2 μg, 500 nmol) in 50 μL of DMSO. The reaction mixture was briefly sonicated and stirred overnight at room temperature in the dark. Precipitate was removed from reaction crude by centrifugation. The supernatant was split and desalted over two Zeba Desalt size-exclusion columns (Pierce) according to manufacturer's instructions. The desired product was purified from the reaction mixture by adjusting pH of the solution to 11.5 with aq. 1 M NaOH and loading it onto a DNAPac PA-100 ion exchange HPLC column (Dionex, 9 mm×250 mm). Aqueous running buffers were A: 0.02 M NaOH, 1% ACN; B: 0.375 M $NaClO_4$ in 0.02 M NaOH and 1% ACN. Step-wise gradient was used with flow rate of 4 ml/min, the gradient was 7 to 17% B in 5 min, 17 to 20% B in 10 min, 20 to 50% B in 1 min, and 50% B for 9 min. Elution fractions were collected with the UV-VIS flow-cell lamp turned off to prevent photolysis. Fractions (1 mL) were collected every 15 sec, and buffered with aq. 1 M $NH_4OAc$, pH 5 (40 μL). The fractions containing fluoresceinated product were combined, and purified over a Zeba Desalt size-exclusion column (Pierce) according to manufacturer's instructions. Eluent volume was reduced in vacuo to 50 μL and the morpholinos were precipitated with acetone (400 μL). Morpholinos were pelleted on a microcentrifuge and supernatant was discarded. The pellet was washed with ACN (100 μL) and briefly lyophilized, affording an orange solid (6.5 nmol, 8% overall). MS-ESI (m/z): $[M+H]^+$ calculated for $C_{488}H_{732}BrN_{219}O_{161}P_{35}$, 13406; found, 13408.

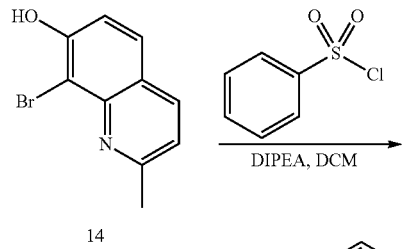

14

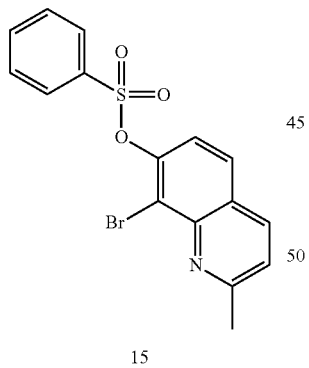

15

8-bromo-2-methylquinolin-7-yl benzenesulfonate (15). 8-bromo-2-methylquinolin-7-ol[3] (14, 1.10 g, 4.62 mmol) and N,N-diisopropylethylamine (1.19 g, 9.24 mmol) were dissolved in anhydrous DCM (10 mL), and the solution was cooled to 0° C. Benzenesulfonyl chloride (0.90 g, 5.10 mmol) in DCM (5 mL) was added over 10 min, and the reaction mixture was stirred for 14 h at room temperature under argon. Solvent was removed in vacuo, and residue was dissolved in EtOAc, washed twice with saturated aq. $NaHCO_3$, and dried over anhydrous $Na_2SO_4$. Solvent was removed in vacuo, and the residue was purified by $SiO_2$ column chromatography (hexanes/EtOAc=1/1) to yield 15 as a white solid (1.70 g, 4.49 mmol, 97% yield). $^1H$ NMR (400 MHz, $CDCl_3$) δ 8.05 (d, 1H, J=8.4 Hz), 7.98 (m, 1H), 7.96 (m, 1H), 7.76 (d, 1H, J=8.8 Hz), 7.70–7.66 (m, 1H), 7.60 (d, 1H, J=8.8 Hz), 7.55–7.51 (m, 2H), 7.35 (d, 1H, J=8.0 Hz), 2.79 (s, 3H). $^{13}C$ NMR (500 MHz, $CDCl_3$) δ 161.59, 148.07, 145.80, 136.57, 135.92, 134.83, 129.44, 128.91, 128.03, 126.12, 123.24, 121.95, 118.04, 25.92. MS-ESI (m/z): $[M+H]^+$ calculated for $C_{16}H_{13}BrNO_3S$, 378.0 ($^{79}Br$) and 380.0 ($^{81}Br$); found 378.0 ($^{79}Br$) and 379.9 ($^{81}Br$).

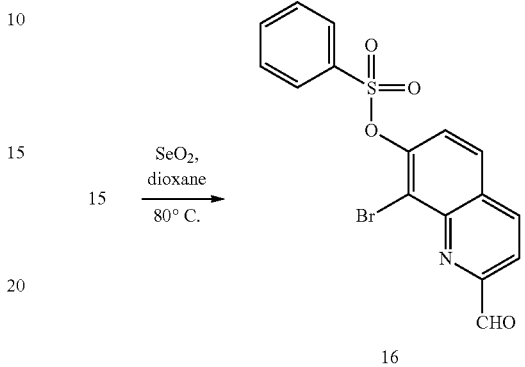

8-Bromo-2-formylquinolin-7-yl benzenesulfonate (16). A mixture of $SeO_2$ (500 mg, 4.51 mmol) and 1,4-dioxane (10 mL) was heated to over 80° C. 8-Bromo-2-methylquinolin-7-yl benzenesulfonate (15, 1.70 g, 4.49 mmol) in 1,4-dioxane (5 mL) was added. After stirring at 80° C. for 24 h, the reaction was cooled and vacuum filtered. The filtrate was collected and concentrated to yield a yellow solid. Purification by $SiO_2$ column chromatography ($CHCl_3$) gave 16 as a white solid (1.60 g, 4.08 mmol, 91% yield). $^1H$ NMR (500 MHz, $CDCl_3$) δ 10.25 (s, 1H), 8.37 (d, 1H, J=7.5 Hz), 8.09 (d, 1H, J=8.5 Hz), 7.99 (d, 2H, J=7.0 Hz), 7.91 (d, 1H, J=9.0 Hz), 7.79 (d, 1H, J=9.0 Hz), 7.72 (t, 1H, J=7.5 Hz), 7.57 (t, 2H, J=8.0 Hz). $^{13}C$ NMR (500 MHz, $CDCl_3$) δ 193.33, 153.80, 149.08, 146.10, 138.35, 135.82, 135.17, 129.79, 129.66, 128.99, 128.37, 125.61, 119.93, 118.51.

MS-ESI (m/z): $[M+H]^+$ calculated for $C_{16}H_{11}BrNO_4S$, 392.0 ($^{79}Br$) and 394.0 ($^{81}Br$); found 391.8 ($^{79}Br$) and 393.8 ($^{81}Br$).

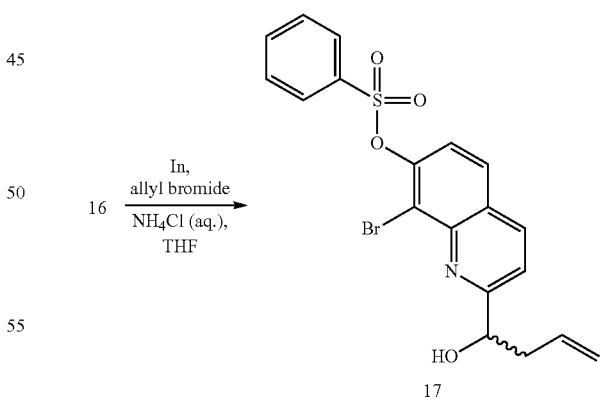

8-Bromo-2-(1-hydroxybut-3-enyl)quinolin-7-yl benzenesulfonate (17). A mixture of compound 16 (448 mg, 1.14 mmol), In powder (150 mg, 1.31 mmol) and allyl bromide (160 μL, 1.87 mmol) were stirred in a mixture of 10 mL THF and 10 mL aq. $NH_4Cl$ for 3 hours. THF was removed in vacuo, and residue was extracted with EtOAc and then dried over anhydrous $Na_2SO_4$. Solvent was removed in vacuo, and the residue was purified by $SiO_2$ column chromatography (hexanes/EtOAc=2/1) to yield 17 as a colorless oil (478 mg, 1.10 mmol, 96% yield). $^1$H NMR (500 MHz, CDCl$_3$) δ 8.13 (d, 1H, J=8.0 Hz), 7.96–7.93 (m, 2H), 7.76 (d, 1H, J=9.0 Hz), 7.68 (t, 1H, J=8.5 Hz), 7.54–7.50 (m, 3H), 7.42 (d, 1H, J=8.5 Hz), 5.89–5.80 (m, 1H), 5.11–5.03 (m, 2H), 4.97 (s, 2H), 2.73–2.69 (m, 1H), 2.54–2.48 (m, 1H). $^{13}$C NMR (500 MHz, CDCl$_3$) δ 163.40, 148.17, 144.08, 137.34, 135.61, 134.86, 133.88, 129.40, 128.67, 128.01, 126.84, 122.47, 119.53, 118.22, 118.12, 72.24, 42.34. MS-ESI (m/z): [M+H]$^+$ calculated for C$_{19}$H$_{17}$BrNO$_4$S, 434.01 ($^{79}$Br) and 436.00 ($^{81}$Br); found 434.11 ($^{79}$Br) and 436.10 ($^{81}$Br).

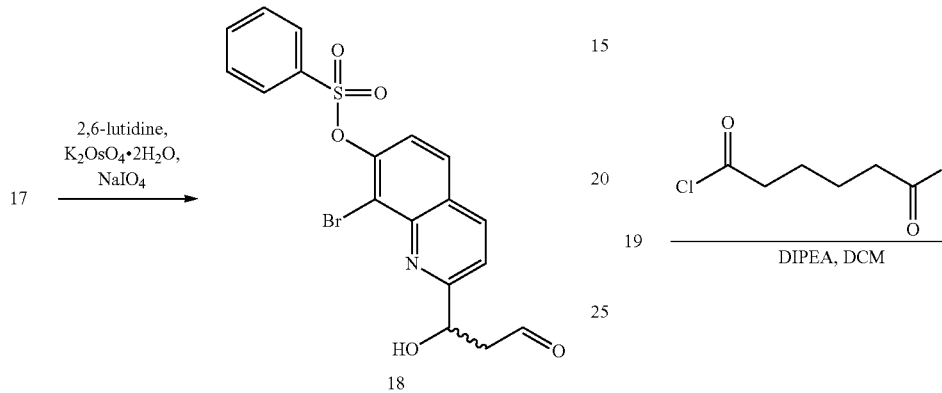

8-Bromo-2-(1-hydroxy-3-oxopropyl)quinolin-7-yl benzenesulfonate (18). To a solution of compound 17 (330 mg, 0.760 mmol) in dioxane-water (3:1, 8 mL) were added 2,6-lutidine (0.177 mL, 1.73 mmol), K$_2$O$_s$O$_4$·2 H$_2$O (6 mg, 0.016 mmol), and NaIO$_4$ (655 mg, 3.06 mmol). The reaction was stirred at 25° C. and monitored by TLC. After the reaction was complete, water (10 mL) and CH$_2$Cl$_2$ (20 mL) were added. The organic layer was separated, and the aqueous layer was extracted by DCM (10 mL) three times. The organic layers were pooled, washed with brine, and dried over Na$_2$SO$_4$. The solvent was removed, and the product was purified with SiO$_2$ column chromatography (hexanes/EtOAc=2/3) to afford aldehyde 18 (250 mg, 0.573 mmol, 75%) as a colorless oil. MS-ESI (m/z): [M+H]$^+$ calculated for C$_{18}$H$_{15}$BrNO$_5$S, 435.99 ($^{79}$Br) and 437.98 ($^{81}$Br); found 436.04 ($^{79}$Br) and 437.97 ($^{81}$Br).

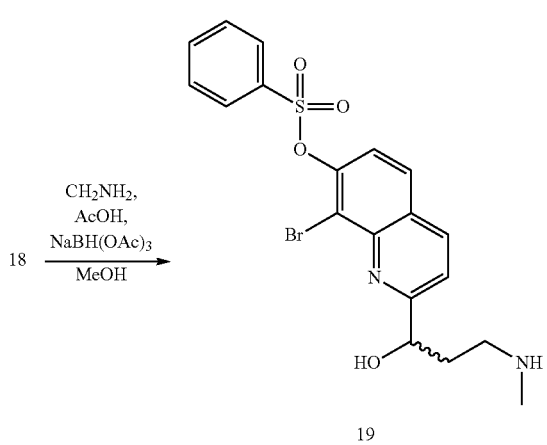

8-Bromo-2-(1-hydroxy-3-(methylamino)propyl)quinolin-7-yl benzenesulfonate (19). To a solution of compound 18 (190 mg, 0.435 mmol) in MeOH (1 mL) were added methyl amine (0.04 mL, 0.462 mmol), HOAc (0.005 mL), and NaBH(OAc)$_3$ (200 mg, 0.943 mmol). The reaction was stirred at 25° C. for 20 h. After the reaction was complete, 1 N HCl (0.1 mL) was added to the reaction mixture and then neutralized with saturated aq. NaHCO$_3$. The resulting mixture was extracted with EtOAc, and the organic layers were pooled, washed with brine, and dried over Na$_2$SO$_4$. Solvent was removed in vacuo to afford 19 (160 mg, 0.355 mmol, 81%) as a colorless oil, which was used without further purification. MS-ESI (m/z): [M+H]$^+$ calculated for C$_{19}$H$_{20}$BrN$_2$O$_4$S, 451.03 ($^{79}$Br) and 453.03 ($^{81}$Br); found 450.89 ($^{79}$Br) and 453.01 ($^{81}$Br).

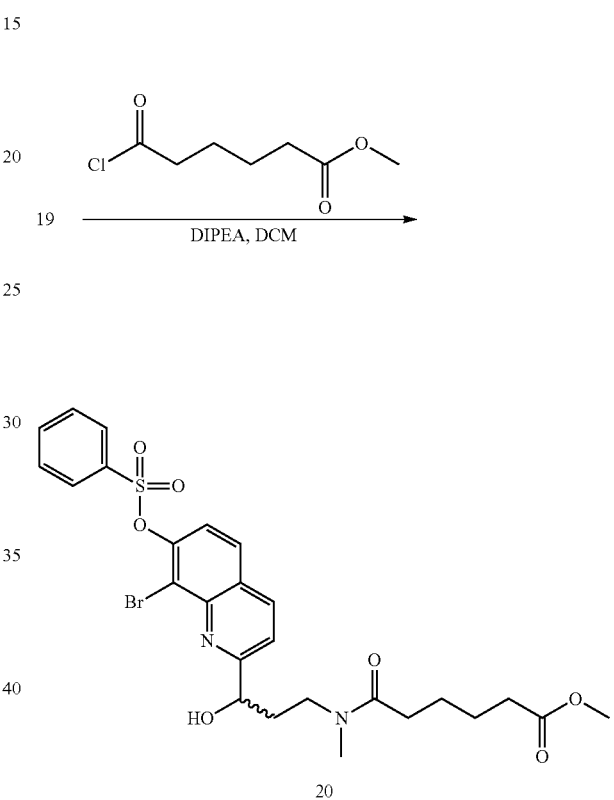

Methyl 6-(((3-(8-bromo-7-(phenylsulfonyloxy)quinolin-2-yl)-3-hydroxypropyl)methyl) amino)-6-oxohexanoate (20). Compound 19 (160 mg, 0.355 mmol) were dissolved in anhydrous DCM (5 mL), and the solution was cooled to 0° C. Methyl adipoyl chloride (66 mg, 0.37 mmol) was added over 5 min, and the reaction mixture was stirred for 6 h at room temperature under nitrogen. Solvent was removed in vacuo, and residue was dissolved in EtOAc, washed twice with saturated aq. NaHCO$_3$, and dried over anhydrous Na$_2$SO$_4$. Solvent was removed in vacuo, and the residue was purified by SiO$_2$ column chromatography (CHCl$_3$/acetone=1/1) to yield 20 as a colorless oil (124 mg, 0.209 mmol, 59%). $^1$H NMR (500 MHz, CDCl$_3$) δ8.23–8.16 (m, 1H), 7.99–7.96 (m, 2H), 7.84–7.79 (m, 1H), 7.73–7.68 (m, 2H), 7.62–7.45 (m, 3H), 5.40–5.16 (m, 1H), 4.92–4.85 (m, 1H), 3.78–3.72 (m, 1H), 3.66 (m, 3H), 3.46–3.40 (m, 1H), 2.96 (m, 3H), 2.35–2.28 (m, 3H), 2.23–2.04 (m, 3H), 1.67–1.54 (m, 4H).

MS-ESI (m/z): [M+H]$^+$ calculated for C$_{26}$H$_{30}$BrN$_2$O$_7$S, 593.10 ($^{79}$Br) and 595.09 ($^{81}$Br); found 593.11 ($^{79}$Br) and 595.10 ($^{81}$Br).

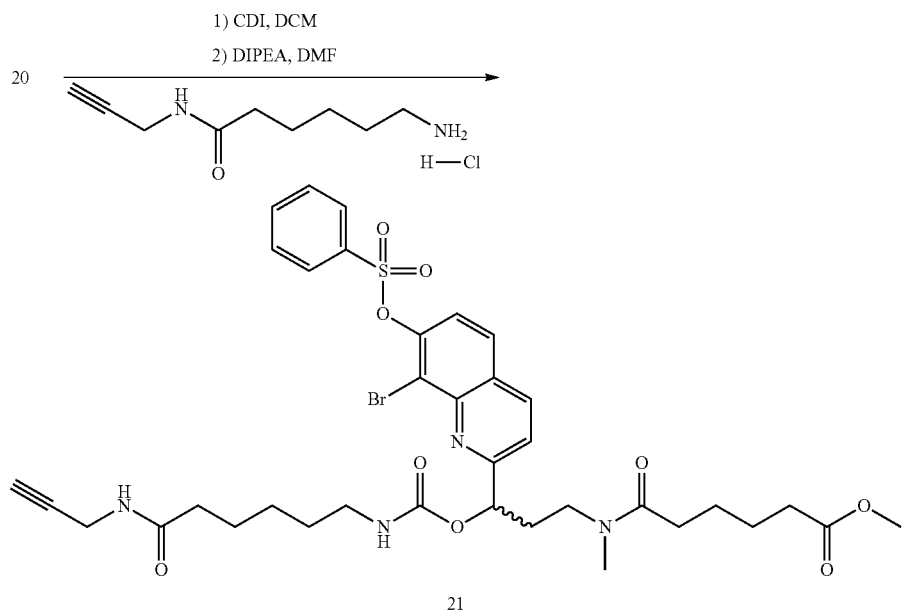

Methyl 14-(8-bromo-7-(phenylsulfonyloxy)quinolin-2-yl)-17-methyl-5,12,18-trioxo-13-oxa-4,11,17-triazatricos-1-yn-23-oate (21). Compound 20 (114 mg, 0.192 mmol) was dissolved in anhydrous DCM (1 mL) and added to 1,1'-carbonyl diimidazole (46.7 mg, 0.288 mmol) in anhydrous DCM (1.5 mL). The reaction mixture was stirred for 4 h at room temperature under nitrogen, diluted with DCM, washed two times with water, and dried over anhydrous $MgSO_4$. Solvent was removed in vacuo, and the residue was purified by $SiO_2$ column chromatography ($CHCl_3$/acetone=1/1) to yield the imidazole carbamate as a colorless gum (116 mg, 0.169 mmol, 88%). MS-ESI (m/z): [M+H]$^+$ calculated for $C_{30}H_{32}BrN_4O_8S$, 687.1 ($^{79}$Br) and 689.1 ($^{81}$Br); found 687.2 ($^{79}$Br) and 689.2 ($^{81}$Br). The imidazole carbamate (66 mg, 0.096 mmol) was then dissolved in anhydrous DMF (1.5 mL) and N,N-diisopropylethylamine (33 μL, 0.190 mmol). To this mixture was added 6-oxo-6-(prop-2-ynylamino)hexan-1-aminium hydrochloride salt (36 mg, 0.177 mmol) in anhydrous DMF (1.4 mL). The reaction mixture was stirred overnight at room temperature under nitrogen. Solvent was then removed in vacuo, and the crude material was re-dissolved in toluene and evaporated to dryness again. The resulting yellow gum was then dissolved in $CHCl_3$, washed once with 1 N HCl, once with 5% saturated aq. $NaHCO_3$, once with brine, and dried over anhydrous $MgSO_4$. Solvent was removed in vacuo, and the residue was purified by $SiO_2$ column chromatography ($CHCl_3$/acetone, stepwise gradient from 4/1 to 2/1) to yield 21 as a viscous colorless gum (70 mg, 0.089 mmol, 93%).

$^1$H NMR (500 MHz, CDCl3) δ 8.20–8.15 (m, 1H), 7.99–7.97 (m, 2H), 7.81–7.77 (m, 1H), 7.72–7.71 (m, 1H), 7.61–7.52 (m, 4H), 6.12 (m, 1H), 5.95–5.88 (m, 1H), 5.31–5.14 (m, 1H), 4.03 (m, 2H), 3.66 (s, 3H), 3.59–3.55 (m, 1H), 3.49 (m, 2H), 3.25–3.12 (m, 2H), 2.99–2.91 (m, 3H), 2.40–2.18 (m, 8H), 1.68–1.25 (m, 10H). MS-ESI (m/z): [M+H]$^+$ calculated for $C_{36}H_{44}BrN_4O_9S$, 787.20 ($^{79}$Br) and 789.20 ($^{81}$Br); found 787.30 ($^{79}$Br) and 789.30 ($^{81}$Br).

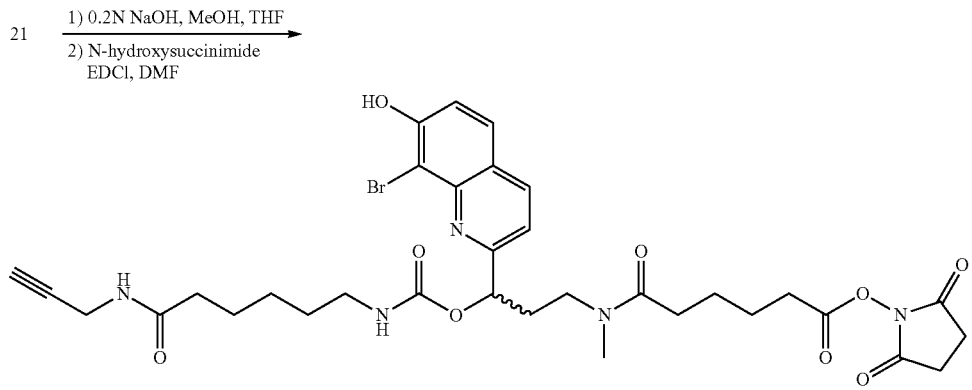

2,5-Dioxopyrrolidin-1-yl 14-(8-bromo-7-hydroxyquinolin-2-yl)-17-methyl-5,12,18-trioxo-13-oxa-4,11,17-triazatricos-1-yn-23-oate (13). Compound 21 (26 mg, 0.033 mmol) was dissolved in MeOH (0.25 mL) and THF (0.25 mL) and added to 0.4 N NaOH (0.5 mL). The reaction was monitored by TLC, and upon completion, MeOH and THF were removed in vacuo. The residual solution was loaded onto Toyopearl Super-Q resin (1 mL), washed three times with wash solution (0.4 N NaOH, 50% $CH_3CN$) and two times with water. The carboxylic acid was eluted from the resin with 1 mL of aq. 5% HOAc/50% $CH_3CN$. The eluent was lyophilized to give the carboxylic acid as a colorless gum (17 mg, 0.027 mmol, 82%). MS-ESI (m/z): $[M+H]^+$ calculated for $C_{29}H_{38}BrN_4O_7$, 633.2 ($^{79}Br$) and 635.2 ($^{81}Br$); found 633.3 ($^{79}Br$) and 635.3 ($^{81}Br$). To synthesize compound 13, the carboxylic acid (16 mg, 0.025 mmol) was dissolved in 0.5 mL DMF, and EDCI (10 mg, 0.052 mmol) and N-hydroxysuccinimide (6 mg, 0.052 mmol) were then added. The resulting mixture was stirred in the dark for 48 h. Solvent was then removed in vacuo, and the crude material was re-dissolved in toluene and evaporated to dryness again. The resulting yellow gum was then dissolved in $CHCl_3$, washed once with aq. 15% citric acid, and dried over anhydrous $MgSO_4$. Solvent was removed in vacuo, and the residue was purified by $SiO_2$ column chromatography ($CHCl_3$/acetone, stepwise gradient from 3/1 to 3/2) to yield 13 as a thick colorless gum (9 mg, 0.012 mmol, 48%). $^1H$ NMR (500 MHz, $CDCl_3$) δ 8.12–8.07 (dd, 1H, $J_1$=8.5 Hz, $J_2$=9 Hz), 7.69 (t, 1H, J=8.5 Hz), 7.40–7.37 (dd, 1H, $J_1$=5 Hz, $J_2$=8 Hz), 7.32–7.29 (dd, 1H, $J_1$=3 Hz, $J_2$=9 Hz), 6.56–6.30 (m, 1H), 6.61–5.80 (m, 2H), 5.08 (m, 1H), 4.04 (m, 2H), 3.58–3.41 (m, 2H), 3.27–3.13 (m, 2H), 2.99–2.95 (m, 3H), 2.84 (br, 4H), 2.63 (t, 1H, J=7 Hz), 2.56 (t, 1H, J=7.5 Hz), 2.45–2.34 (m, 2H), 2.24–2.17 (m, 4H), 1.79–1.25 (m, 11H). HRMS (TOF MS ES+) (m/z): $[M+Na]^+$ calculated for $C_{33}H_{40}BrN_5NaO_9$, 752.1907 ($^{79}Br$); found 752.1898 ($^{79}Br$).

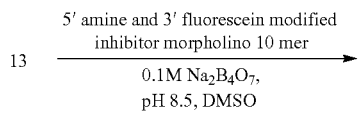

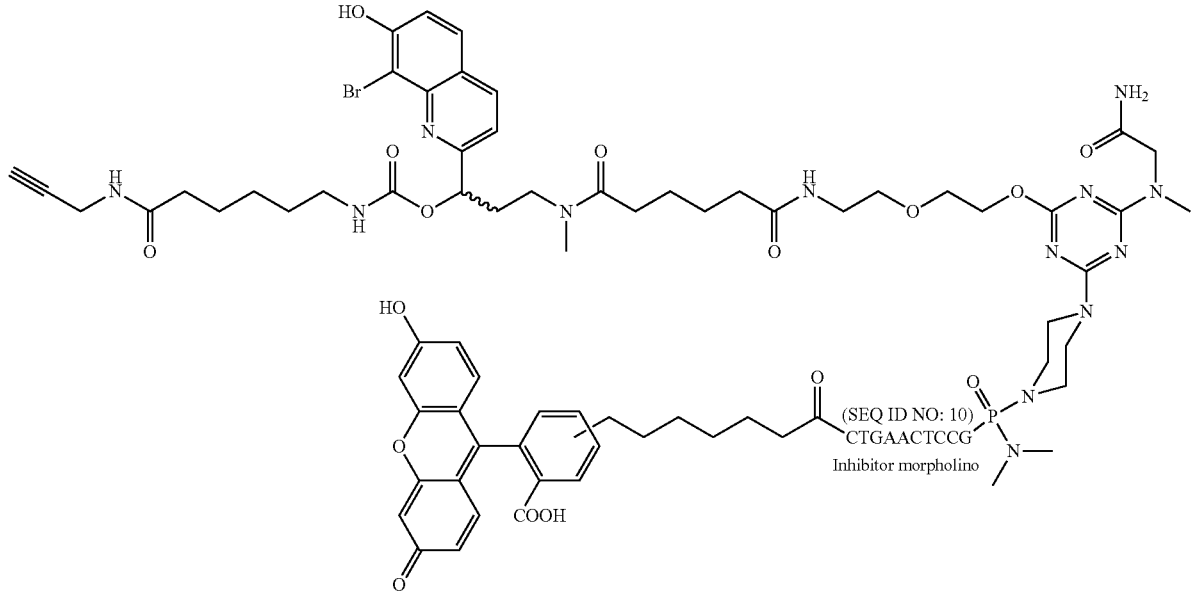

BHQ-conjugated, fluorescent ntl MO inhibitor (23a). Synthetic procedures for the BHQ-conjugated ntl MO inhibitors were analogous to those described for 7e, using the identical fluorescinated oligomer (5'-GCCTCAAGTC-3').
Compounds 23a was recovered as a yellow solid (75 nmol, 75%).
MS-ESI (m/z): [M+H]$^+$ calculated for 23a, $C_{185}H_{261}N_{69}O_{58}P_{10}Br$, 4769; found, 4772.
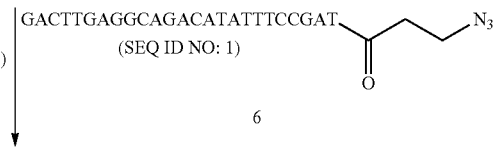
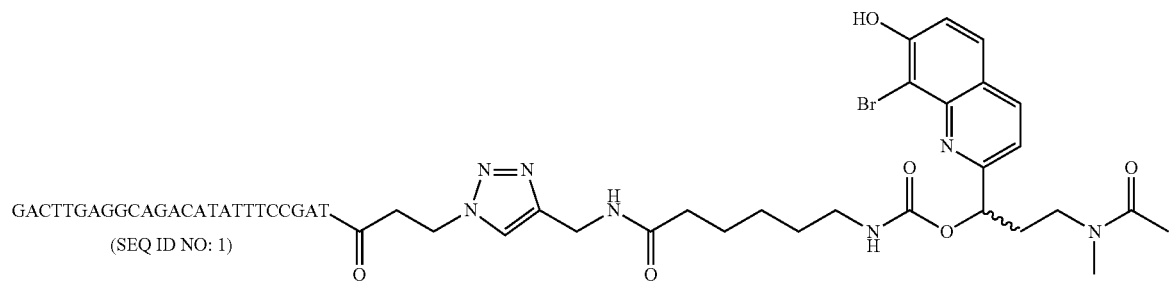
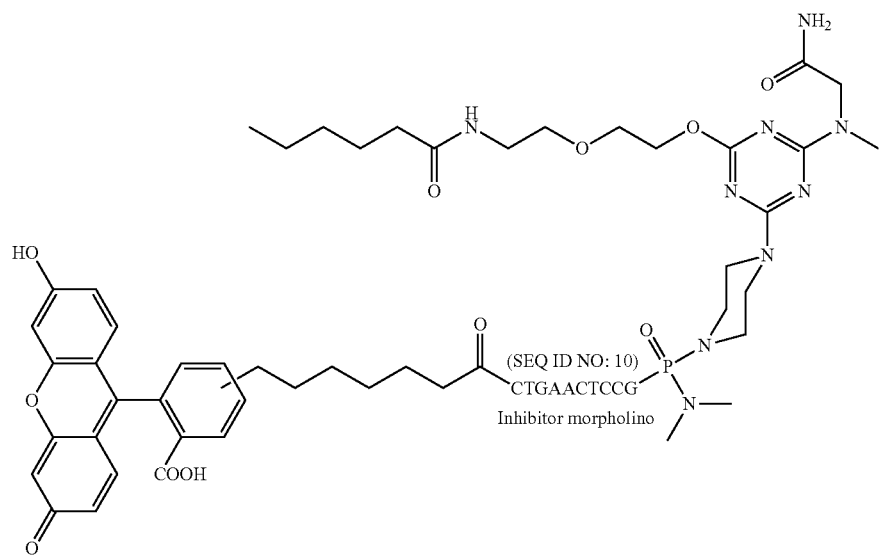

BHQ-based, fluorescent ntl cMO (22a). Synthetic procedures for the BHQ-based ntl cMO were analogous to those described for 8e, using the BHQ functionalized inhibitor oligomer 23a (75 nmol) and the azide-functionalized ntl MO 6 (75 nmol). cMO 22a was recovered as a yellow solid (10 nmol, 10% overall yield). MS-ESI (m/z): [M+H]$^+$ calculated for 22a, $C_{489}H_{734}N_{219}O_{161}P_{35}Br$, 13417; found, 13422.

$Na_2B_4O_7$, pH=8.5 (100 μL) and combined with BHQ linker 13 (0.80 mg, 1.5 μmol) in DMSO (15 μL). The reaction was shaken overnight in the dark. The reaction was diluted to 500 μL with water and passed through a NAP™5 size exclusion column (GE Healthcare) according to the manufacturer's instructions. Product-containing fractions (~1 mL) was con-

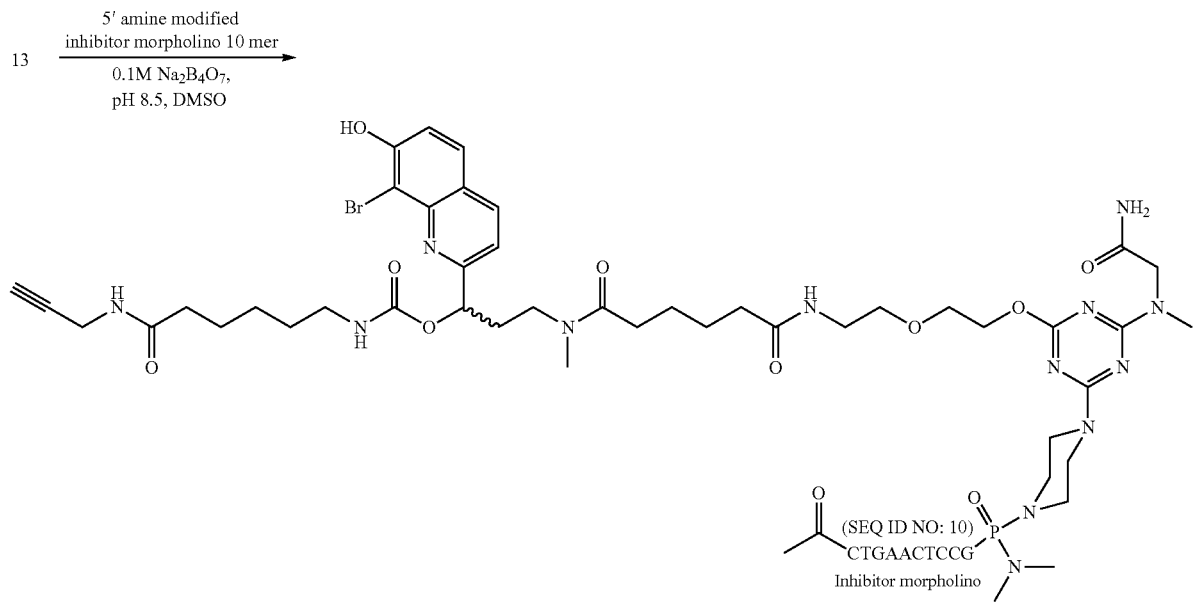

BHQ-conjugated, non-fluorescent ntl MO inhibitor (23b). Synthetic procedures for the BHQ-conjugated ntl MO inhibitors were analogous to those described for 7e with the following modifications. An identical inhibitor MO sequence (5'-GCCTCAAGTC-3') was used, except the oligomer contained 5' amine but not 3' fluorescein modifications. The inhibitory oligomer (100 nmol) was dissolved in 0.1 M centrated to 400 μL by lyophilization, acidified with 4 μL of HOAc, and washed with $CHCl_3$ (3×400 μL) and EtOAc (2×400 μL). The remaining aqueous solution was neutralized with $NH_4OH$ (10%, 20 μL) and lyophilized to give 23b as a white solid (45 nmol, 45%). MS-ESI (m/z): [M+H]$^+$ calculated for 23b $C_{161}H_{246}N_{68}O_{50}P_{10}Br$, 4324; found, 4324.

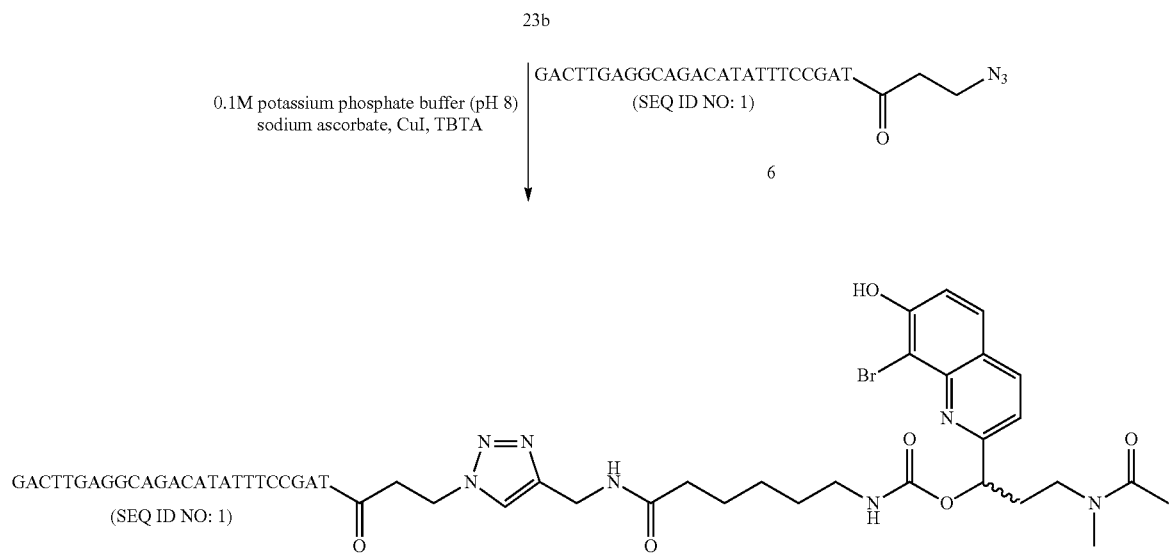

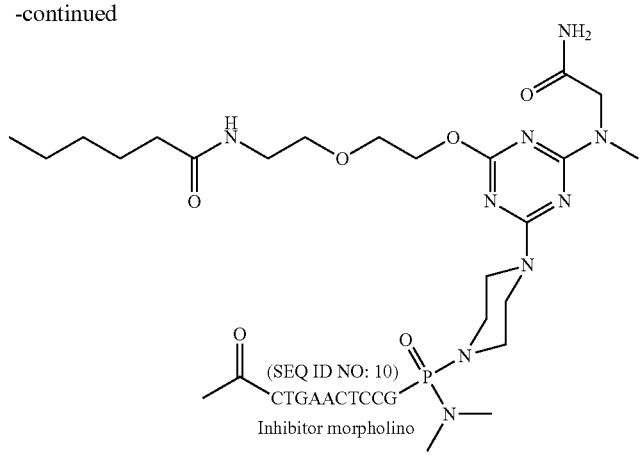

22b

BHQ-Based, Non-Fluorescent ntl cMO (22b). The inhibitory oligomer 23b (45 nmol) and azide-functionalized ntl MO 6 (45 nmol) were dissolved in phosphate buffer (KH$_2$PO$_4$, pH 8.0, 230 µL). To this mixture was added sodium ascorbate (99.0 µg, 500 nmol) in 25 µL of water, followed by TBTA (265 µg, 500 nmol), and CuI (95.2 µg, 500 nmol) in 50 µL of DMSO. The reaction mixture was briefly sonicated and stirred overnight at room temperature in the dark. Precipitate was removed from reaction mixture by centrifugation, and the supernatant was diluted to 800 µL, split and passed through two NAP™5 size exclusion columns (GE Healthcare) according to the manufacturer's instructions. The desired product was purified from the reaction mixture by adjusting the solution pH to 11.5 with aq. 1 M NaOH and loading it onto a DNAPac PA-100 ion-exchange HPLC column (Dionex, 9 mm×250 mm). Aqueous running buffers were A: 0.02 M NaOH, 1% CH$_3$CN; B: 0.375 M NaClO$_4$ in 0.02 M NaOH and 1% CAN, and a step-wise gradient was used to separate the product and starting materials, with specific conditions determined by column capacity. A representative purification gradient is: 7 to 15% B in 5 min, 15 to 17% B in 10 min, 17 to 50% B in 1 min, and 50% B for 9 min (flow rate of 4 mL/min). Elution fractions were collected with the UV-VIS flow-cell lamp turned off to prevent photolysis. Fractions (1 mL) were collected every 15 sec and buffered with aq. 1 M NH$_4$OAc, pH 5 (40 µL). Product-containing fractions were identified by absorbance using a Nanodrop spectrophotometer (Thermo Scientific), combined, and lyophilized to dryness. The residue was redissolved in 400 µL of water and passed through a NAP™5 size exclusion column (GE Healthcare). Eluent volume was reduced in vacuo to 50 µL and the MOs were precipitated with acetone (400 µL). After centrifugation, the supernatant was discarded and the MO pellet was washed with CH$_3$CN (100 µL) and lyophilized to dryness. cMO 22b was recovered as a white solid (7 nmol, 7% overall yield). MS-ESI (m/z): [M+H]$^+$ calculated for 22b C$_{465}$H$_{719}$BrN$_{218}$O$_{153}$P$_{35}$, 12972; found, 12971.

Example 4

Biophysical Studies of Caged Morpholinos for in vivo Activity Optimization. Our simplified synthetic route has also facilitated our efforts to determine the biophysical parameters required for optimum caged morpholino design. Although the efficacy of our ntl cMO in zebrafish demonstrates that morpholino activity can be blocked by an intramolecular 10-base inhibitor, other caged structures may be more effective. It is also important to note that the linkers resulting from our two synthetic procedures differ in structure, and these changes may influence caged morpholino properties. To establish guidelines for the design of future reagents, we therefore conducted a comprehensive analysis of how inhibitor size (10, 12, 14, and 16 bases) and the complementary region (5' end versus the middle of the 25-base targeting morpholino) influence the biophysical properties and in vivo activities of caged morpholinos.

We first determined the energetics of intermolecular morpholino/inhibitor and morpholino/RNA binding by dissolving a 1:1 ratio of the ntl MO and various oligomers in buffer (20 mM HEPES, pH 7.0, 100 mM KCl, 10 mM MgCl$_2$, 0.1 mM EDTA) and measuring their temperature-dependent changes in 260-nm absorbance. Free energy values were then obtained from these melting curves using MeltWin 3.0 software. We similarly ascertained the energetics of intramolecular morpholino/inhibitor interactions by synthesizing the corresponding ntl MO conjugates through our optimized synthetic procedure. A DMNB-free linker was used for these studies to prevent photolysis during the melting curve measurements, and these experiments revealed approximately a 4.5 kcal/mol difference in binding energy between the inter- and intramolecular interactions, largely independent of the inhibitor sequence.

We next synthesized the complete panel of caged morpholino structures using a DMNB-based linker and evaluated their efficacies in vivo. Each ntl cMO was injected to zebrafish embryos at the one-cell stage (230 fmol/embryo) and irradiated with 360 nm for 10 seconds at 3 hpf. The embryos were cultured for an additional day and then scored according to the four phenotypic classes described above (see FIG. 3). Our findings show that linker structure can significantly alter caged morpholino activity, as the 10-base sequence utilized in our first ntl cMO was much less effective in our new reagent. In fact, caged morpholinos that contained inhibitory sequences complementary to the middle region of the 25-base targeting oligomer were significantly less active upon photolysis than energetically comparable inhibitors complementary to the 5' end. We attribute this activity difference to interactions between the cleaved linkers that might promote morpholino/inhibitor annealing even after photolysis. More importantly, our data established that optimum in vivo activities (i.e. greatest activity differential between uncaged and caged states) are observed when the intermolecular morpholino/inhibitor free energy of binding is approximately −13 kcal/mol. Using these guidelines we have prepared caged morpholinos against other genes such as flh, etsrp, and sox32 and demonstrated their ability to convey light-dependent midline patterning, vasculature, and heart defects, respectively.

Materials and Methods

Zebrafish Aquaculture and Husbandry. Adult zebrafish (wild-type AB strain) were acquired from the Zebrafish International Resource Center. Embryos used in these studies were obtained by natural matings and cultured in E3 embryo medium at 28.5° C. according to standard procedures.[39]

MO Microinjections. Various MO, MO/inhibitor duplex, and cMO solutions containing 0.1% (w/v) phenol red were prepared and microinjected at 1 or 2 nL/embryo. For example, to inject 115 fmol of MO, 2 nL of a 57.5 μM solution containing 0.1% (w/v) phenol red was injected into each zebrafish embryo at the one-cell stage. All embryo injections were done according to standard procedures, and the embryos were subsequently cultured in E3 medium at 28.5° C. For two photon experiments, solutions containing 1.25 mM HCC-NPE-Dextran, 0.1% (w/v) phenol red, with or without 57.5 μM cMO 22b were injected at 2 nL/embryo.

Photolysis of cMOs in Vitro. Photolysis reactions were performed by dissolving 1 nmol of cMO hairpin in water (2 μL) and irradiating for 1 min using a Leica DM4500B compound microscope equipped with an A4 filtercube (Ex: 360 nm, 40-nm bandpass) and 20× water-immersion objective (0.50 NA, 13 mW/cm$^2$ intensity at 360 nm). Longer irradiation times did not improve reaction yields. The solutions were then adjusted to pH 11.5 with 0.02 M NaOH and analyzed by HPLC using a DNAPac PA-200 ion-exchange column (Dionex, 4 mm×250 mm). Aqueous running buffers were A: 0.02 M NaOH, 1% ACN; B: 0.375 M NaClO$_4$ in 0.02 M NaOH and 1% ACN. HPLC gradient was 7 to 50% B in 27 min at 1.2 mL/min.

Photoactivation of cMOs in Vivo. Zebrafish embryos between the 64- and 256-cell stages were arrayed in an agarose microinjection template. Mercury lamp light was focused onto the individual embryos for 10 sec using a Leica DM4500B compound microscope equipped with an A4 filtercube and a 20×water-immersion objective. Embryos were oriented with the animal pole facing the light source. Following photoactivation, embryos were cultured in E3 embryo medium at 28.5° C.

Two-Photon Irradiation of cMOs. Two-photon cMO photoactivation in zebrafish embryos was performed on an upright two-photon confocal microscope (Ultima XY, Prairie Technologies, Inc., Middleton, Wis.) equipped with two Ti:sapphire lasers (Mai Tai HP, Spectra Physics, Mountain View, Calif.) and a 40 ×(0.8 NA) water-immersion objective (LUMPlanFI/IR, Olympus America, Center Valley, Pa.). Using 820-nm illumination from the first laser (10 mW at back focal plane of the objective), two initial images were collected for each embryo: an epifluorescence image (bandpass: 525 nm center, 70 nm FWHM), and an infrared gradient contrast image (820-nm illumination).[40] Using the gradient contrast image, an 80 μm×60 μm×50 μm region of interest (ROI) was selected for photoactivation. The ROI was then illuminated for 2 minutes at 750 nm (65 mW at back focal plane of the objective) with the second laser. Following photoactivation, the embryo was re-imaged with 820-nm illumination. Following two-photon irradiation, embryos were cultured in E3 embryo medium at 28.5° C.

Brightfield and Fluorescence Microscopy. Chorions were manually removed from 1 day post fertilization (dpf) embryos and embryos were immobilized in E3 medium containing 0.7% (w/v) low-melt agarose and 0.05% (w/v) tricaine. Brightfield images were obtained at 5× with a Leica MZFLIII fluorescence stereoscope equipped with a Leica DC300F digital camera. Differential interference contrast images and time-lapse movies were obtained with a Leica DM4500B fluorescence microscope equipped with a 10× (0.25 NA) objective and a QImaging Retiga-SRV digital camera. Fluorescence images were also obtained with this equipment and a CFP filterset (excitation: 436/20 nm; emission: 480/40 nm). Embryos were segregated into 4 groups: Group 1—strong no-tail phenotype: absence of tail tissues and notochord, U-shaped somites, somite fusion immediately posterior of the yolk extension. Group 2—weak no-tail phenotype: truncated tail structures, absence of notochord, U-shaped somites, somites extend past the yolk extension. Group 3—very weak no-tail phenotype: truncation of anterior-posterior axis, notochord present but incompletely vacuolated, wild-type number of chevron-shaped somites. Group 4—wild-type.

Determination of MO Duplex Binding Energies. For intermolecular MO duplexes, the complementary oligomers (0.5 μM, 1:1 molar ratio) in buffer (100 mM KCl, 20 mM HEPES, 10 mM MgCl$_2$, 0.1 mM EDTA, pH 7.0, 1 mL) were denatured at 95° C. for 5 min. Thermal denaturation curves were obtained by monitoring temperature-dependent changes in absorbance of 260-nm light using a Varian Cary 300 spectrophotometer (annealing at 0.5° C./min). The hypochromicity curves were fitted to a sigmoidal function, and thermodynamic parameters were calculated using the non-self complementary algorithm in MeltWin 3.0b software. Binding free energies were calculated at 28° C. For intermolecular MO/RNA duplexes, the complementary MO and RNA oligomers were used in a 2:1 molar ratio to minimize hypochromicity changes due to RNA self-annealing. For intramolecular duplexes, thermodynamic parameters were calculated using the hairpin algorithm in MeltWin 3.0b software. Predicted oligomer melting temperature was calculated using the assumption:

$$T_m = (\#A + \#T)*2 + (\#G + \#C)*4.$$

Western Blot Analysis. At bud stage (10 hpf), wild-type and MO-injected embryos were dechorinated with Pronase (1 mg/mL) for 10 min at 28° C. Embryos were transferred to microcentrifuge tubes and homogenized with a pipette in TM1 buffer (180 μL/sample; 100 mM NaCl, 5 mM KCl, 5 mM HEPES pH 7.0, 1% (w/v) PEG-200,000) containing protease inhibitors (1 mM PMSF, 5 mg/mL complete Mini protease inhibitor cocktail, EDTA-free (Roche)) to remove yolks. Following centrifugation (500×g, 5 min, 4° C.), the TM1 solution was replaced and the pelleted cells were homogenized again with a pipette and re-centrifuged. Eighteen de-yolked embryos from each experimental condition were vortexed in SDS-PAGE loading buffer (50 μL/sample; 100 mM Tris-HCl pH 6.8, 330 mM 2-mercaptoethanol, 4% (w/v) SDS, 20% (v/v) glycerol, 100 mM DTT), sonicated for 1 min, and heated to 100° C. for 5 min. The lysates were resolved on a 4-12% Bis-Tris gradient acrylamide gel (five embryos/lane) and blotted onto nitrocellulose according to standard protocols. Anti-Ntl antibody was used at a 1:2,000 dilution in 1× PBS containing 0.1% (v/v) Tween 20 and 0.2% (w/v) I-Block (Roche). The anti-Ntl antibody was then detected using a horseradish peroxidase-conjugated anti-rabbit IgG antibody (GE) at a 1:10,000 dilution and the SuperSignal West Dura Extended Duration Substrate kit (Pierce) according to the manufacturer's instructions. The chemiluminesense from the membrane was digitally imaged (ChemiDoc XRS, Biorad) and band intensity was measured with Quantity One 4.5 software. The nitrocellulose membranes were then re-probed with mouse anti-β-actin (sc-8432, Santa Cruz Biotechnology at a 1:250 dilution; or clone AC-15, Sigma at a 1:10,000 dilution) and horseradish peroxidase-conjugated anti-mouse IgG (GE; 1:10,000 dilution) antibodies to normalize for loading differences between lanes.

Gel-Shift Analysis of MO/Inhibitor Exchange with RNA. Targeting and inhibitory oligomers corresponding to ntl cMOs 8a and 8e (5 μM, 1:1 molar ratio) in buffer (100 mM KCl, 20 mM HEPES, 10 mM MgCl$_2$, 0.1 mM EDTA, pH 7.0, 28 μL) were denatured at 95° C. for 2 min and annealed by cooling to 28° C. over 15 min. The complementary, 3'-fluoresceinated 25-base RNA (3 μM in above buffer, 2 μL) was then added to the annealed MO duplex solution to achieve a final RNA concentration of 0.2 μM. The mixture of oligomers was incubated at 28° C. for either 1 or 10 min and chilled to 4° C. on ice. The "0 min" sample was prepared by adding the RNA to the annealed MO duplex solution at 4° C., and the MO-RNA duplex was prepared by heat denaturation and annealing, as was done with the MO/inhibitor duplexes. All samples were then immediately mixed with chilled loading dye (6×: 60% glycerol, 0.1 M Tris-HCl, 90 mM boric acid, 1 mM EDTA, 0.9 mM xylene cyanol, pH 8.4) and resolved on a 15% Tris-borate-EDTA acrylamide gel at 200 V for 20 min at 4° C. After electrophoresis, the acrylamide gel was analyzed with a GE Typhoon imager (488-nm excitation, 580-nm emission).

What is claimed is:

1. A bifunctional linker having the structure:

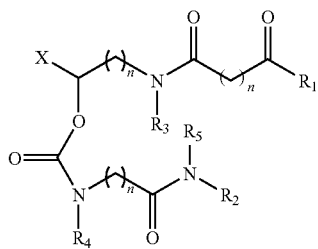

I where X is a photocleavable moiety;

R1 and R2 are independently selected from succinimide (NHS ester):

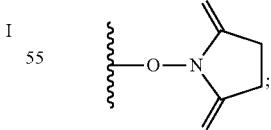

isothiocyanate:

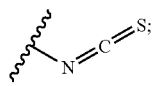

propargyl:

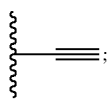

iodoacetamide:

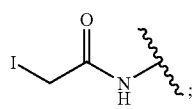

maleimide:

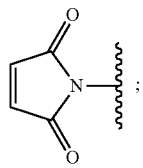

azide:

and terminal alkene:

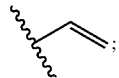

R3, R4 and R5 are independently selected from H and C1-C6 lower alkyls; and n is an integer from 0 to 10.

2. The linker of claim 1, wherein X is a UV excited moiety.

3. The linker of claim 2, wherein X is a 1,2-dimethoxy-4-nitrobenzyl moiety;

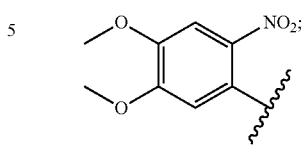

or a nitrobenzyl moiety.

4. The linker of claim 1, wherein X is a multiphoton activated moiety.

5. The linker of claim 4, wherein X is selected from 6-bromo-7-hydroxycoumarin-4-ylmethyl;

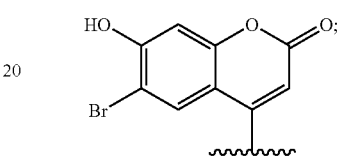

8-bromo-7-hydroxyquinolinyl;

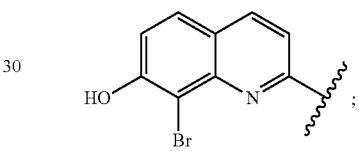

or a nitrodibenzofuran moiety

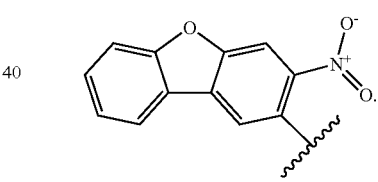

* * * * *

```
                        SEQUENCE LISTING

<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 1
gacttgaggc agacatattt ccgat                                             25

<210> SEQ ID NO 2
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 2
tatgtctgcc                                                              10

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 3
gggaatctgc atggcgtctg tttag                                             25

<210> SEQ ID NO 4
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 4
gtaatcgtac ttgcagcagg tgaca                                             25

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 5
```

-continued

```
cactgagtcc ttatttcact atatc                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 6
gcttgaggtc tctgatagcc tgcat                                              25

<210> SEQ ID NO 7
<211> LENGTH: 12
<212> TYPE: DNA
<213> ORGANISM: Artificial Sequence
<220> FEATURE:
<223> OTHER INFORMATION: Synthetic Oligomer

<400> SEQUENCE: 7
tatgtctgcc tc                                                            12

<210> SEQ ID NO 8
<211> LENGTH: 14
<212> TYPE: DNA
<213> ORGANISM: Artificial Sequence
<220> FEATURE:
<223> OTHER INFORMATION: Synthetic Oligomer

<400> SEQUENCE: 8
tatgtctgcc tcaa                                                          14

<210> SEQ ID NO 9
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 9
tatgtctgcc tcaagt                                                        16

<210> SEQ ID NO 10
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 10
gcctcaagtc                                                               10

<210> SEQ ID NO 11
<211> LENGTH: 12
<212> TYPE: DNA
<213> ORGANISM: Artificial Sequence
<220> FEATURE:
<223> OTHER INFORMATION: Synthetic Oligomer

<400> SEQUENCE: 11
ctgcctcaag tc                                                            12

<210> SEQ ID NO 12
<211> LENGTH: 14
<212> TYPE: DNA
<213> ORGANISM: Artificial Sequence
<220> FEATURE:
```

```
<223> OTHER INFORMATION: Synthetic Oligomer

<400> SEQUENCE: 12
gtctgcctca agtc                                                      14

<210> SEQ ID NO 13
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 13
atgtctgcct caagtc                                                    16

<210> SEQ ID NO 14
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 14
gcagattccc                                                           10

<210> SEQ ID NO 15
<211> LENGTH: 13
<212> TYPE: DNA
<213> ORGANISM: Artificial Sequence
<220> FEATURE:
<223> OTHER INFORMATION: Synthetic Oligomer

<400> SEQUENCE: 15
caagtacgat tac                                                       13

<210> SEQ ID NO 16
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 16
ggactcagtg                                                           10

<210> SEQ ID NO 17
<211> LENGTH: 10
<212> TYPE: DNA
<213> ORGANISM: Artificial Sequence
<220> FEATURE:
<223> OTHER INFORMATION: Synthetic Oligomer

<400> SEQUENCE: 17
gacctcaagc                                                           10

<210> SEQ ID NO 18
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 18
atcggaaata tgtctgcctc aagtc                                          25

<210> SEQ ID NO 19
```

```
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 19
ctaaacagac gccatgcaga ttccc                                          25

<210> SEQ ID NO 20
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 20
tgtcacctgc tgcaagtacg attac                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 21
gatatagtga aataaggact cagtg                                          25

<210> SEQ ID NO 22
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 22
atgcaggcta tcagagacct caagc                                          25
```